US010406397B1

(12) United States Patent
Graham

(10) Patent No.: US 10,406,397 B1
(45) Date of Patent: *Sep. 10, 2019

(54) JOINT SEPARATOR FOR BODY ALIGNMENT

(71) Applicant: Richard A. Graham, Sunset Beach, CA (US)

(72) Inventor: Richard A. Graham, Sunset Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/011,533

(22) Filed: Jun. 18, 2018

(51) Int. Cl.
*A63B 21/00* (2006.01)
*A63B 21/04* (2006.01)
(Continued)

(52) U.S. Cl.
CPC ....... *A63B 21/4039* (2015.10); *A61H 1/0218* (2013.01); *A63B 21/0442* (2013.01); *A63B 21/055* (2013.01); *A63B 21/4009* (2015.10); *A63B 21/4034* (2015.10); *A63B 23/0238* (2013.01); *A63B 23/03525* (2013.01);
(Continued)

(58) Field of Classification Search
CPC .......... A61H 1/0218; A61H 2201/0103; A61H 2201/1609; A61H 2201/1623; A63B 21/0442; A63B 21/055; A63B 21/4039; A63B 21/4009; A63B 21/4034; A63B 23/0238; A63B 23/03525; A63B 23/0417; A63B 71/0619; A63B 24/0087; A63B 2023/006; A63B 2208/0252; A63B 2225/09; A63B 2225/62; A63B 2225/50; A63B 2071/0661; A63B 2071/0683
See application file for complete search history.

(56) References Cited

U.S. PATENT DOCUMENTS 2,806,471 A 9/1957 Breese
3,068,002 A 12/1962 Balne
(Continued)

FOREIGN PATENT DOCUMENTS

DE 2638077 3/1977
JP 404327849 11/1992
(Continued)

OTHER PUBLICATIONS

Alf Breig, M.D. Adverse Mechanical Tension in the Central Nervous System Copyright 1978 p. 17 figure A and B [4A].
(Continued)

*Primary Examiner* — Megan Anderson
(74) *Attorney, Agent, or Firm* — Knobbe Martens Olson & Bear, LLP

(57) ABSTRACT

A spinal treatment system includes a traction device, an exercise device adapted for imparting curvature to the lumbar or sacral spine of a user and for manipulating the spine and intervertebral discs with decompression force, and a cushion coupled to the traction device and configured to bear against one or both of a head of the user and the thoracic spine of the user. The exercise device includes a frame for placement on the floor. A pad or inflatable bladder is carried by the top surface of the frame. A body strap attachment portion encompasses the thoracic-sacral spinal vertebrae region of the user and secures the frame to the user. The cushion includes one or more pad sections or inflatable bladder sections.

29 Claims, 48 Drawing Sheets

(51) Int. Cl.
*A63B 21/055* (2006.01)
*A63B 23/02* (2006.01)
*A63B 23/035* (2006.01)
*A63B 23/04* (2006.01)
*A63B 24/00* (2006.01)
*A63B 71/06* (2006.01)
*A61H 1/02* (2006.01)
*A63B 23/00* (2006.01)

(52) U.S. Cl.
CPC ...... *A63B 23/0417* (2013.01); *A63B 24/0087* (2013.01); *A63B 71/0619* (2013.01); *A61H 2201/0103* (2013.01); *A61H 2201/1609* (2013.01); *A61H 2201/1623* (2013.01); *A63B 2023/006* (2013.01); *A63B 2071/0661* (2013.01); *A63B 2071/0683* (2013.01); *A63B 2208/0252* (2013.01); *A63B 2225/09* (2013.01); *A63B 2225/50* (2013.01); *A63B 2225/62* (2013.01)

(56) References Cited

U.S. PATENT DOCUMENTS

| | | | |
|---|---|---|---|
| 3,521,623 A | 7/1970 | Nichols | |
| 3,667,457 A | 6/1972 | Zumaglini | |
| 3,765,412 A | 10/1973 | Ommaya | |
| 3,899,797 A | 8/1975 | Gunst | |
| 3,974,827 A | 8/1976 | Bodeen | |
| 4,024,861 A | 5/1977 | Vincent | |
| 4,043,668 A | 8/1977 | Goetz | |
| D247,312 S | 2/1978 | Zeiss | |
| 4,114,611 A | 9/1978 | Lyle | |
| 4,135,503 A | 1/1979 | Romano | |
| 4,159,020 A | 6/1979 | von Soiron | |
| 4,161,946 A | 7/1979 | Zuesse | |
| 4,194,501 A | 3/1980 | Watt | |
| 4,391,466 A | 7/1983 | Smith | |
| 4,463,947 A | 8/1984 | Kloenne | |
| 4,583,255 A | 4/1986 | Mogaki | |
| 4,583,532 A | 4/1986 | Jones | |
| 4,669,455 A | 6/1987 | Bellati | |
| 4,736,736 A | 4/1988 | Moers | |
| RE32,791 E | 11/1988 | Saunders | |
| 4,805,603 A | 2/1989 | Cumberland | |
| 4,838,613 A | 6/1989 | Smith | |
| D302,592 S | 8/1989 | Holmes | |
| 4,981,131 A | 1/1991 | Hazard | |
| 4,995,378 A | 2/1991 | Dyer | |
| 5,003,968 A | 4/1991 | Mars | |
| 5,062,414 A | 11/1991 | Grim | |
| 5,067,483 A | 11/1991 | Freed | |
| 5,070,865 A | 12/1991 | Iams | |
| 5,147,287 A | 9/1992 | Jewell | |
| 5,154,186 A | 10/1992 | Laurin | |
| 5,181,904 A | 1/1993 | Cook | |
| 5,190,348 A | 3/1993 | Colasanti | |
| 5,201,761 A | 4/1993 | Serola | |
| 5,207,716 A | 5/1993 | McReynolds | |
| 5,211,162 A | 5/1993 | Gillen, Jr. | |
| 5,232,424 A | 8/1993 | Pearson | |
| 5,244,393 A | 9/1993 | Perry | |
| 5,258,017 A | 11/1993 | Myers | |
| 5,279,310 A | 1/1994 | Hsien | |
| 5,292,175 A | 3/1994 | Artz | |
| 5,305,750 A | 4/1994 | Makita | |
| 5,338,276 A | 8/1994 | Jull | |
| 5,382,226 A | 1/1995 | Graham | |
| 5,403,266 A | 4/1995 | Bragg | |
| 5,407,418 A | 4/1995 | Szpur | |
| 5,410,472 A | 4/1995 | Anderson | |
| 5,423,861 A | 6/1995 | Kelley | |
| 5,472,401 A | 12/1995 | Rouillard | |
| 5,538,486 A | 7/1996 | France | |
| 5,560,056 A | 10/1996 | Tai | |
| 5,562,324 A | 10/1996 | Massara | |
| 5,569,176 A | 10/1996 | Graham | |
| 5,713,841 A | 2/1998 | Graham | |
| 5,738,640 A | 4/1998 | Carlson-Orsi | |
| 5,772,281 A | 6/1998 | Massara | |
| 5,906,586 A | 5/1999 | Graham | |
| 5,933,890 A | 8/1999 | Codd | |
| 6,007,501 A | 12/1999 | Cabados | |
| 6,039,737 A | 3/2000 | Dyer | |
| D445,505 S | 7/2001 | Shapiro | |
| 6,305,040 B1 | 10/2001 | Myler | |
| 6,390,997 B1 | 5/2002 | Vitko | |
| 6,506,174 B1 | 1/2003 | Saunders | |
| 6,544,152 B2 | 4/2003 | Rosati | |
| 6,592,184 B1 | 7/2003 | Segal | |
| 6,648,844 B2 | 11/2003 | Kamerman | |
| D486,235 S | 2/2004 | Haddock | |
| 6,899,690 B2 | 5/2005 | Saunders | |
| D508,566 S | 8/2005 | Graham | |
| 7,022,094 B2 | 4/2006 | Buckman | |
| 7,059,678 B1 * | 6/2006 | Taylor | A47C 7/405 297/284.4 |
| 7,060,085 B2 | 6/2006 | Graham | |
| 7,066,897 B2 | 6/2006 | Huang | |
| 7,104,935 B2 | 9/2006 | Matsuoka | |
| 7,108,671 B2 | 9/2006 | Saunders | |
| 7,264,601 B2 | 9/2007 | Liao | |
| 7,566,314 B2 | 7/2009 | Saunders | |
| 7,634,949 B2 | 12/2009 | Lodge | |
| 7,967,735 B2 | 6/2011 | Hudswell | |
| 8,029,453 B2 | 10/2011 | Graham | |
| 8,083,705 B2 | 12/2011 | Saunders | |
| 8,100,846 B1 | 1/2012 | LaMonica | |
| 8,734,372 B1 | 5/2014 | Graham | |
| 8,764,693 B1 | 7/2014 | Graham | |
| 9,241,820 B2 * | 1/2016 | Graham | A61F 5/01 |
| 9,801,779 B2 * | 10/2017 | Breibart | A63B 23/185 |
| 2003/0088200 A1 | 5/2003 | Saunders | |
| 2003/0125650 A1 | 7/2003 | Grosso | |
| 2003/0130696 A1 | 7/2003 | Hurd | |
| 2004/0143206 A1 | 7/2004 | Saunders | |
| 2006/0161087 A1 | 7/2006 | Carter | |
| 2006/0206046 A1 | 9/2006 | Saunders | |
| 2007/0079415 A1 | 4/2007 | Carlson | |
| 2007/0105696 A1 | 5/2007 | Castel | |
| 2007/0293796 A1 | 12/2007 | Graham | |
| 2008/0248936 A1 * | 10/2008 | Ferriss | A61H 7/001 482/142 |
| 2009/0118657 A1 | 5/2009 | Saunders | |
| 2009/0187127 A1 | 7/2009 | Buckman | |

FOREIGN PATENT DOCUMENTS

| | | |
|---|---|---|
| WO | WO 87/00424 | 1/1987 |
| WO | WO 1996/014810 A2 | 5/1996 |
| WO | WO 1996/014810 A3 | 8/1996 |

OTHER PUBLICATIONS

Cailliet, R., M.D., Low Back Pain Syndrome, Edition 4, Pain Series, Copyright 1994 [1A] p. 5, [1B] pp. 6-8, [1C] pp. 6-8.

Donald D. Harrison, Ph.D., M.S., D.C., The Physics of Spinal Correction Copyright 1994 [2A] Fig. 3-3. [2B] Fig 1-21. [2C] Fig 3-3 and Fig 7-6, [2D] Fig 3-6., [2E] Figures 7-2,7-3.

Kirkaldy-Willis, M.A., M.D., F.R.C.S., (Edin), F.A.C.S., Managing Low Back Pain, Copyright 1988, [3A] p. 306.

Norman Shealy, M.D., Ph.D. 2008 IRB Approved MRI Study of the Effects of Axial Linear Traction and Expanding Ellipsoidal Decompression (EED®) via Posture Pump® on Cervical Curve, Disc Protrusions and Disc Height, Copyright 2008, Practical Pain Management Mar. 2010.

Norman Shealy, M.D., Ph.D. 2006 IRB Approved Study of Cervical Decompression Treatment, Copyright 20008, Practical Pain Management Apr. 2007.

* cited by examiner

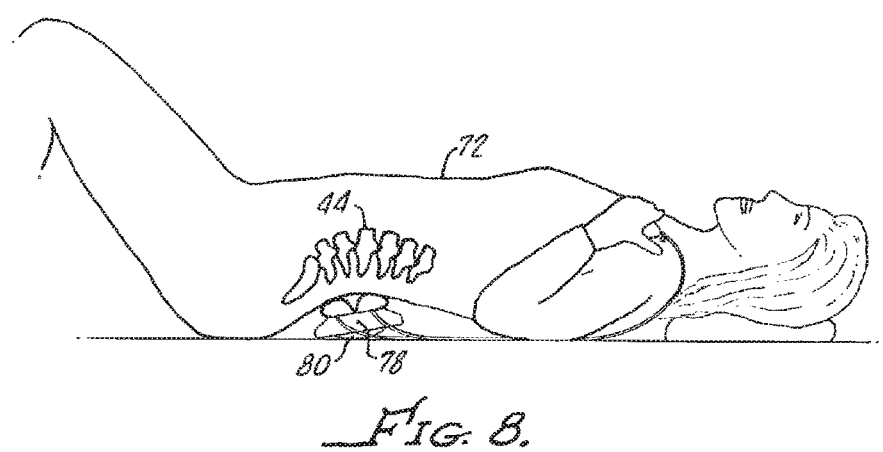
FIG. B.

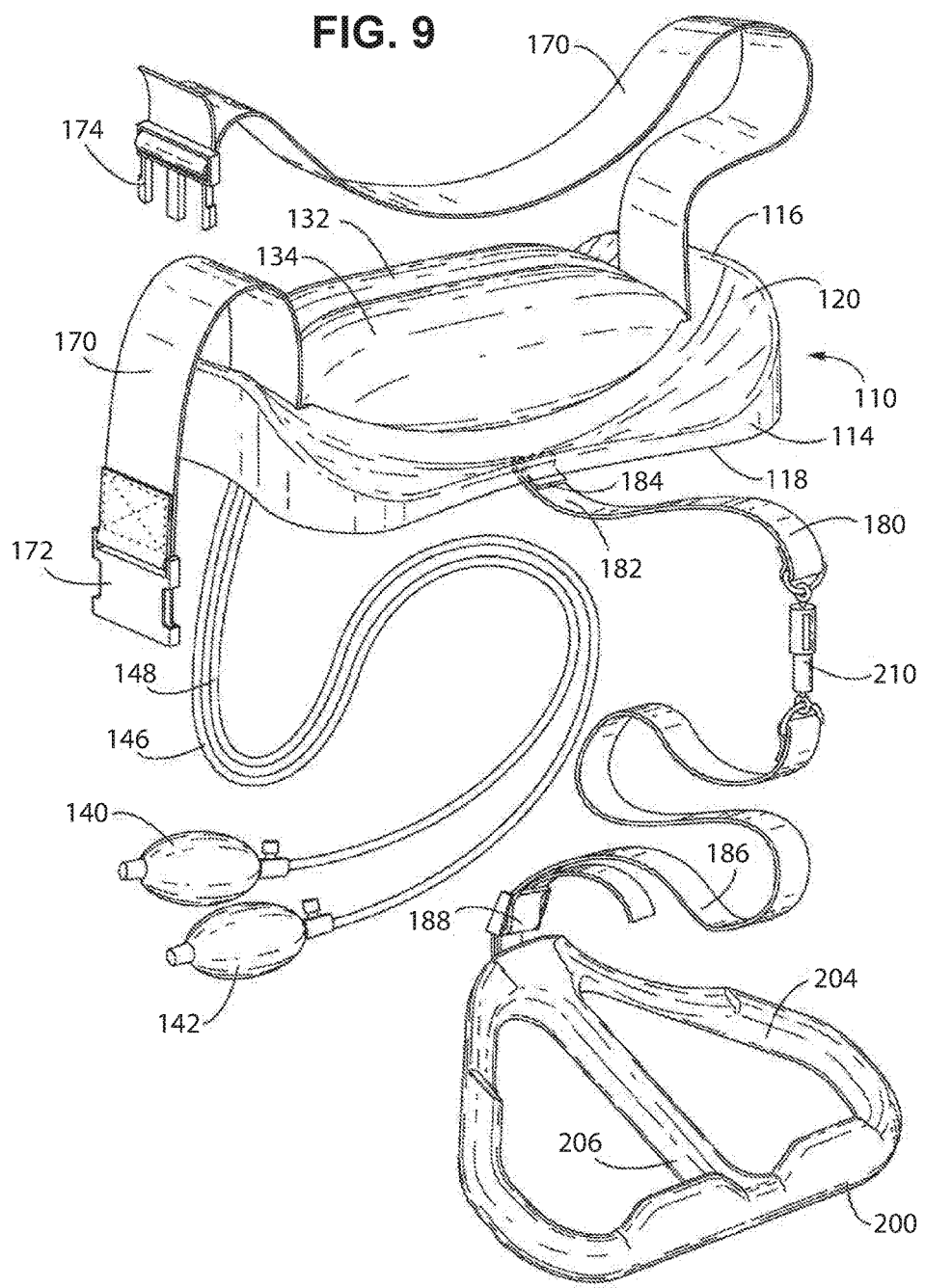

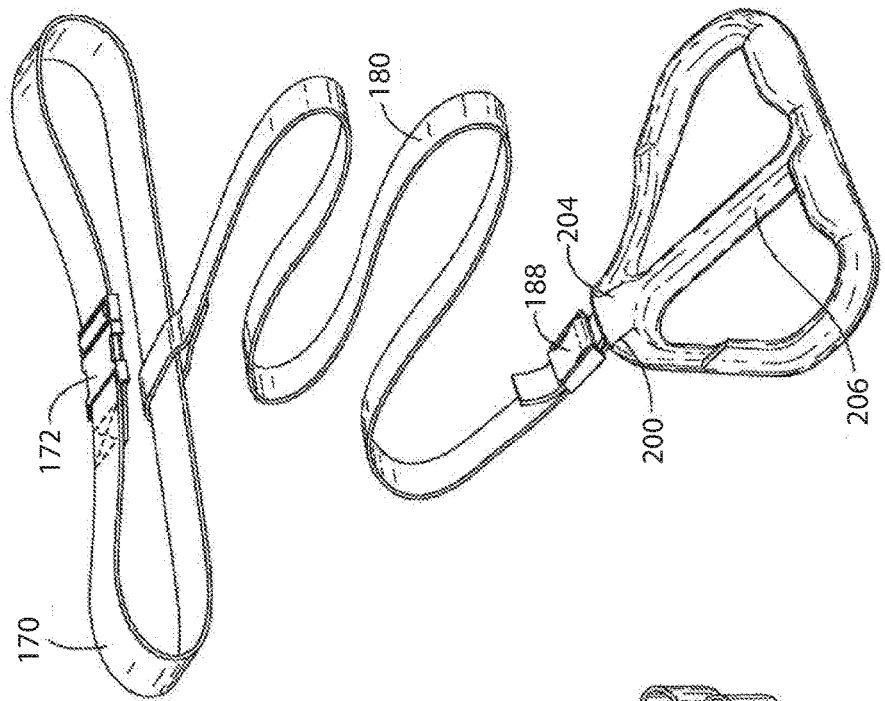
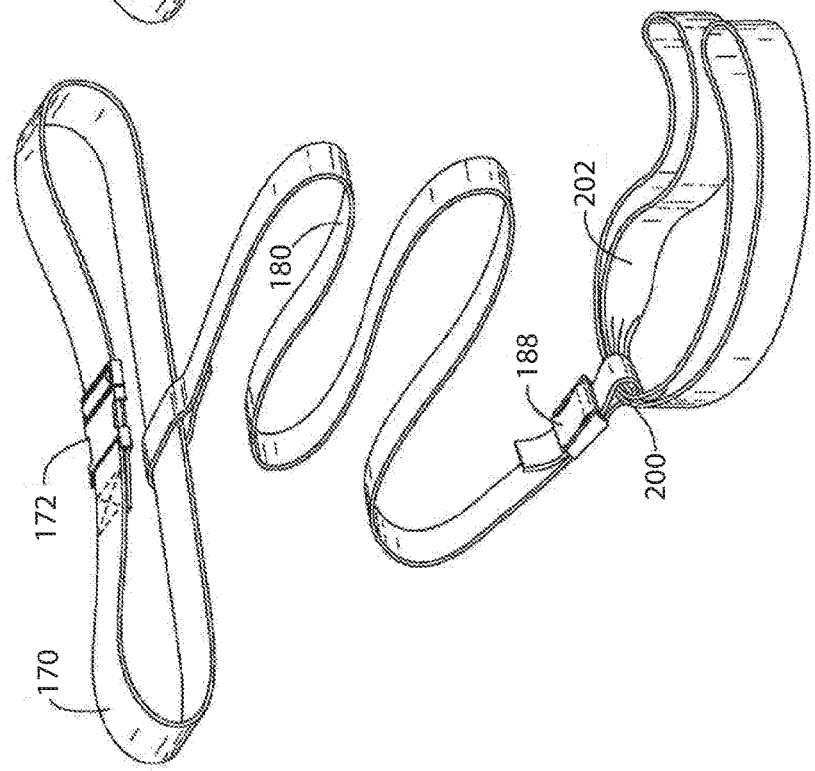

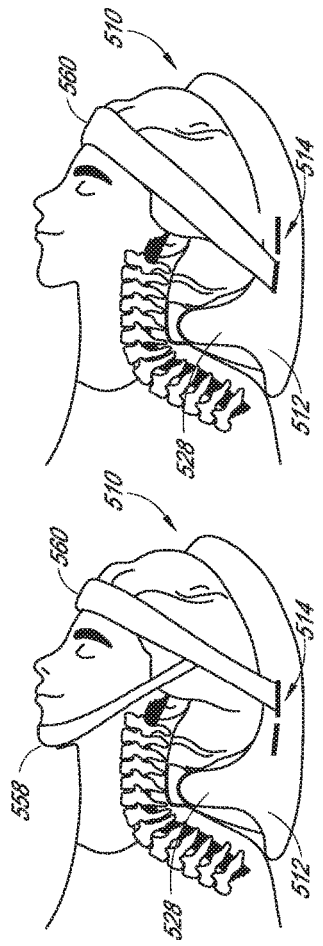
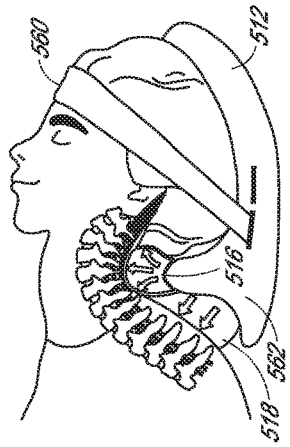
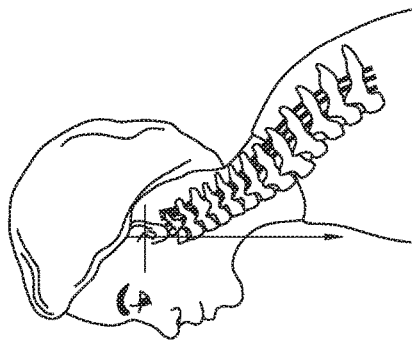
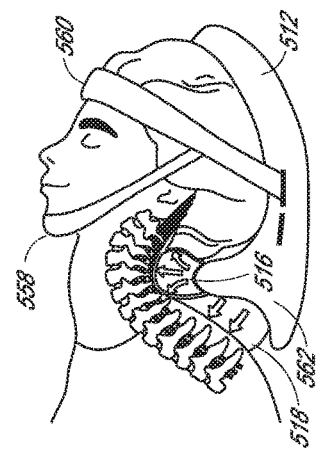
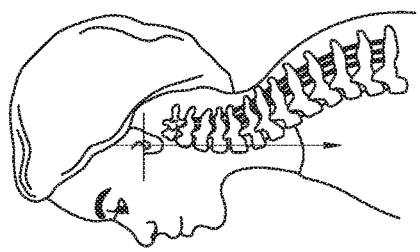
FIG. 36A FIG. 36B FIG. 36C FIG. 36D FIG. 36E FIG. 36F

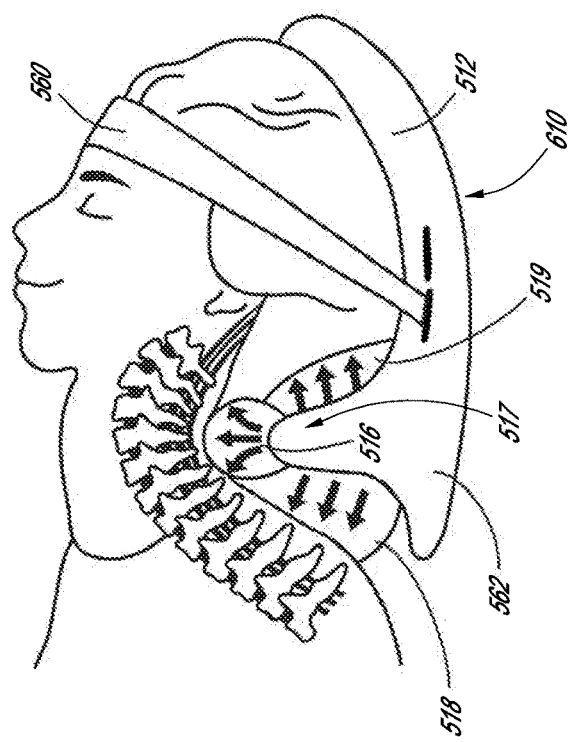
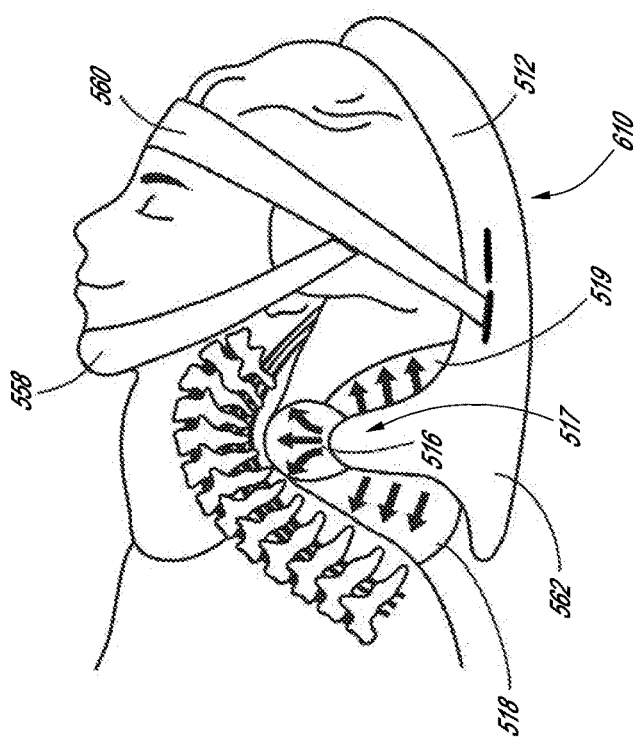
FIG. 49B
FIG. 49A

JOINT SEPARATOR FOR BODY ALIGNMENT

CROSS-REFERENCE TO RELATED APPLICATIONS

Any and all applications for which a foreign or domestic priority claim is identified in the Application Data Sheet as filed with the present application, are hereby incorporated by reference herein under 37 CFR 1.57.

BACKGROUND

Field

The present invention relates to an exercising device directed at alignment of the body and spinal vertebrae. More specifically, the present invention relates to the apparatus and methods for decompressing the spinal vertebrae using the pulling forces of the lower body, leg muscles, abdominal muscles, back, and neck to urge and correct aberrant spinal vertebrae postures.

Description of the Related Art

The spinal column is a bony column forming the main structural support of the skeleton of a human being and it consists of bony vertebrae linked by flexible joints and held together by ligaments and flexible gelatinous discs of cartilage. The spinal column of an adult human being consists of thirty-three vertebrae in which the last nine of these are fused to form the sacrum and the coccyx at the back of the pelvis. The 24 movable vertebrae are the 7 cervical (neck), 12 dorsal, and 5 lumbar. The vertebrae form a column for the skeleton and the arches are positioned so the space enclosed is an effective tube or canal. This houses and protects the spinal cord and within it the spinal fluid circulates. Without the seepage of fluids into the spinal column, the discs will further dehydrate, which may result in further loss of mobility, crippling, and even nerve damage. Thus, nutrient transport of fluids surround the spinal column is important in maintaining spinal health. It is known that the spine has a number of curvatures along the sagittal plane, namely, the cervical and lumbar curvatures in which the spine is convex toward the front of the body and the dorsal and sacral curvatures in which the spine is convex toward the back of the body. These alternating curves provide strength and balance to the body and are essential to allowing a person to walk upright. The lumbar and cervical curves of the spine normally define forward curves of about 35 to about 45 degrees whereby weight is distributed relatively evenly on individual vertebral surfaces and discs.

In individuals with lost or reversed cervical and lumbar spinal curves due to injury, illness, genetic predisposition, habitual microtrauma or simply poor posture, the weight of the body bears forwardly on the soft, non-bony intervertebral discs, inhibiting fluid transfer and causing the discs to wear, dehydrate and degenerate. Over time, these individuals exhibit a significant loss of natural joint movement. Lack of natural movement in the spine over time causes a reduction in the imbibition of nutrient rich fluids that normally lubricate and maintain flexibility of the spine. Without this seepage of fluids into the spinal column, the discs will further dehydrate, which may result in further loss of mobility, crippling and possible nerve damage. It is further noted that the intervertebral discs' indigenous vascular fluid supply disappears at approximately 20 years of age. Thus, active nutrient transport of fluids surrounding the spinal column is particularly important to maintaining spinal health of adults.

Axial/Linear/Longitudinal traction has long been employed to decompress cervical joints of the spine. Typically the head is pulled, pried, lifted or otherwise separated from the thorax along the Y axis (+Y axis translation or elevation translation). Ostensibly, to pry the joints apart at the posterior, forward flexion (+X axis rotation) is often employed in conjunction with or as an unavoidable component of linear traction. Linear traction or elevation translation applied to a curved column decreases or removes the curve. Likewise, adding the component of flexion or + rotation about the X axis, would apply a buckling force to the cervical spine and have the effect of reversing the curve (−Z axis translation). These forces, powerful enough to separate the spinal joints, are unfortunately antithetical to the natural geometry and biomechanics of the human cervical spine. The anchor points commonly used in Axial/Linear/Longitudinal traction are the head as it is pulled away from the thorax and/or the trapezius muscles as the thorax is pushed away from the restrained head. U.S. Pat. No. 4,805,603 to Cumberland describes a method where the head and thorax are separated by two platforms with an expanding air chamber between the two platforms. These methods, due to their linear function reduce, remove or reverse the proper cervical curve. U.S. Pat. No. 6,506,174 to Saunders also describes a linear traction system.

Some alternatives to axial/linear/longitudinal traction for disc, joint and nerve decompression seek to maintain a normal lordotic curve. For example, as described herein, U.S. Pat. Nos. 5,382,226, 5,569,176, 5,713,841, 5,906,586, 7,060,085, 8,029,453, and D508,5665 to Graham, each of which is hereby incorporated by reference herein in its entirety, disclose some embodiments of systems for decompression. In two IRB approved studies utilizing multiple MRI's, an embodiment of the disclosed systems showed a consistent ability to draw bulging disc material back toward the disc proper and away from the subarachnoid space and spinal cord while simultaneously enhancing or restoring the cervical lordotic curve during and after one 20 minute treatment. Patients reported immediate symptomatic relief of cervical pain. However, there exists a need for improved decompression systems that also address hyper-kyphosis of the upper thoracic spine, mid thoracic spine and compression of the occipital-cervical junction.

In addition to spinal traction devices which are well known for stretching the spine longitudinally in order to restore lost mobility, devices have been developed for either passively or actively restoring the normal curves of the spine to prevent the disabling effects of lost or impaired curvature mentioned hereinabove. An example for at home use device includes a Method and Portable Apparatus for Spinal Adjustment disclosed in U.S. Pat. Pub. No. US2003/0130696 to Hurd. In this device, a user employs the effects of gravity combined with simple leverage over a convex rigid surface to adjust the user's spine. Another example of a passive device includes, for example, the Spinal Column Correction Device disclosed in U.S. Pat. No. 5,279,310 to Hsein. In this device, a user is strapped to a series of raised supports that define what the normal curvatures of the spine should be. According to the inventor, the weight of the user's body will bear against the raised supports to correct abnormal curvature in the spine.

An example of a useful device that actively exercises the abdominal muscle and spine is disclosed in U.S. Pat. No. 7,060,085 to Graham entitled Rocking Vectored Pneumatic Joint Separator Inflatable Cervical Traction and Exercising Device, which is hereby incorporated by reference herein in its entirety. An abdominal muscle and spine-exercising device in accordance with the invention generally includes a frame having a top surface and a bottom surface. A first arched projection is disposed in the top surface along with a first inflatable bladder disposed on the first arched projection for directly bearing against lower thoracic and upper lumbar vertebrae of a user's spine in a first direction. A second inflatable bladder is disposed on the first arched projection for directly bearing against the mid-lumbar and lumbo-sacral vertebrae of the spine in a second direction. The first and second directions are divergent along a sagittal plane of the user in order to enhance an elliptical curve in the thoraco-lumbar/lumbo-sacral spine. A second arched projection is disposed on the bottom surface for enabling the frame and bladders to be rocked by the user in a direction transverse to a longitudinal axis of the frame. This rocking action provides exercise for the abdominal, low-back and pelvic muscles while the spine is inflated into an elliptical shape.

Another useful device that actively exercises the normal lordotic, i.e. forward, curves of a spine is disclosed in U.S. Pat. No. 5,382,226 to Graham entitled Inflatable Cervical Traction and Exercising Device, which is hereby incorporated by reference herein in its entirety. In the Graham patent, a device is disclosed which utilizes an inflatable bladder for actively forcing the cervical spine into a forward semi-circular curve. This exercising of the spine promotes fluid imbibition through the spinal vertebrae and intervertebral discs.

U.S. Pat. No. 5,906,586 to Graham, which is hereby incorporated by reference herein in its entirety, provides for a device and method for maintaining spinal health which utilizes a dual action air chamber defining multiple vectors of force to be applied to a spine, particularly to the lumbar spinal region. The device gradually lifts and separates the vertebrae in a manner that surpasses the effectiveness and comfort of conventional traction devices and passive spinal correction devices using a frame for aligning the upper spine.

U.S. Pat. No. 8,029,453 to Graham, which is hereby incorporated by reference herein in its entirety, provides a leg carrier slidably disposed in a conventional manner on a table for providing pelvis translation. In order to prevent or control twisting of the lower body, knee fenders may be fixed to the leg carrier. A lumbar sacral unit disposed on the support table between the cervical device and carrier is provided for enhancing an elliptical arch in the users' lower spine. The lumbar sacral unit is also described in U.S. Pat. Nos. 5,713,841, 5,569,176, and D508,566 to Graham, each of which is hereby incorporated by reference herein in its entirety.

U.S. Pat. Nos. 8,734,372, 8,764,693, and 9,095,419 to Graham, each of which is hereby incorporated by reference herein in its entirety, describe decompression systems for addressing hyper-kyphosis of the upper thoracic spine. U.S. patent application Ser. No. 15/857,246 to Graham, which is hereby incorporated by reference herein in its entirety, describes decompression systems for addressing hyper-kyphosis of the upper thoracic spine, mid thoracic spine and compression of the occipital-cervical junction.

The present invention provides for a combination leg muscle, abdominal muscle and spine-exercising device utilizing the vectoring of the earlier Graham work and further providing for apparatus capable of exercising, decompressing, and aligning the lower body and leg muscles while the spinal vertebrae are pneumatically molded into the accepted elliptical configuration of the thoraco-lumbar/lumbo-sacral spine to the legs. The present invention further provides for systems for decompression that address hyper-kyphosis of the upper thoracic spine, mid thoracic spine, and compression of the occipital-cervical junction.

SUMMARY

Described herein are some embodiments of a leg muscle, abdominal muscle, and spinal exercise device for redefining curvature to the lumbar/sacral spine and for manipulating the spine and intervertebral discs with decompression force from the lower body. This device generally comprises a means for manipulating and redefining the curvature of the spine and a frame.

Specifically, the means for manipulating and redefining the curvature of the spine includes a top surface along with a first inflatable bladder disposed for directly bearing against lower thoracic and upper lumbar vertebrae of a user's spine in a first direction. A second inflatable bladder is disposed for directly bearing against the mid-lumbar and lumbo-sacral vertebrae of the spine in a second direction to enhance the lower body strength and curve in spine. The adjacent inflated bladders, or alternately inflated bladders, provide diverging forces against the user's spine and thereby cause stretching and longitudinal aligning of the spinal vertebrae while promoting fluid imbibition throughout the vertebrae and discs. Thus, initially, the inflated first bladder may lift the thoracic-lumbar spinal vertebrae while the inflated second bladder may lift the lumbar-sacral spinal vertebrae thereby manipulating and redefining the semi-elliptical curvature in the spine.

More specifically, a body strap attachment for encompassing the user's body and securing the frame connects to an elongate stirrup strap member having a proximal end and a distal end. Preferably, the body attachment connects two ends of a strap, for example by means of a buckle, for adjustably securing the frame against the user's lumbar region.

The elongate stirrup strap member having a proximal end attached to the body strap attachment thereby connecting to the user's spine and frame, and a distal end attached to a stirrup for encompassing the user's feet/legs to enable decompression force from the lower body to the spine. Alternatively, the elongate stirrup strap member may include an attachable pressure gauge for measuring the decompression force exerted by the feet/legs on the lower body. A handheld monitor communicates with the pressure gauge for the user to monitor applied decompression or exercise force.

Even more specifically a stirrup attachment engagable by the user's feet/legs is provided for enabling pulling force from the legs and lower body to the spine. This stirrup attachment further enables the user to exercise the leg muscles while decompressing the thoraco-lumbar/lumbo-sacral spinal vertebrae which are pneumatically molded by the inflated bladders into the accepted elliptical configuration. Thus the spinal vertebrae are urged and molded into the natural elliptical alignment, the joints are lubricated and aligned, and the lower body muscles including the legs, abdominal, lower-back, and pelvic muscles are stretched and exercised.

Alternatively, the exercise device adapted for the user to exercise and strengthen the lower body muscles the proximal end is attached to the body strap attachment without the frame spine for enabling decompression pulling force aligned from the legs and lower body to the spine.

The device described hereinabove is suitable for performing a method for decompressing the spine and for exercising the lower body muscles, leg muscles, abdominal muscles, comprising the steps of:

(a) providing a frame attachable against the user's spine with first and second bladders disposed on a top of said frame and a rocker projection disposed on a bottom of said frame;

(b) inflating a bladder bearing against the lower thoracic and upper lumbar vertebrae and inflating another bladder bearing against the middle lumbar and lumbo-sacral vertebrae in order to create traction and spinal arc in the lower spinal region and to stretch lower body muscle groups, leg muscles;

(c) inflating and exhausting alternatively the bladder bearing against the lower thoracic and upper lumbar with the bladder bearing against the middle lumbar and lumbo-sacral vertebrae;

(d) encompassing the user's waist/lumbar region and securing the frame with a body strap attachment;

(e) connecting the body strap attachment to an elongate stirrup strap attached to tension gauge for monitoring decompression force and attached to a stirrup for encompassing the user's feet/legs;

(f) engaging slidably the user's feet/legs into the stirrup for enabling stress aligned from the legs and lower body to the spine;

(g) creating aligned decompression forces between the leg muscles and lower abdominal muscles by pulling the stirruped legs/feet in a direction away from the spine away from the spine to decompress, urge, and align the spinal vertebrae;

(h) monitoring the tension gauge with a handheld monitor and controlling the decompression forces between the leg muscles and lower abdominal muscles and repeating the exercising force to strengthen the lower body, spine, and legs.

Alternatively, the device described hereinabove is suitable for performing a method, in accordance with the present invention, for exercising the lower body, legs, and spine to enable and promote lower body and spinal alignment, comprising the steps of:

(a) encompassing the user's thoracic-sacral spinal vertebrae region and securing the frame with a body strap attachment (b) connecting the body strap attachment to an elongate stirrup strap attached to tension gauge for monitoring decompression force and attached to a stirrup for encompassing the user's feet/legs;

(c) engaging slidably the user's feet/legs into the stirrup for enabling stress aligned from the legs and lower body to the spine;

(d) creating aligned decompression forces between the leg muscles and lower abdominal muscles by pulling the stirruped legs/feet in a direction away from the spine away from the spine to decompress, urge, and align the spinal vertebrae;

(e) monitoring the tension gauge with a handheld monitor and controlling the decompression forces between the feet/leg muscles and lower abdominal muscles and repeating the exercising force to strengthen the lower body, spine, and legs.

Described herein are some embodiments of decompression and traction systems that maintain, enhance and restore a normal lordotic curve, counter hyper-kyphosis of the upper and mid thoracic spine and decompress the occipital-cervical junction. Methods of assembling and using the decompression and traction systems described herein are also included. These decompression and traction systems and related methods are described in greater detail below.

One aspect of the present invention is the recognition that traditionally available traction systems do not provide devices, systems and methods that simultaneously address cervical lordotic curve loss/reversal (hypolordosis/kyphosis), and the often accompanying posterior (−Z) translation (hyper-kyphosis) of the upper thoracic spine. Embodiments and methods described herein preferably provide pneumatic radial decompression and traction equipment for treatment of the cervical and thoracic spine including a free-standing frame, first and second expandable bladders, the first expandable bladder providing positive pressure to support a cervical spinal portion in a normal lordotic curve configuration, and the second expandable bladder providing positive pressure to support a thoracic spinal portion in a normal curve configuration to counter hyper-kyphosis of the upper thoracic spine.

According to certain embodiments of the invention, devices, systems and methods are described that simultaneously address cervical lordotic curve loss/reversal (hypolordosis/kyphosis), and the often accompanying posterior (−Z) translation (hyper-kyphosis) of the upper thoracic spine.

In relation to the head and neck, −Z translation of the upper thoracic spine is an integral part of anterior or "Forward Head Carriage." As the head shifts forward and/or the upper thoracic spine moves posterior, the weight of the head and neck, approximately 15 pounds, creates a forward buckling force (−Y and +Z combination) on the thoracic spine. This continuous forward and downward force begets more forward head carriage and more compressive action to the cervical and thoracic intervertebral discs and bodies. Many are familiar with the term "Dowagers Hump" where hyper kyphosis of the thoracic spine is so pronounced as to be obvious with the naked eye. While approximately 30% of these postural defects (especially in women) are said to be caused by anterior thoracic vertebral body fractures due to osteoporosis, most hyper-kyphotic postures are developed over time by continuous anterior and downward force on the cervical and thoracic intervertebral discs and vertebral bodies.

As people spend long hours crouched in front of computer screens, wear heavy back packs, are involved whiplash type auto and sports injuries, forward head posture with associated cervical curve loss, and hyper thoracic kyphosis has become more prevalent. Neck and back pain, muscle tension and spasm, headaches, neuropathies and degenerative vertebral joint disease result from continuous cervical-thoracic disc and joint compression. While there have been elastic bands and braces applied to the spine to pull or hold it upright in an attempt to ameliorate worsening posture, results are mixed.

In some embodiments, the devices, systems and methods described herein apply pneumatic forces directly to the offending spinal apexes in opposing directions. With the simultaneous application of two separate air cells or pneumatic air chambers the cervical spine is locked and powerfully decompressed into its proper lordotic or curved configuration (</\>) with −Y +Z +Y force vectors while the hyper kyphotic area of the upper thoracic spine is simultaneously decompressed with a combination +Z/−Y force mid-vector. The cervical spine's lordotic curve is powerfully decompressed and enhanced while the thoracic hyper-kyphosis is simultaneously reduced. In some embodiments, a two pump system can be employed to alternate or unevenly inflate the pneumatic air chambers. In some embodiments, a complex multi vectored pneumatic air chamber can be used in place of two individual cells. In some embodiments, the devices, systems and methods described herein use the entire cervical spine including the occiput (base of skull) as a first anchor point and the upper thoracic spine as a second point. The pneumatic air chambers can directly contact the cervical spine/occiput and the upper 25% of the thoracic spine.

According to one embodiment, a traction device comprises a frame, a first bladder portion, a second bladder portion, a strap, and a pump. The first bladder expands in an outward direction a distance greater than in a transverse direction. The second bladder expands in an angular direction. The second bladder is positioned generally below and to the side of the first bladder. The frame is secured to the user's head. Upon expanding in the outward direction, the first bladder bears against the back of the user's neck and forces the cervical spine to curve forwardly. Upon expanding in the transverse direction, the first bladder applies an angular traction to the cervical spine. Upon expanding in the angular direction, the second bladder bears angularly against the back of the user's upper thoracic region and forces the thoracic spine to decompress and reduces hyper-kyphosis of the upper thoracic spine.

In certain embodiments, a traction device for imparting a forward curve to the cervical spine and reducing hyper-kyphosis of the upper thoracic spine is provided. The device comprises a frame adapted to be supported on a rigid support surface. The frame is configured to be disposed about a user's head and neck and defines contact surfaces for abutting the rigid support surface. The frame has a neck support extending between first and second side portions of the frame. A first inflatable elongated bladder is coupled to the neck support and configured to be positioned below a neck of a user during use. The first inflatable elongated bladder is expandable in a first direction outwardly from the neck support toward the neck of a user and expandable in a second direction substantially normal to the first direction upon inflation. A second inflatable elongated bladder is coupled to the neck support and configured to be positioned below the upper thoracic region of a user during use. The second inflatable elongated bladder is expandable in a third direction angularly from the neck support toward the upper thoracic spine of a user upon inflation. A securing strap is coupled to the frame and configured to secure the frame to the user's head such that the first inflatable elongated bladder is disposed adjacent the back of the user's neck and transverses the cervical spine such that the first direction of expansion is toward and substantially normal to the cervical spine. The second inflatable elongated bladder is disposed adjacent the back of the user's upper thoracic region and transverses the upper thoracic spine such that the third direction of expansion is toward and substantially normal to the upper thoracic spine. A pump system is provided for selectively inflating and deflating the first and second inflatable elongated bladders. Upon the first inflatable bladder expanding in the first direction, the first inflatable bladder bears outwardly against the back of the user's neck and forces the cervical spine to curve forwardly. Upon expanding in the second direction, the first inflatable bladder applies an angular traction to the cervical spine. Upon the second inflatable bladder expanding in the third direction, the second inflatable bladder bears angularly against the back of the user's upper thoracic region and forces the thoracic spine to decompress and reduces hyper-kyphosis of the upper thoracic spine.

In some embodiments, the traction device comprises a valve positioned in communication with the pump system and the first and second inflatable elongated bladders. The valve comprises varying lumen diameters that direct flow between the pump system and the first and second inflatable elongated bladders. The first inflatable elongated bladder is pivotably coupled to the neck support. A spacer is configured to be coupled between a portion of the frame and the second inflatable elongated bladder to adjust the angulation of the second inflatable elongated bladder during inflation.

In other embodiments, a traction device is provided for imparting a forward curve to the cervical spine and reducing hyper-kyphosis of the upper thoracic spine. The device comprises a frame having a transverse neck support projecting upwardly from first and second side portions defining a base of the frame. A first inflatable bladder portion is coupled to the neck support. The first inflatable bladder portion is configured to expand in an outward direction from the neck support a distance greater than the expansion of the first inflatable bladder portion in a transverse direction normal thereto. A second inflatable bladder portion is coupled to the neck support. The second inflatable bladder portion is configured to expand in an angular direction from the neck support. The second inflatable bladder portion is positioned generally below and to the side relative to the first inflatable bladder portion. A strap is coupled to the frame and configured to secure the frame to the user's head such that the first inflatable bladder portion is disposed adjacent the back of the user's neck and transverses the cervical spine such that the outward direction of expansion is toward and substantially normal to the cervical spine. The second inflatable bladder portion is disposed adjacent the back of the user's upper thoracic region and transverses the upper thoracic spine such that the angular direction of expansion is toward and substantially normal to the upper thoracic spine. A pump system is provided for inflating the first and second inflatable bladder portions. Upon the first inflatable bladder portion expanding in the outward direction, the first inflatable bladder portion bears outwardly against the back of the user's neck and forces the cervical spine to curve forwardly. Upon expanding in the transverse direction, the first inflatable bladder portion applies an angular traction to the cervical spine. Upon the second inflatable bladder portion expanding in the angular direction, the second inflatable bladder portion bears angularly against the back of the user's upper thoracic region and forces the thoracic spine to decompress and reduces hyper-kyphosis of the upper thoracic spine.

In some embodiments, a method is provided for imparting a forward curve to the cervical spine and reducing hyper-kyphosis of the upper thoracic spine. The method comprises securing a traction device to a user's head. The traction device comprises a support frame having a transverse neck support projecting upwardly from a base of the support frame and first and second inflatable bladder portions coupled to the neck support. The traction device is secured to the user's head includes positioning the traction device such that the first inflatable bladder portion transverses the cervical spine, and such that the second inflatable bladder portion transverses the upper thoracic spine. The first inflatable bladder portion is expanded in a direction outward from the neck support and toward and substantially normal to the cervical spine to force the cervical spine to curve forwardly. The first inflatable bladder portion is expanded in a transverse direction to apply an angular traction to the cervical spine. The second inflatable bladder portion is expanded in a direction toward and substantially normal to the upper thoracic spine to force the upper thoracic spine to decompress and reduce hyper-kyphosis of the upper thoracic spine.

In certain embodiments, methods may comprise alternately inflating and deflating the first and second bladder portions. Inflation and deflation of the first and second bladder portions can be repeated. The first inflatable bladder portion can have a semi-ellipsoidal configuration upon inflation. The second inflatable bladder portion can have a semi-ellipsoidal configuration upon inflation. During inflation or deflation, flow can be directed between the pump system and the bladder portion through a valve that comprises different lumen diameters to provide particular flow to or from the first and second inflatable bladder portions. Methods can include pivoting the first inflatable bladder relative to the neck support and/or positioning a spacer between a portion of the frame and the second inflatable bladder portion to adjust the angulation of the second inflatable bladder portion during inflation.

In some embodiments, a traction device is provided for imparting a forward curve to the cervical spine and reducing hyper-kyphosis of the upper thoracic spine. The device comprises a frame adapted to be supported on a rigid support surface. The frame is configured to be disposed about a user's head and neck and defines contact surfaces for abutting the rigid support surface. The frame has a neck support extending between first and second side portions of the frame. A first inflatable elongated bladder is coupled to the neck support and configured to be positioned below a neck of a user during use. The first inflatable elongated bladder is expandable in a first direction outwardly from the neck support toward the neck of a user and expandable in a second direction substantially normal to the first direction upon inflation. A second inflatable elongated bladder is coupled to the neck support and configured to be positioned below the upper thoracic region of a user during use. The second inflatable elongated bladder is expandable in a third direction angularly from the neck support toward the upper thoracic spine of a user upon inflation. A spacer is configured to be coupled between a portion of the frame and the second inflatable elongated bladder to adjust the angulation of the second inflatable elongated bladder during inflation. A pump system is provided for selectively inflating and deflating the first and second inflatable elongated bladders. Upon the first inflatable bladder expanding in the first direction, the first inflatable bladder bears outwardly against the back of the user's neck, and upon expanding in the second direction, the first inflatable bladder applies an angular traction to the cervical spine. Upon the second inflatable bladder expanding in the third direction, the second inflatable bladder bears angularly against the back of the user's upper thoracic region.

In certain embodiments, a traction device for imparting a forward curve to the cervical spine and reducing hyper-kyphosis of the upper thoracic spine comprises a frame having a transverse neck support projecting upwardly from first and second side portions defining a base of the frame. A first inflatable bladder portion is coupled to the neck support, the first inflatable bladder portion is configured to expand in an outward direction from the neck support a distance greater than the expansion of the first inflatable bladder portion in a transverse direction normal thereto. A second inflatable bladder portion is coupled to the neck support. The second inflatable bladder portion is configured to expand in an angular direction from the neck support. The second inflatable bladder portion is positioned generally below and to the side relative to the first inflatable bladder portion. A spacer is configured to be coupled between a portion of the frame and the second inflatable bladder portion to adjust the angulation of the second inflatable bladder portion during inflation. A pump system is provided for inflating the first and second inflatable bladder portions. Upon the first inflatable bladder portion expanding in the outward direction, the first inflatable bladder portion bears outwardly against the back of the user's neck. Upon expanding in the transverse direction, the first inflatable bladder portion applies an angular traction to the cervical spine. Upon the second inflatable bladder portion expanding in the angular direction, the second inflatable bladder portion bears angularly against the back of the user's upper thoracic region.

According to some implementations, additional features include a wedge-shaped spacer, a rotatable spacer, and/or a spacer in a horizontal position that is configured to adjust the angulation of the second inflatable bladder portion during inflation to provide lateral flexion traction. Other spacer systems are contemplated and can also be used. For example, any component or device that can be selectively adjusted and can contact at least a portion of the second inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

According to another implementation, a method of imparting a forward curve to the cervical spine and reducing hyper-kyphosis of the upper thoracic spine is provided. A traction device is secured to a user's head. The traction device comprises a support frame having a transverse neck support projecting upwardly from a base of the support frame and first and second inflatable bladder portions coupled to the neck support and a spacer coupled between a portion of the frame and the second inflatable bladder portion to adjust the angulation of the second inflatable bladder portion during inflation to provide lateral flexion traction. Securing the traction device to the user's head includes positioning the traction device such that the first inflatable bladder portion transverses the cervical spine, and such that the second inflatable bladder portion transverses the upper thoracic spine. The first inflatable bladder portion is expanded in a direction outward from the neck support and toward and substantially normal to the cervical spine to force the cervical spine to curve forwardly. The first inflatable bladder portion is expanded in a transverse direction to apply an angular traction to the cervical spine. The second inflatable bladder portion is expanded in a direction toward the upper thoracic spine to provide lateral flexion traction. In some embodiments, the spacer is rotated to adjust the angulation of the second inflatable bladder portion.

According to certain embodiments of the invention, devices, systems and methods are described that address compression of the occipital-cervical junction. In some embodiments, the devices, systems, and methods described herein apply pneumatic forces directly to the occiput.

In certain embodiments of the invention, devices, systems and methods are described that simultaneously address cervical lordotic curve loss/reversal (hypolordosis/kyphosis), the often accompanying posterior (−Z) translation (hyper-kyphosis) of the upper thoracic spine, and compression of the occipital-cervical junction. With the application of an air cell or pneumatic air chamber, the occipital-cervical junction is decompressed by the application of +Z/+Y force vectors.

In some embodiments, the devices, systems, and methods described herein apply pneumatic forces directly to the offending spinal apexes in opposing directions and to the occiput. With the simultaneous application of three separate air cells or pneumatic air chambers the cervical spine is locked and powerfully decompressed into its proper lordotic or curved configuration (</\>) with −Y +Z +Y force vectors while the hyper kyphotic area of the upper thoracic spine is simultaneously decompressed with a combination +Z/−Y force mid-vector and +Z/+Y force vectors are applied to the occiput to decompress the occipital-cervical junction. The cervical spine's lordotic curve is powerfully decompressed and enhanced while the thoracic hyper-kyphosis is simultaneously reduced and the occipital-cervical junction is decompressed. In some embodiments, a two pump system can be employed to alternate or unevenly inflate the pneumatic air chambers. In some embodiments, a three pump system can be employed to alternate or unevenly inflate the pneumatic air chambers. In some embodiments, a complex multi vectored pneumatic air chamber can be used in place of three individual cells. In some embodiments, the devices, systems and methods described herein use the entire cervical spine as a first anchor point, the upper thoracic spine as a second point, and the occiput as a third point. The pneumatic air chambers can directly contact the cervical spine/occiput and the upper 25%-40% of the thoracic spine.

In certain embodiments, a traction device is provided. The device comprises a frame having a base and a neck support coupled to the base to support the neck of a user during use, a first inflatable bladder portion coupled to the neck support, a second inflatable bladder portion coupled to the neck support, and a third inflatable bladder portion coupled to the neck support. The first inflatable bladder portion is configured to expand in an outward direction from the neck support toward the neck of a user and to expand in a transverse direction substantially normal to the outward direction upon inflation. The second inflatable bladder portion is configured to expand in a first angular direction from the neck support and is positioned generally inferior to the first inflatable bladder portion. The third inflatable bladder portion is configured to expand in a second angular direction from the neck support and is positioned generally superior to the first inflatable bladder portion. Upon the first inflatable bladder portion expanding in the outward direction, the first inflatable bladder portion bears outwardly against the back of the neck of the user as the first inflatable bladder is inflated and forces the cervical spine to curve forwardly, and upon expanding in the transverse direction, the first inflatable bladder portion applies an angular traction to the cervical spine as the first inflatable bladder is inflated. Upon the second inflatable bladder portion expanding in the first angular direction, the second inflatable bladder portion bears angularly against the back of the upper thoracic region of the user as the second inflatable bladder is inflated and forces the thoracic spine to decompress and reduces hyper-kyphosis of the upper thoracic spine. Upon the third inflatable bladder portion expanding in the second angular direction, the third inflatable bladder portion bears angularly against the occiput of the user as the third inflatable bladder is inflated and forces the occipital-cervical junction to decompress.

In certain embodiments, a spacer is configured to be coupled between a portion of the frame and the second inflatable bladder portion to adjust the angulation of the second inflatable bladder portion during inflation. In certain embodiments, a spacer is configured to be coupled between a portion of the frame and the third inflatable bladder portion to adjust the angulation of the third inflatable bladder portion during inflation. In certain embodiments, a pump system is provided for inflating the first, second, and third inflatable bladder portions. In certain embodiments, a valve is positioned in communication with the pump system and the first inflatable bladder portion, the second inflatable bladder portion, and the third inflatable bladder portion, wherein the valve comprises varying lumen diameters that direct flow between the pump system and the first inflatable bladder portion, the second inflatable bladder portion, and the third inflatable bladder portion. In certain embodiments, upon inflation, the third inflatable bladder portion can impart 15° to 20° of forward head flexion to the occiput of the user.

According to some implementations, additional features include a wedge-shaped spacer, a rotatable spacer, and/or a spacer in a horizontal position that is configured to adjust the angulation of the second inflatable bladder portion during inflation to provide lateral flexion traction. Other spacer systems are contemplated and can also be used. For example, any component or device that can be selectively adjusted and can contact at least a portion of the second inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

According to some implementations, additional features include a wedge-shaped spacer, a rotatable spacer, and/or a spacer in a horizontal position that is configured to adjust the angulation of the third inflatable bladder portion during inflation to provide lateral flexion traction. Other spacer systems are contemplated and can also be used. For example, any component or device that can be selectively adjusted and can contact at least a portion of the third inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

In some embodiments, the devices, systems, and methods described herein apply pneumatic forces directly to the cervical spine and the occiput. With the simultaneous application of two separate air cells or pneumatic air chambers the cervical spine is locked and powerfully decompressed into its proper lordotic or curved configuration (</\>) with −Y +Z +Y force vectors the occipital-cervical junction is simultaneously decompressed with +Z/+Y force vectors. The cervical spine's lordotic curve is powerfully decompressed and enhanced while the occipital-cervical junction is decompressed. In some embodiments, a two pump system can be employed to alternate or unevenly inflate the pneumatic air chambers. In some embodiments, a complex multi vectored pneumatic air chamber can be used in place of two individual cells. In some embodiments, the devices, systems and methods described herein use the entire cervical spine as a first anchor point, and the occiput as a second point.

In certain embodiments, a traction device is provided. The traction device comprises a frame having a base and a neck support coupled to the base to support the neck of a user during use, a first inflatable bladder portion coupled to the neck support, and a second inflatable bladder portion coupled to the neck support. The first inflatable bladder portion is configured to expand in an outward direction from the neck support toward the neck of the user and in a transverse direction substantially normal to the outward direction upon inflation. The second inflatable bladder portion is configured to be positioned superior to the first inflatable bladder portion and is expandable in an angular direction from the neck support toward an occiput of the user upon inflation. Upon the first inflatable bladder portion expanding in the outward direction, the first inflatable bladder portion bears outwardly against the back of the neck of the user as the first inflatable bladder is inflated and forces the cervical spine to curve forwardly, and upon expanding in the transverse direction, the first inflatable bladder portion applies an angular traction to the cervical spine as the first inflatable bladder is inflated. Upon the second inflatable bladder portion expanding in the angular direction, the second inflatable bladder portion bears angularly against the occiput of the user as the second inflatable bladder is inflated and forces the occipital-cervical junction to decompress.

In certain embodiments, a spacer is configured to be coupled between a portion of the frame and the second inflatable bladder portion to adjust the angulation of the second inflatable bladder portion during inflation. In certain embodiments, a pump system is provided for selectively inflating and deflating one or more of the first and second inflatable bladder portions. In certain embodiments, a valve is positioned in communication with the pump system and the first and second inflatable bladder portions, wherein the valve comprises varying lumen diameters that direct flow between the pump system and the first and second inflatable bladder portions.

According to some implementations, additional features include a wedge-shaped spacer, a rotatable spacer, and/or a spacer in a horizontal position that is configured to adjust the angulation of the second inflatable bladder portion during inflation to provide lateral flexion traction. Other spacer systems are contemplated and can also be used. For example, any component or device that can be selectively adjusted and can contact at least a portion of the second inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

In certain embodiments, a method of imparting a forward curve to the cervical spine and reducing hyper-kyphosis of the upper thoracic spine is provided. The method comprises a step of securing a traction device to a head of a user. The traction device comprises a support frame having a transverse neck support projecting upwardly from a base of the support frame and first and second inflatable bladder portions coupled to the neck support. Securing the traction device to the head comprises positioning the traction device such that the first inflatable bladder portion transverses the cervical spine, and such that the second inflatable bladder portion transverses an occiput of the user. The method further comprises a step of expanding the first inflatable bladder portion in a direction outward from the neck support and toward and substantially normal to the cervical spine to force the cervical spine to curve forwardly. The method also comprises a step of expanding the first inflatable bladder portion in a transverse direction to apply an angular traction to the cervical spine. The method further comprises a step of expanding the second inflatable bladder portion in a direction toward the occiput to apply an angular traction to the occipital-cervical junction.

In some embodiments, the method further comprising a step of alternately inflating and deflating the first and second bladder portions. In some embodiments, the method further comprises a step of repeating inflation and deflation of the first and second bladder portions. In some embodiments, the second inflatable bladder portion has a semi-ellipsoidal configuration upon inflation. In some embodiments, the traction device comprises a third inflatable bladder portion coupled to the neck support. In some embodiments, securing the traction device to the head comprises positioning the traction device such that the third inflatable bladder portion transverses the upper thoracic spine. In some embodiments, the method further comprises a step of inflating the third bladder portion in a direction toward the upper thoracic spine to force the thoracic spine to decompress and reduce hyper-kyphosis of the upper thoracic spine. In some embodiments, the traction device comprises a valve positioned in communication with a pump system and the first inflatable bladder portion, the second inflatable bladder portion, and the third inflatable bladder portion. In some embodiments, the method further comprises a step of directing flow from the pump system through the valve to the first inflatable bladder portion, the second inflatable bladder portion, and the third inflatable bladder portion.

In some embodiments, the devices, systems, and methods described herein apply pneumatic forces directly to the thoracic spine and to the occiput. With the simultaneous application of two separate air cells or pneumatic air chambers, the hyper kyphotic area of the upper thoracic spine is simultaneously decompressed with a combination +Z/−Y force mid-vector and the occipital-cervical junction is decompressed with +Z/+Y force vectors. The thoracic hyper-kyphosis is simultaneously reduced and the occipital-cervical junction is decompressed. In some embodiments, the simultaneous application of two separate air cells or pneumatic air chambers, to the thoracic spine and the occiput can impart linear traction. In some embodiments, a two pump system can be employed to alternate or unevenly inflate the pneumatic air chambers. In some embodiments, a complex multi vectored pneumatic air chamber can be used in place of two individual cells. In some embodiments, the devices, systems and methods described herein use the upper thoracic spine as a first anchoring point and the occiput as a second point. The pneumatic air chambers can directly contact the cervical spine/occiput and the upper 25%-40% of the thoracic spine.

In certain embodiments, a traction device is provided. The traction device comprises a frame having a base and a neck support coupled to the base to support the neck of a user during use, a first inflatable bladder portion coupled to the neck support, and a second inflatable bladder portion coupled to the neck support. The first inflatable bladder portion is configured to expand a first angular direction from the neck support. The second inflatable bladder portion is configured to be positioned superior to the first inflatable bladder portion and is expandable in a second angular direction from the neck support toward an occiput of the user upon inflation. Upon the first inflatable bladder portion expanding in the first angular direction, the first inflatable bladder portion bears angularly against the back of the upper thoracic region of the user as the second inflatable bladder is inflated and forces the thoracic spine to decompress and reduces hyper-kyphosis of the upper thoracic spine. Upon the second inflatable bladder portion expanding in the angular direction, the second inflatable bladder portion bears angularly against the occiput of the user as the second inflatable bladder is inflated and forces the occipital-cervical junction to decompress.

In certain embodiments, a spacer is configured to be coupled between a portion of the frame and the second inflatable bladder portion to adjust the angulation of the second inflatable bladder portion during inflation. In certain embodiments, a pump system is provided for selectively inflating and deflating one or more of the first and second inflatable bladder portions. In certain embodiments, a valve is positioned in communication with the pump system and the first and second inflatable bladder portions, wherein the valve comprises varying lumen diameters that direct flow between the pump system and the first and second inflatable bladder portions.

According to some implementations, additional features include a wedge-shaped spacer, a rotatable spacer, and/or a spacer in a horizontal position that is configured to adjust the angulation of the first inflatable bladder portion during inflation to provide lateral flexion traction. Other spacer systems are contemplated and can also be used. For example, any component or device that can be selectively adjusted and can contact at least a portion of the first inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

According to some implementations, additional features include a wedge-shaped spacer, a rotatable spacer, and/or a spacer in a horizontal position that is configured to adjust the angulation of the second inflatable bladder portion during inflation to provide lateral flexion traction. Other spacer systems are contemplated and can also be used. For example, any component or device that can be selectively adjusted and can contact at least a portion of the second inflatable bladder portion can be used to impart lateral flexion traction. Additionally, in some cases a component or device need not be adjustable, for example, a spacer or other component could be provided on a traction device to cause the second inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

In certain embodiments, a traction device is provided. The traction device comprises a frame having a base and a neck support coupled to the base to support the neck of a user during use and an inflatable bladder portion coupled to the neck support. The inflatable bladder portion is configured to expand in an angular direction from the neck support. Upon the inflatable bladder portion expanding in the angular direction, the inflatable bladder portion bears angularly against the back of the upper thoracic region and the mid thoracic region of the user as the inflatable bladder is inflated and forces the thoracic spine to decompress and reduces hyper-kyphosis of the upper thoracic spine and the mid thoracic spine.

In certain embodiments, the inflatable bladder portion is a first inflatable bladder portion and the angular direction is a first angular direction. In certain embodiments, the traction device further comprises a second inflatable bladder portion coupled to the neck support, and the second inflatable bladder portion bladder portion is expandable in a second angular direction from the neck support toward a occiput of the user upon inflation. In certain embodiments, upon the second inflatable bladder portion expanding in the second angular direction, the second inflatable bladder portion bears angularly against the occiput of the user as the second inflatable bladder is inflated and forces the occipital-cervical junction to decompress the occipital-cervical junction. In certain embodiments, the traction device further comprises a third inflatable bladder portion coupled to the neck support, and the third inflatable bladder portion is configured to expand in an outward direction from the neck support toward the neck of the user and in a transverse direction substantially normal to the outward direction upon inflation. In certain embodiments, upon the third inflatable bladder portion expanding in the outward direction, the third inflatable bladder portion bears outwardly against the back of the neck of the user as the third inflatable bladder is inflated and forces the cervical spine to curve forwardly, and upon expanding in the transverse direction, the third inflatable bladder portion applies an angular traction to the cervical spine as the third inflatable bladder is inflated.

In certain embodiments, the inflatable bladder portion is a first inflatable bladder portion, and the traction device further comprises a second inflatable bladder portion coupled to the neck support. In certain embodiments, the second inflatable bladder portion is configured to expand in an outward direction from the neck support toward the neck of the user and in a transverse direction substantially normal to the outward direction upon inflation. In certain embodiments, upon the second inflatable bladder portion expanding in the outward direction, the second inflatable bladder portion bears outwardly against the back of the neck of the user as the second inflatable bladder is inflated and forces the cervical spine to curve forwardly, and upon expanding in the transverse direction, the second inflatable bladder portion applies an angular traction to the cervical spine as the second inflatable bladder is inflated.

In certain embodiments, a spacer is configured to be coupled between a portion of the frame and the inflatable bladder portion to adjust the angulation of the inflatable bladder portion during inflation. In certain embodiments, a pump system is provided for selectively inflating and deflating the inflatable bladder portion. In certain embodiments, a valve is positioned in communication with the pump system and the inflatable bladder portion, wherein the valve comprises varying lumen diameters that direct flow between the pump system and the inflatable bladder portion.

According to some implementations, additional features include a wedge-shaped spacer, a rotatable spacer, and/or a spacer in a horizontal position that is configured to adjust the angulation of the inflatable bladder portion during inflation to provide lateral flexion traction. Other spacer systems are contemplated and can also be used. For example, any component or device that can be selectively adjusted and can contact at least a portion of the inflatable bladder portion can be used to impart lateral flexion traction. Additionally, in some cases a component or device need not be adjustable, for example, a spacer or other component could be provided on a traction device to cause the inflatable bladder portion to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

These and other objects and advantages of the present disclosure will become readily apparent from the following detailed description taken in conjunction with the accompanying drawings.

In certain embodiments, a spinal treatment system is provided. The spinal treatment system comprises a traction device, an exercise device adapted for imparting curvature to the lumbar or sacral spine of a user and for manipulating the spine and intervertebral discs with decompression force, and a cushion coupled to the traction device. The traction device comprises a frame having a base and a neck support coupled to the base to support the neck of a user during use. The traction device also comprises an inflatable bladder portion coupled to the neck support and configured to expand. Upon the inflatable bladder portion expanding, the inflatable bladder portion imparts a force to one or more of an occipital-cervical junction of the user, a cervical spine of the user, and a thoracic spine of the user. The exercise device comprises a frame for placement on a floor and having a top surface and a bottom surface, the bottom surface configured to rest upon the floor. The top surface and bottom surface are in a spaced apart relationship forming a hollow portion therebetween. The exercise device further comprises a pad or an inflatable bladder carried by the top surface of the frame, the pad or inflatable bladder defined by an upper and lower portion. The exercise device further comprises a body strap attachment for encompassing the thoracic-sacral spinal vertebrae region of the user and securing the frame to the user. The cushion is configured to bear against one or both of a head of the user and the thoracic spine of the user, the cushion comprising one or more pad sections or inflatable bladder sections.

In certain embodiments, the spinal treatment system further comprises an elongate stirrup strap member having a proximal end and a distal end, the proximal end attachable to the frame thereby connecting to the spinal region of the user, and the proximal end is adapted to be disposed behind the spinal region of the user. In certain embodiments, the pad or inflatable bladder of the exercise device is a first pad or first inflatable bladder, and the exercise device further comprises a second pad or second inflatable bladder carried by the top surface of the frame. In certain embodiments, the first pad or first inflatable bladder is disposed for directly bearing against the lower thoracic and upper lumbar vertebrae of the spine of the user. In certain embodiments, the second pad or second inflatable bladder is disposed for directly bearing against the mid-lumbar and lumbo-sacral vertebrae of the spine of the user. In certain embodiments, the pad or inflatable bladder of the exercise device is disposed for directly bearing against the lower thoracic and upper lumbar vertebrae of the spine of the user and the mid-lumbar and lumbo-sacral vertebrae of the spine of the user. In certain embodiments, the spinal treatment system comprises one or more straps configured to couple the traction device with the exercise device. In certain embodiments, the spinal treatment system comprises one or more straps configured to couple the cushion with the exercise device. In certain embodiments, the spinal treatment system comprises a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface, and control the fluid delivery system to direct the flow of fluid to the inflatable bladder portion based on the one or more selections. In certain embodiments, the processor is configured to control the fluid delivery system to inflate the inflatable bladder portion to a user selected inflation amount or at a user selected inflation rate.

In certain embodiments, a spinal treatment system is provided. The spinal treatment system comprises a traction device and an exercise device adapted for imparting curvature to the lumbar or sacral spine of a user and for manipulating the spine and intervertebral discs with decompression force. The traction device comprises a frame having a base and a neck support coupled to the base to support the neck of a user during use. The traction device also comprises an inflatable bladder portion coupled to the neck support and configured to expand. Upon the inflatable bladder portion expanding, the inflatable bladder portion imparts a force to one or more of an occipital-cervical junction of the user, a cervical spine of the user, and a thoracic spine of the user. The exercise device a frame for placement on a floor and having a top surface and a bottom surface, the bottom surface configured to rest upon the floor. The top surface and bottom surface are in a spaced apart relationship forming a hollow portion therebetween. The exercise device also comprises a pad or an inflatable bladder carried by the top surface of the frame, the pad or inflatable bladder defined by an upper and lower portion. The exercise device also comprises a body strap attachment for encompassing the thoracic-sacral spinal vertebrae region of the user and securing the frame to the user.

In certain embodiments, the spinal treatment system comprises an elongate stirrup strap member having a proximal end and a distal end, the proximal end attachable to the frame thereby connecting to the spinal region of the user, and the proximal end is adapted to be disposed behind the spinal region of the user. In certain embodiments, the pad or inflatable bladder of the exercise device is a first pad or first inflatable bladder, and the exercise device further comprises a second pad or second inflatable bladder carried by the top surface of the frame. In certain embodiments, the first pad or first inflatable bladder is disposed for directly bearing against the lower thoracic and upper lumbar vertebrae of the spine of the user. In certain embodiments, the second pad or second inflatable bladder is disposed for directly bearing against the mid-lumbar and lumbo-sacral vertebrae of the spine of the user. In certain embodiments, the pad or inflatable bladder of the exercise device is disposed for directly bearing against the lower thoracic and upper lumbar vertebrae of the spine of the user and the mid-lumbar and lumbo-sacral vertebrae of the spine of the user. In certain embodiments, the spinal treatment system comprises one or more straps configured to couple the traction device with the exercise device. In certain embodiments, the spinal treatment system comprises a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface and control the fluid delivery system to direct the flow of fluid to the inflatable bladder portion of the traction device based on the one or more selections. In certain embodiments, the processor is configured to control the fluid delivery system to inflate the inflatable bladder portion to a user selected inflation amount or at a user selected inflation rate.

In certain embodiments, a spinal treatment system is provided. The spinal treatment system comprises an exercise device adapted for imparting curvature to the lumbar or sacral spine of a user and for manipulating the spine and intervertebral discs with decompression force, and a cushion coupled to the exercise device. The exercise device comprises a frame for placement on a floor and having a top surface and a bottom surface, the bottom surface configured to rest upon the floor. The top surface and bottom surface are in a spaced apart relationship forming a hollow portion therebetween. The exercise device also comprises a pad or an inflatable bladder carried by the top surface of the frame, the pad or inflatable bladder defined by an upper and lower portion. The exercise device also comprises a body strap attachment for encompassing the thoracic-sacral spinal vertebrae region of the user and securing the frame to the user. The cushion is configured to bear against one or both of a head of the user and the thoracic spine of the user. The cushion comprises one or more pad sections or inflatable bladder sections.

In certain embodiments, the spinal treatment system comprises an elongate stirrup strap member having a proximal end and a distal end, the proximal end attachable to the frame thereby connecting to the spinal region of the user, and the proximal end is adapted to be disposed behind the spinal region of the user. In certain embodiments, the pad or inflatable bladder of the exercise device is a first pad or first inflatable bladder, and the exercise device further comprises a second pad or second inflatable bladder carried by the top surface of the frame. In certain embodiments, the first pad or first inflatable bladder is disposed for directly bearing against the lower thoracic and upper lumbar vertebrae of the spine of the user. In certain embodiments, the second pad or second inflatable bladder is disposed for directly bearing against the mid-lumbar and lumbo-sacral vertebrae of the spine of the user. In certain embodiments, the pad or inflatable bladder of the exercise device is disposed for directly bearing against the lower thoracic and upper lumbar vertebrae of the spine of the user and the mid-lumbar and lumbo-sacral vertebrae of the spine of the user. In certain embodiments, the spinal treatment system comprises one or more straps configured to couple the cushion with the exercise device. In certain embodiments, the spinal treatment system comprises a pump system. In certain embodiments, the pump system comprises a user interface configured to receive one or more selections from a user, a fluid delivery system configured to direct the flow of fluid to the first inflatable bladder and/or second inflatable bladder of the exercise device, and a processor in communication with the user interface and fluid delivery system. In certain embodiments, the processor is configured to receive the one or more selections from the user interface and control the fluid delivery system to direct the flow of fluid to the first inflatable bladder and/or second inflatable bladder of the exercise device based on the one or more selections. In certain embodiments, the processor is configured to control the fluid delivery system to inflate the first inflatable bladder portion and/or second inflatable bladder portion to a user selected inflation amount or at a user selected inflation rate.

In certain embodiments, a method for exercising and decompressing the lower body muscles, leg muscles, abdominal muscles and spine is provided. The method comprises providing a frame with a pad having a volume that is not configured to be inflatable disposed on a top portion of the frame, said top portion of said frame disposed on a bottom of said frame, the frame comprising a hollow portion between the top portion and bottom of said frame. The method also comprises positioning the pad against one or more of the lower thoracic and upper lumbar vertebrae and the middle lumbar and lumbo-sacral vertebrae of a user in order to create traction and spinal arc in the lower spinal region and to stretch lower body muscle groups, leg muscles. The method also comprises encompassing a thoracic-sacral spinal vertebrae region of the user and securing the frame with a body strap attachment, the body strap attachment passing through the frame in a non-fixed relationship and partially disposed within the hollow portion. The method also comprises connecting an elongate stirrup strap to the frame and to a stirrup for encompassing the feet or legs of the user, wherein the elongate stirrup strap is disposed behind the user. The method always comprises engaging slidably the feet or legs of the user into the stirrup. The method also comprises creating aligned decompression forces between the leg muscles and lower abdominal muscles by pulling the stirruped legs or feet in a direction away from the spine to decompress, urge, and align the spinal vertebrae.

In certain embodiments, positioning the pad against one or more of the lower thoracic and upper lumbar vertebrae and the middle lumbar and lumbo-sacral vertebrae of the user comprises positioning the pad against the lower thoracic and upper lumbar vertebrae. In certain embodiments, positioning the pad against one or more of the lower thoracic and upper lumbar vertebrae and the middle lumbar and lumbo-sacral vertebrae of the user comprises positioning the pad against the middle lumbar and lumbo-sacral vertebrae. In certain embodiments, the pad is a first pad. In certain embodiments, the method comprises positioning the first pad against the lower thoracic and upper lumbar vertebrae of the user. In certain embodiments, the method comprising positioning a second pad against the middle lumbar and lumbo-sacral vertebrae. In certain embodiments, the method comprises securing a traction device to a head of the user. In certain embodiments, the traction device comprises a frame having a base and a neck support coupled to the base to support the neck of a user during use and an inflatable bladder portion coupled to the neck support. In certain embodiments, the method comprises expanding the inflatable bladder portion to impart a force to one or more of an occipital cervical junction of the user, a cervical spine of the user, and a thoracic spine of the user. In certain embodiments, the method comprises expanding the inflatable bladder portion using a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface, and control the fluid delivery system to direct the flow of fluid to the inflatable bladder portion based on the one or more selections. In certain embodiments, the processor is configured to control the fluid delivery system to inflate the inflatable bladder portion to a user selected inflation amount or at a user selected inflation rate.

In certain embodiments, a method for exercising and decompressing the lower body muscles, leg muscles, abdominal muscles and spine is provided. The method comprises providing a frame with a pad or inflatable bladder disposed on a top portion of the frame, said top portion of said frame disposed on a bottom of said frame, the frame comprising a hollow portion between the top portion and bottom of said frame. The method also comprises positioning the pad or inflatable bladder against one or more of the lower thoracic and upper lumbar vertebrae and the middle lumbar and lumbo-sacral vertebrae of a user in order to create traction and spinal arc in the lower spinal region and to stretch lower body muscle groups, leg muscles. The method also comprises encompassing a thoracic-sacral spinal vertebrae region of the user and securing the frame with a body strap attachment, the body strap attachment passing through the frame in a non-fixed relationship and partially disposed within the hollow portion. The method also comprises connecting an elongate stirrup strap to the frame and to a stirrup for encompassing the feet or legs of the user, wherein the elongate stirrup strap is disposed behind the user. The method always comprises engaging slidably the feet or legs of the user into the stirrup. The method also comprises creating aligned decompression forces between the leg muscles and lower abdominal muscles by pulling the stirruped legs or feet in a direction away from the spine to decompress, urge, and align the spinal vertebrae. The method also comprises securing a traction device to a head of the user. The traction device comprises a frame having a base and a neck support coupled to the base to support the neck of a user during use and an inflatable bladder portion coupled to the neck support. The method also comprises expanding the inflatable bladder portion of the traction device to impart a force to one or more of an occipital cervical junction of the user, a cervical spine of the user, and a thoracic spine of the user. The method also comprises positioning a cushion against one or both of the head of the user and the thoracic spine of the user. The cushion comprises one or more pad sections and/or inflatable bladder sections.

In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the lower thoracic and upper lumbar vertebrae. In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the middle lumbar and lumbo-sacral vertebrae. In certain embodiments, the pad or inflatable bladder is a first pad or first inflatable bladder. In certain embodiments, the method comprises positioning the first pad or first inflatable bladder against the lower thoracic and upper lumbar vertebrae of the user. In certain embodiments, the method comprising positioning a second pad or second inflatable bladder against the middle lumbar and lumbo-sacral vertebrae. In certain embodiments, the cushion is coupled to the traction device. The cushion can be coupled to the traction device by one or more straps. In certain embodiments, the cushion is coupled to the exercise device. The cushion can be coupled to the exercise device by one or more straps. In certain embodiments, the method comprises expanding the inflatable bladder portion of the traction device using a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface, and control the fluid delivery system to direct the flow of fluid to the inflatable bladder portion based on the one or more selections. In certain embodiments, the processor is configured to control the fluid delivery system to inflate the inflatable bladder portion of the traction device to a user selected inflation amount or at a user selected inflation rate. In certain embodiments, the method comprises expanding one or more inflatable bladders of the exercise device. In certain embodiments, the method comprises expanding one or more inflatable bladders of the exercise device using a pump system. In certain embodiments, the pump system comprises a user interface configured to receive one or more selections from a user, a fluid delivery system configured to direct the flow of fluid to one or more inflatable bladders of the exercise device and a processor in communication with the user interface and fluid delivery system. In certain embodiments, the processor is configured to receive the one or more selections from the user interface, and control the fluid delivery system to direct the flow of fluid to one or more inflatable bladders of the exercise device based on the one or more selections. In certain embodiments, the processor is configured to control the fluid delivery system to inflate one or more inflatable bladders of the exercise device to a user selected inflation amount or at a user selected inflation rate. In certain embodiments, the method comprises expanding one or more inflatable bladder sections of the cushion using a pump system. In certain embodiments, the pump system comprises a user interface configured to receive one or more selections from a user, a fluid delivery system configured to direct the flow of fluid to one or more inflatable bladder sections of the cushion, and a processor in communication with the user interface and fluid delivery system. In certain embodiments, the processor is configured to receive the one or more selections from the user interface, and control the fluid delivery system to direct the flow of fluid to one or more inflatable bladder sections of the cushion based on the one or more selections. In certain embodiments, the processor is configured to control the fluid delivery system to inflate one or more inflatable bladder sections of the cushion to a user selected inflation amount or at a user selected inflation rate.

In certain embodiments, a method for exercising and decompressing the lower body muscles, leg muscles, abdominal muscles and spine is provided. The method comprises providing a frame with a pad or inflatable bladder disposed on a top portion of the frame, said top portion of said frame disposed on a bottom of said frame, the frame comprising a hollow portion between the top portion and bottom of said frame. The method also comprises positioning the pad or inflatable bladder against one or more of the lower thoracic and upper lumbar vertebrae and the middle lumbar and lumbo-sacral vertebrae of a user in order to create traction and spinal arc in the lower spinal region and to stretch lower body muscle groups, leg muscles. The method also comprises encompassing a thoracic-sacral spinal vertebrae region of the user and securing the frame with a body strap attachment, the body strap attachment passing through the frame in a non-fixed relationship and partially disposed within the hollow portion. The method also comprises connecting an elongate stirrup strap to the frame and to a stirrup for encompassing the feet or legs of the user, wherein the elongate stirrup strap is disposed behind the user. The method always comprises engaging slidably the feet or legs of the user into the stirrup. The method also comprises creating aligned decompression forces between the leg muscles and lower abdominal muscles by pulling the stirruped legs or feet in a direction away from the spine to decompress, urge, and align the spinal vertebrae. The method also comprises securing a traction device to a head of the user. The traction device comprises a frame having a base and a neck support coupled to the base to support the neck of a user during use and an inflatable bladder portion coupled to the neck support. The method also comprises expanding the inflatable bladder portion of the traction device to impart a force to one or more of an occipital cervical junction of the user, a cervical spine of the user, and a thoracic spine of the user.

In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the lower thoracic and upper lumbar vertebrae. In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the middle lumbar and lumbo-sacral vertebrae. In certain embodiments, the pad or inflatable bladder is a first pad or first inflatable bladder. In certain embodiments, the method comprises positioning the first pad or first inflatable bladder against the lower thoracic and upper lumbar vertebrae of the user. In certain embodiments, the method comprising positioning a second pad or second inflatable bladder against the middle lumbar and lumbo-sacral vertebrae. In certain embodiments, the method comprises expanding the inflatable bladder portion of the traction device using a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface, and control the fluid delivery system to direct the flow of fluid to the inflatable bladder portion based on the one or more selections. In certain embodiments, the processor is configured to control the fluid delivery system to inflate the inflatable bladder portion of the traction device to a user selected inflation amount or at a user selected inflation rate. In certain embodiments, the method comprises expanding one or more inflatable bladders of the exercise device. In certain embodiments, the method comprises expanding one or more inflatable bladders of the exercise device using a pump system. In certain embodiments, the pump system comprises a user interface configured to receive one or more selections from a user, a fluid delivery system configured to direct the flow of fluid to one or more inflatable bladders of the exercise device and a processor in communication with the user interface and fluid delivery system. In certain embodiments, the processor is configured to receive the one or more selections from the user interface, and control the fluid delivery system to direct the flow of fluid to one or more inflatable bladders of the exercise device based on the one or more selections. In certain embodiments, the processor is configured to control the fluid delivery system to inflate one or more inflatable bladders of the exercise device to a user selected inflation amount or at a user selected inflation rate.

In certain embodiments, a method for exercising and decompressing the lower body muscles, leg muscles, abdominal muscles and spine is provided. The method comprises providing a frame with a pad or inflatable bladder disposed on a top portion of the frame, said top portion of said frame disposed on a bottom of said frame, the frame comprising a hollow portion between the top portion and bottom of said frame. The method also comprises positioning the pad or inflatable bladder against one or more of the lower thoracic and upper lumbar vertebrae and the middle lumbar and lumbo-sacral vertebrae of a user in order to create traction and spinal arc in the lower spinal region and to stretch lower body muscle groups, leg muscles. The method also comprises encompassing a thoracic-sacral spinal vertebrae region of the user and securing the frame with a body strap attachment, the body strap attachment passing through the frame in a non-fixed relationship and partially disposed within the hollow portion. The method also comprises connecting an elongate stirrup strap to the frame and to a stirrup for encompassing the feet or legs of the user, wherein the elongate stirrup strap is disposed behind the user. The method always comprises engaging slidably the feet or legs of the user into the stirrup. The method also comprises creating aligned decompression forces between the leg muscles and lower abdominal muscles by pulling the stirruped legs or feet in a direction away from the spine to decompress, urge, and align the spinal vertebrae. The method also comprises positioning a cushion against one or both of the head of the user and the thoracic spine of the user. The cushion comprises one or more pad sections and/or inflatable bladder sections.

In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the lower thoracic and upper lumbar vertebrae. In certain embodiments, positioning the pad or inflatable bladder against one or more of the lower thoracic and upper lumbar vertebrae and the middle lumbar and lumbo-sacral vertebrae of the user comprises positioning the pad or inflatable bladder against the middle lumbar and lumbo-sacral vertebrae. In certain embodiments, the pad or inflatable bladder is a first pad or first inflatable bladder. In certain embodiments, the method comprises positioning the first pad or first inflatable bladder against the lower thoracic and upper lumbar vertebrae of the user. In certain embodiments, the method comprising positioning a second pad or second inflatable bladder against the middle lumbar and lumbo-sacral vertebrae. In certain embodiments, the cushion is coupled to the exercise device. The cushion can be coupled to the exercise device by one or more straps. In certain embodiments, the method comprises expanding one or more inflatable bladders of the exercise device. In certain embodiments, the method comprises expanding one or more inflatable bladders of the exercise device using a pump system. In certain embodiments, the pump system comprises a user interface configured to receive one or more selections from a user, a fluid delivery system configured to direct the flow of fluid to one or more inflatable bladders of the exercise device and a processor in communication with the user interface and fluid delivery system. In certain embodiments, the processor is configured to receive the one or more selections from the user interface, and control the fluid delivery system to direct the flow of fluid to one or more inflatable bladders of the exercise device based on the one or more selections. In certain embodiments, the processor is configured to control the fluid delivery system to inflate one or more inflatable bladders of the exercise device to a user selected inflation amount or at a user selected inflation rate. In certain embodiments, the method comprises expanding one or more inflatable bladder sections of the cushion using a pump system. In certain embodiments, the pump system comprises a user interface configured to receive one or more selections from a user, a fluid delivery system configured to direct the flow of fluid to one or more inflatable bladder sections of the cushion, and a processor in communication with the user interface and fluid delivery system. In certain embodiments, the processor is configured to receive the one or more selections from the user interface, and control the fluid delivery system to direct the flow of fluid to one or more inflatable bladder sections of the cushion based on the one or more selections. In certain embodiments, the processor is configured to control the fluid delivery system to inflate one or more inflatable bladder sections of the cushion to a user selected inflation amount or at a user selected inflation rate.

In certain embodiments, a spinal treatment system is provided. The spinal treatment system comprises an exercise device adapted for imparting curvature to the lumbar or sacral spine of a user and for manipulating the spine and intervertebral discs with decompression force. The exercise device comprises a frame for placement on a floor and having a top surface and a bottom surface, the bottom surface configured to rest upon the floor. The top surface and bottom surface are in a spaced apart relationship forming a hollow portion therebetween. The exercise device further comprises a pad having a volume that is not configured to be inflatable carried by the top surface of the frame, the pad defined by an upper and lower portion. The exercise device further comprises a body strap attachment for encompassing the thoracic-sacral spinal vertebrae region of the user and securing the frame to the user.

In certain embodiments, the spinal treatment system comprises an elongate stirrup strap member having a proximal end and a distal end, the proximal end attachable to the frame thereby connecting to the spinal region of the user, and the proximal end is adapted to be disposed behind the spinal region of the user. In certain embodiments, the pad of the exercise device is a first pad, and the exercise device further comprises a second pad carried by the top surface of the frame. In certain embodiments, the second pad has a volume that is not configured to be inflated. In certain embodiments, the first pad is disposed for directly bearing against the lower thoracic and upper lumbar vertebrae of the spine of the user. In certain embodiments, the second pad is disposed for directly bearing against the mid-lumbar and lumbo-sacral vertebrae of the spine of the user. In certain embodiments, the pad of the exercise device is disposed for directly bearing against the lower thoracic and upper lumbar vertebrae of the spine of the user and the mid-lumbar and lumbo-sacral vertebrae of the spine of the user. In certain embodiments, the spinal treatment system comprises a traction device. In certain embodiments, the traction device comprises a frame having a base and a neck support coupled to the base to support the neck of a user during use. In certain embodiments, the traction device also comprises an inflatable bladder portion coupled to the neck support and configured to expand. In certain embodiments, upon the inflatable bladder portion expanding, the inflatable bladder portion imparts a force to one or more of an occipital-cervical junction of the user, a cervical spine of the user, and a thoracic spine of the user. In certain embodiments, the spinal treatment system comprises a cushion. In certain embodiments, the cushion is configured to bear against one or both of a head of the user and the thoracic spine of the user, the cushion comprising one or more pad sections or inflatable bladder sections. In certain embodiments, the spinal treatment system comprises one or more straps configured to couple the traction device with the exercise device. In certain embodiments, the spinal treatment system comprises one or more straps configured to couple the cushion with the exercise device. In certain embodiments, the spinal treatment system comprises a pump system. In certain embodiments, the pump system comprises a user interface configured to receive one or more selections from a user, a fluid delivery system configured to direct the flow of fluid to the inflatable bladder portion of the traction device, and a processor in communication with the user interface and fluid delivery system. In certain embodiments, the processor is configured to receive the one or more selections from the user interface, and control the fluid delivery system to direct the flow of fluid to the inflatable bladder portion based on the one or more selections. In certain embodiments, the processor is configured to control the fluid delivery system to inflate the inflatable bladder portion to a user selected inflation amount or at a user selected inflation rate.

BRIEF DESCRIPTION OF THE DRAWINGS

The accompanying drawings illustrate the invention. In such drawings:

FIGS. 6-8 illustrate the use of the abdominal muscle and spine exercise device in accordance with the present invention illustrating massage by bladders due to momentum provided by rocking which effects the elongation of the lordotic arch and promotes fluid imbibition throughout the vertebrae and disc.

FIG. 9 is a perspective view of the lower body and spinal exercise device in accordance with the present invention, including a frame having two inflatable bladders disposed thereon, a pair of handheld pumps for bladder inflation, a body attachment attached to a stirrup strap, a tension gauge, and an attached stirrup for feet/legs;

FIGS. 13-14 illustrate perspective top views of the body strap attachment which encompasses the user's spinal region, an elongate stirrup strap, and a stirrup. FIG. 13 illustrates the stirrup as an attachable looped band while FIG. 14 illustrates the stirrup as a partitioned annulus (ring) for aligning and supporting the feet and the lower body;

FIG. 15 illustrates the user in a relaxed position and FIG. 16 illustrates the user in the extended lower body position applying decompression force to the spine and inflated bladders against the user's spine to expand and redefine the curvature in the spine;

FIGS. 36A-F are illustrative views of a patient's spine in multiple configurations, including some embodiments of decompression and traction systems in use in deflated and inflated configurations.

FIGS. 49A-B are illustrative views of a patient's spine including embodiments of decompression and traction systems in use in inflated configurations.

DETAILED DESCRIPTION

With reference to FIGS. 1-4, there is shown an abdominal muscle and spine exercising device 10 which includes a frame 12 having a top surface 14 and a bottom surface 16.

Figure 1:
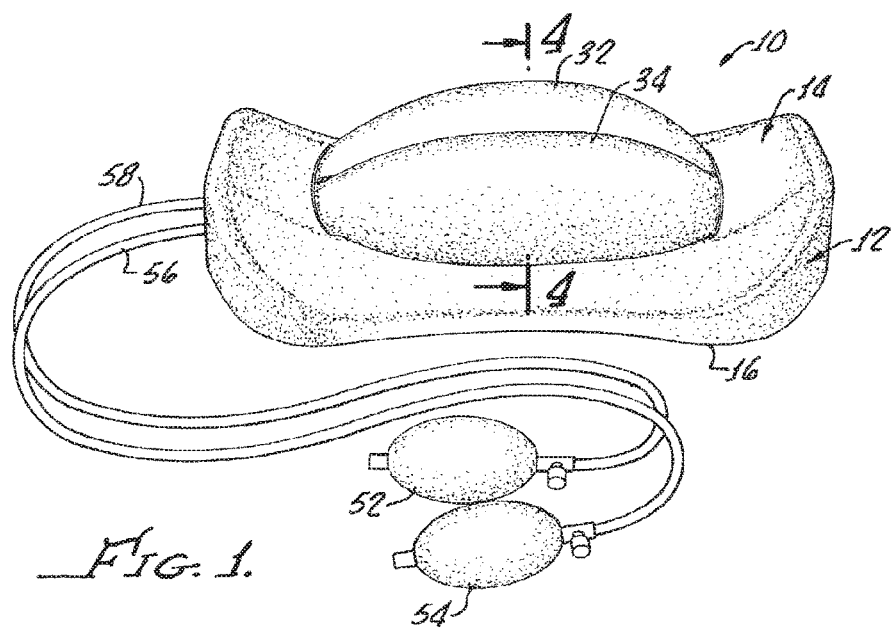
FIG. 1 is a perspective view of an abdominal muscle and spine-exercising device in accordance with the present invention generally showing a frame having a top surface with a first and second bladders disposed thereon and a pair of hand held pumps for bladder inflation.
Figure 2:
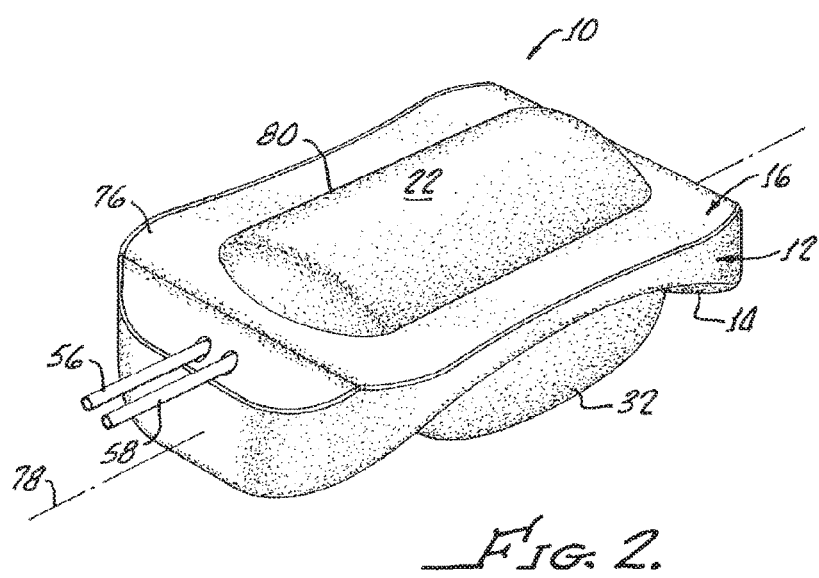
FIG. 2 is a perspective view of a bottom side of the device shown in FIG. 1 showing an arched projection for enabling the device to be rocked by the user.
Figure 3:
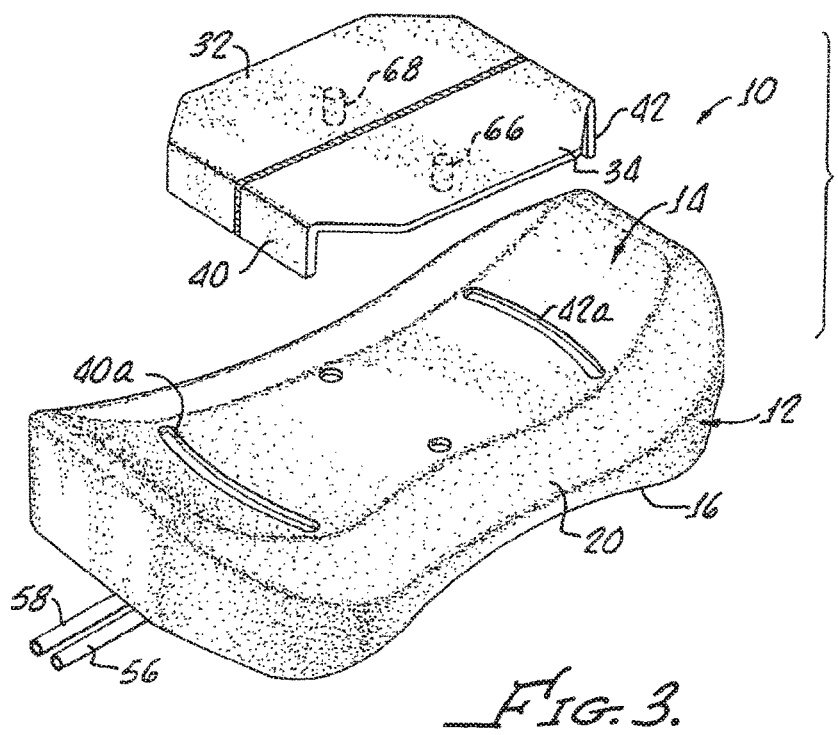
FIG. 3 is an exploded view of the device more clearly showing the disposition of the bladders on a relatively flat portion of the frame top side along with lines for coupling with the bladders to enable inflation thereof independently by the pumps.
Figure 4:
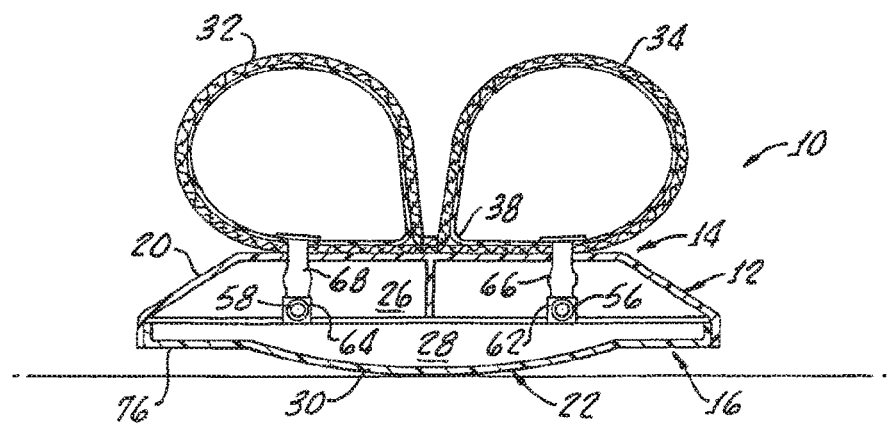
FIG. 4 is a cross sectional view of the device in accordance with the present invention taken along the line 4-4 of FIG. 1.

As best seen in FIGS. 1 and 3-4, the top surface 14 includes a first arched surface, or projection, 20 and, as best seen in FIG. 2 the bottom surface 16 includes an arched projection 22. The frame 12, which includes the top and bottom surfaces 14, 16 and arched projections 20, 22 is preferably molded from a suitable plastic. This structure includes hollow portions 26, 28, see FIG. 4, for enabling the device 10 to be made in a lightweight fashion and also enable innerconnection with first and second bladders 32, 34 which are disposed proximate a center 38 of the frame top surface 14.

The bladders 32, 34 may be attached to the top surface 14 by any suitable manner, for example depending portions 40, 42 may be fitted through corresponding slots 40a, 42a and fastened in any suitable manner.

Figure 5:
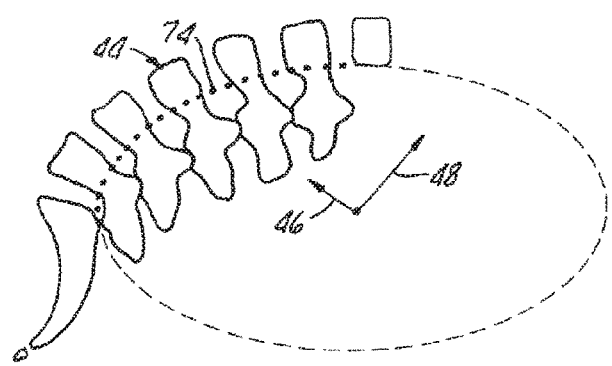
FIG. 5 is a diagram showing lumbar curvature as an 85° portion of an ellipse, this shape being the desired result of vectored forces provided by the bladders against the spine.

The first arch surface or projection 20 enables the first and second bladders 32, 34 to bear directly against the lower thoracic vertebrae of a users spine as illustrated in FIG. 5 by the arrows 46, 48. This vectored arrangement is described in U.S. Pat. No. 5,906,586 to Graham, which is hereby incorporated by reference herein in its entirety, describes suitable bladders for use with the present invention and their position.

The bladders 32, 34 may be attached to one another as indicated in the drawings or separate, however each is pneumatically individual from the other enabling separate inflation and deflation through the use of hand pumps, or bulbs, 52, 54 inner connected to the bladders 32, 34 respectively through lines 56, 58 and fittings 62, 64 coupled to bladder nipples 66, 68, see also FIG. 4.

Again with reference to FIG. 5, the first and second bladder bearing directions 46, 48 are divergent along a saggital plane of the user 72 in order to enhance an elliptical arch 74 shown in FIG. 5 which enhances an elliptical arch in the thoraco-lumbar/lumbosarra/spine 44.

Figure 6:
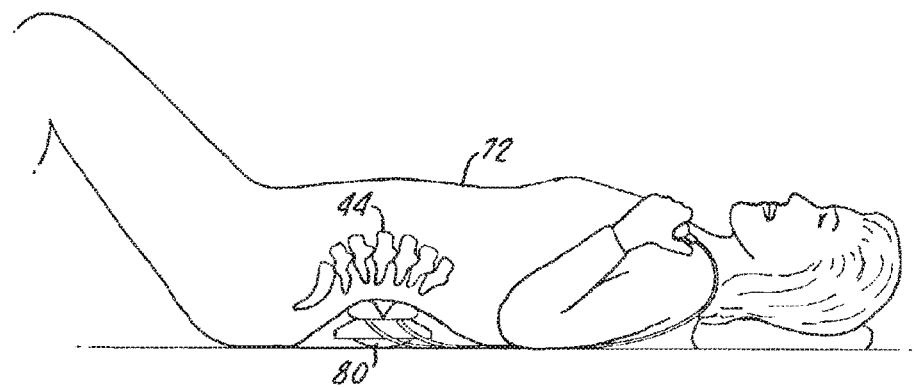
Figure 7:
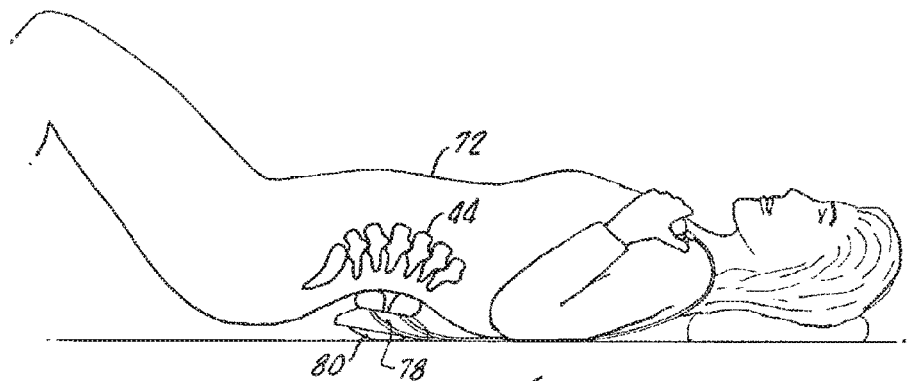

With specific reference to FIG. 4, the frame bottom surface 16 includes the arched projection 22 which is preferably surrounded by a flat portion 76. The second arched projection 22 is disposed on the bottom surface 16 for enabling the frame 12 and bladders 32, 34 to be rocked by the user 72 as illustrated in FIGS. 6-8 in a direction transverse to a longitudinal axis 78 of the frame 12. As hereinabove noted, the flat portion 76 provides a stop for the rocking action. Friction between the back of the user and the bladders 32 and 34 of the device 10 can cause forces to be applied to the spine of the user when the rocking action is stopped by the flat portion 76.

In operation, the rocking action enabled by the arcuate surface works the users abdominal and pelvic muscles while the spine is urged into an elliptical shape. The momentum of the rocking against the urged elliptical shape promotes stretching of the spine which in turn causes longitudinal alignment of the spinal vertebrae 44 and thus provides therapy for reinstating a lordotic arch in the spine as well as aligning the vertebrae along a longitudinal spinal axis. In some embodiments, an abdominal muscle and spine exercising device can be combined with one or more features for exercising the lower body muscles.

A spinal disc/joint, lower body, leg muscle, abdominal muscle and spine exercising device may generally include a frame and apparatus for redefining the curvature of the spine and exercising the lower body muscles. Specifically, the apparatus for manipulating and imparting curvature of the spine includes a frame for placement on a floor and having a top surface, along with one or more pads, cushions, pneumatic chambers, or inflatable bladders. In some embodiments, a first pad or inflatable bladder is disposed for directly bearing against lower thoracic and upper lumbar vertebrae of a user's spine in a first direction and a second pad or inflatable bladder is disposed for directly bearing against the mid-lumbar and lumbo-sacral vertebrae of the spine in a second direction. The adjacent pads, pneumatic chambers, inflated bladders, or alternately inflated bladders, provide diverging forces against the user's spine and thereby cause stretching and longitudinal aligning of the spinal vertebrae while promoting fluid imbibition throughout the vertebrae and discs. Thus the spinal vertebrae are urged into the natural elliptical alignment and the joints are lubricated and aligned. In some embodiments, a single pad, pneumatic chamber, or inflatable bladder is disposed on the frame 114. The single pad, pneumatic chamber, or inflatable bladder can bear against the lower thoracic and upper lumbar vertebrae of a user's spine in a first direction and/or the mid-lumbar and lumbo-sacral vertebrae of the spine in a second direction. An adjustable body strap attachment for encompassing the user's thoracic/lumbo-sacral-pelvic spinal vertebrae region and secured through the frame is attached to an elongate stirrup strap. The stirrup attachment engages slidably on the user's feet/legs for exercising pulling force aligned from the legs and lower body to the spine, thereby imparting decompression force from the lower body to the spine and the lower body muscles including the legs, are stretched and exercised. Additionally a hand held monitor for communicating with a tension gauge for measuring the decompression force exerted by the feet/legs on the lower body and spine may be disposed and integrally attached to the stirrup strap.

Figure 10:
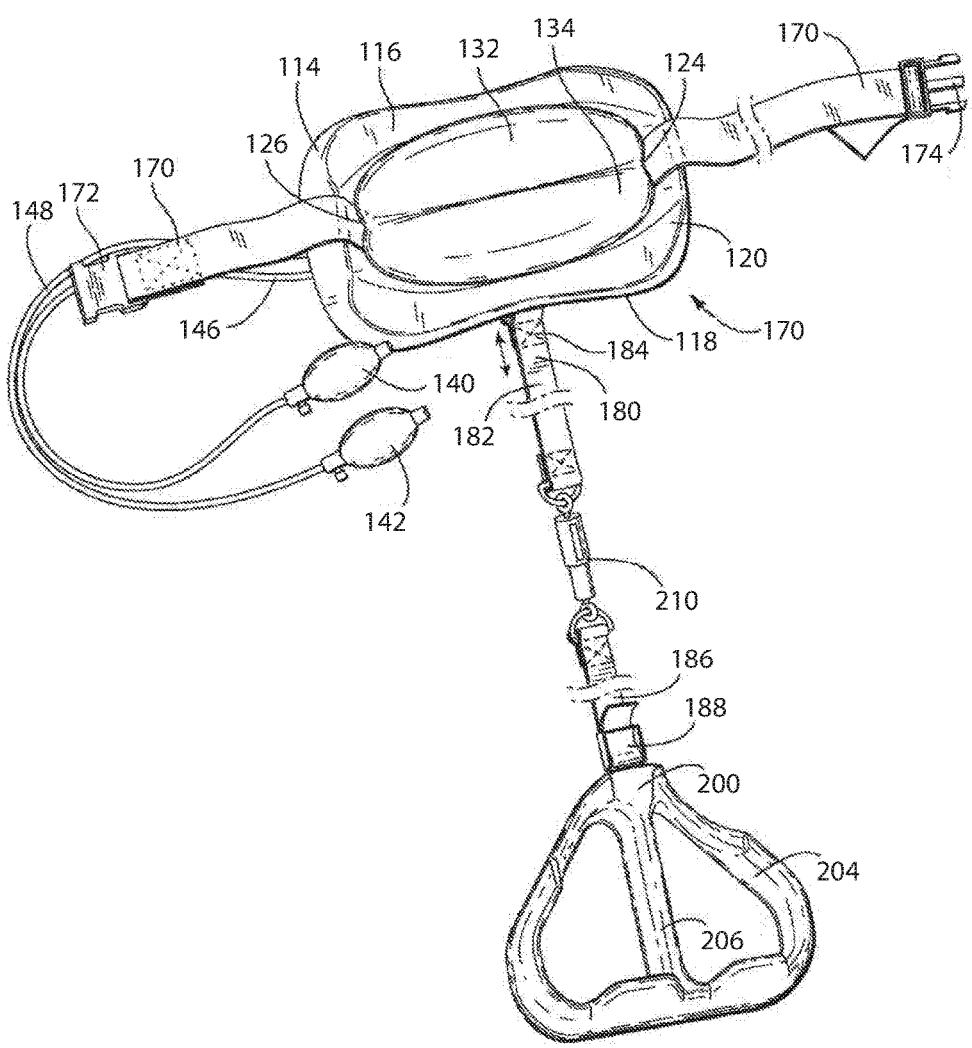
FIG. 10 illustrates a perspective view of the top side of the lower body and spinal exercise device positioned for use in accordance with FIG. 9.
Figure 11:
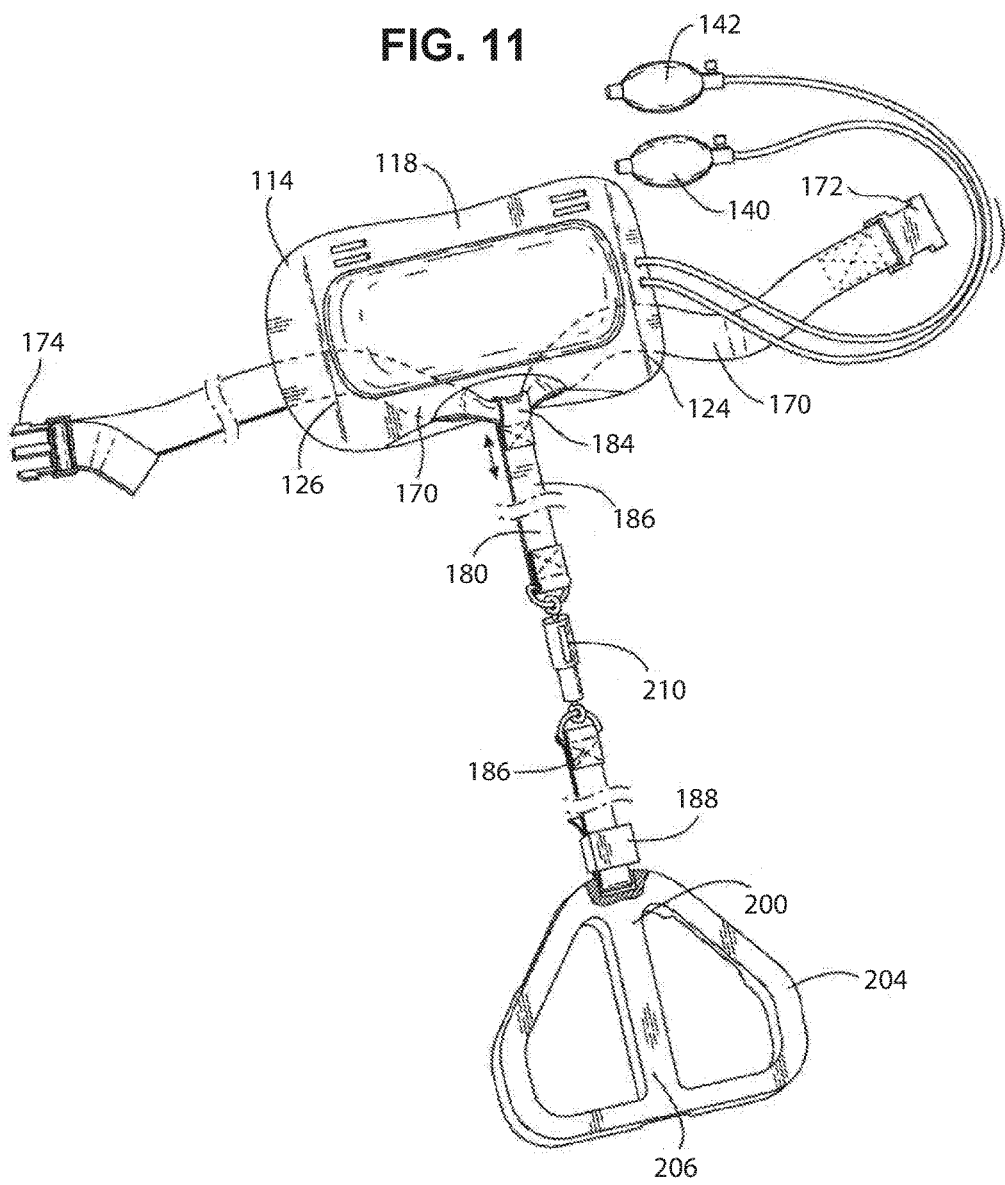
FIG. 11 illustrates a view of the bottom side of the lower body and spinal exercise device positioned for use in accordance with FIG. 9.
Figure 12:
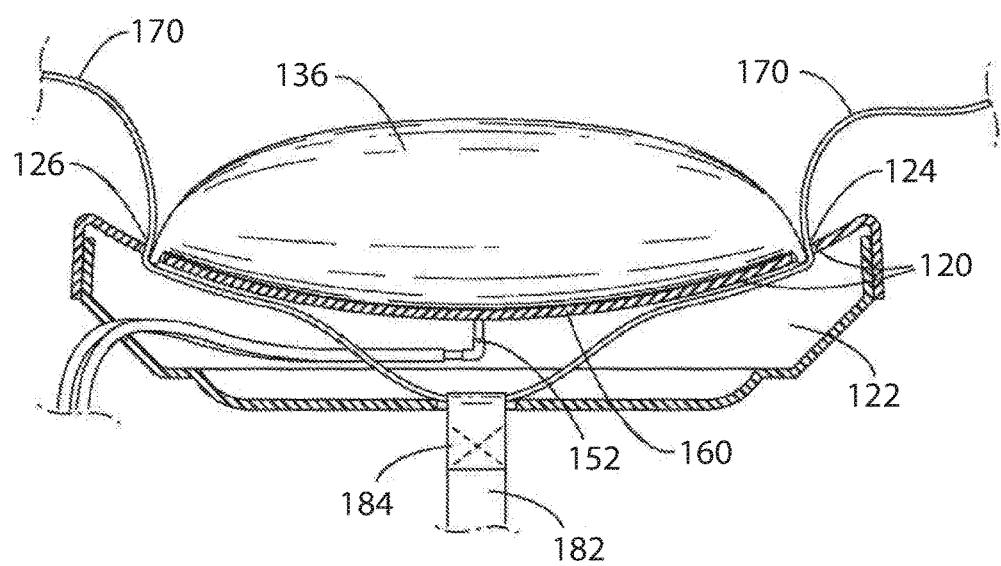
FIG. 12 is a cross sectional view of the device in accordance with the invention showing the inflatable bladder disposed on a frame, connected to flexible pump tubing, hollow and slot portions of the frame, and a body strap attachment interconnected to the frame slots and to the elongate stirrup strap.

With reference to FIGS. 9-12 there is shown a leg muscle, abdominal muscle, and spinal exercise device 110 which includes a frame 114 having a top surface 116 and a bottom surface 118. As best seen in FIGS. 9 and 12, the top surface 116 includes a concave surface 120 and, as best seen in FIG. 11 a bottom surface 118.

The frame 114 structure is preferably molded in suitable lightweight plastic for enabling interconnection of the two inflatable bladders 132, 134 to the top surface 116. As best seen in FIG. 12, the concave surface 120 of the frame 114 includes a hollow portion 122 and slotted 124, 126 portions for enabling interconnection the air bladders 132, 134 and interconnection of the body strap attachment 170.

With reference to FIG. 10, the inflatable bladders 132, 134 carried by the frame 114 are defined by an upper 132 and a lower portion 134 which are disposed proximate a center of the frame top surface 116. With reference to FIGS. 10 and 12, the air bladders 132, 134 are pneumatically inflated and deflated through the use of hand held pumps 140, 142 or bulbs, respectively through flexible tubing 146, 148 lines and fittings 152, 154 coupled to the bladders 132, 134 on the frame top surface underside 160. In some embodiments, a single hand held pump or bulb may inflate both air bladders 132, 134.

Figure 15:
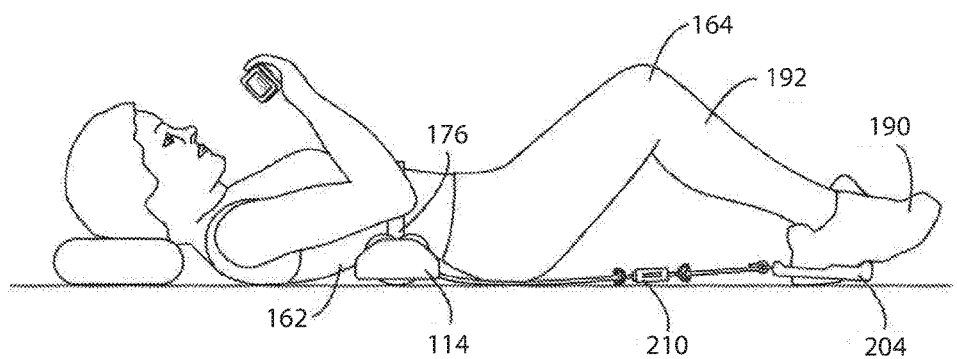
FIGS. 15-16 illustrate the use of the lower elongate stirrup strap member including an optionally attachable tension gauge for measuring the decompression force and a handheld monitor for communication with the tension gauge.
Figure 16:
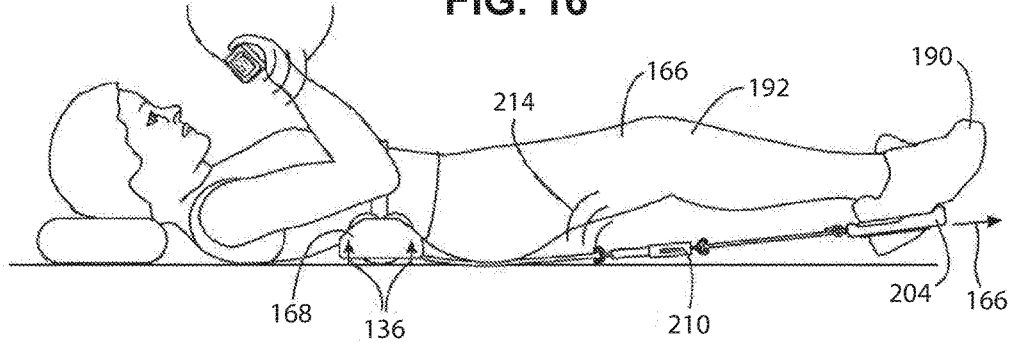

As illustrated in FIGS. 15 and 16, the inflatable bladders 132, 134 disposed on the frame concave top surface 116 bear directly against the user's spine while frame 114 supports the user's body contour 162. FIG. 15 shows the user at rest in an aligned position for exercise. FIG. 16 shows the user applying longitudinal alignment force 166 and enhanced spinal arc 168 created upon inflation 136 of the upper bladder 132 bearing against the lower thoracic and upper lumbar vertebrae and upon inflation of a lower bladder 134 bearing against the middle lumbar and lumbo-sacral vertebrae. The arrangement of the frame 114 and bladders 132, 134 is described in U.S. Pat. Nos. 5,906,586 and 7,060,085 to Graham, each of which is hereby incorporated by reference herein in its entirety, describe suitable bladders for use with the present invention and their position.

The bottom surface 118 of the frame 114 can be shaped or otherwise configured to allow for a rocking motion as described herein with respect to FIGS. 1-8. In operation, the rocking action enabled by the arcuate surface works the users abdominal and pelvic muscles while the spine is urged into an elliptical shape. The momentum of the rocking against the urged elliptical shape promotes stretching of the spine which in turn causes longitudinal alignment of the spinal vertebrae and thus provides therapy for reinstating a lordotic arch in the spine as well as aligning the vertebrae along a longitudinal spinal axis. The inflatable bladders 132 and 134 may be inflated to bear directly against the lower thoracic vertebrae of a users spine to apply additional forces to the spine. Friction between the back of the user and the bladders 132 and 134 can cause forces to be applied to the spine of the user when the rocking action is stopped by contact between a section of the frame 114 and a surface upon which the frame is positioned, as described above, for example, with respect to flat portion 76 of device 10.

As seen in FIGS. 9-12, a body strap attachment 170 may be fitted through corresponding slots 124, 126 in the top surface 116 of the frame and fastened in a suitable manner. Two ends of the body strap attachment 170, shown in FIGS. 9-11, may include a buckle 172 on one end and a buckle fitting 174 on the other end for adjustably securing the body strap 170 and the frame 114 to the contour of the user's waist/lumbar spinal region 162, In an alternative embodiment depicted in FIGS. 13 and 14, the user may detach the frame 114 and use the body strap attachment 170 without the frame 114 or inflatable bladders 132, 134.

With reference to FIGS. 9, 13 and 14, there is shown an elongate stirrup strap member 180 having a proximal end 182 and a distal end 186. Both ends of the elongate stirrup strap member 180 include at least one loop for fastening the proximal end 182 to the body strap attachment 170 and another loop for fastening the adjustable distal end 188 to the stirrup 178. As best seen in FIG. 11 the elongate stirrup strap member 180 includes at least one loop 184 for fastening the proximal end 182 to the body strap attachment and is engaged with the bottom surface of the frame 118. FIG. 13 illustrates a stirrup 200 as a slidably looped band 202 attached to the loop stirrup strap distal end 188. FIG. 14 illustrates the stirrup 200 as annulus 204 attached to the adjustable stirrup strap distal end 188. As best seen in FIG. 16, the annulus 204 stirrup is shown with a partition 206 and a support for each foot 190 which aligns each leg 192 with the pelvis and spine while applying decompression force 194 to the spine.

With specific reference to FIGS. 15-16, in an alternative embodiment, a removable tension gauge 210 is coupled to the stirrup strap 280. A handheld monitor 212 communicates 214 with the tension gauge 210 thereby enabling the user to simultaneously view the tension measurement on the handheld monitor 212 while applying decompression tension force 194 from the feet 190 and legs 192 to the spine. The tension gauge 210 and handheld monitor 212 enabling the user to simultaneously view the tension measurement may be of a conventional design. FIG. 15 illustrates the user in a relaxed longitudinal aligned 164 position and FIG. 16 illustrates the user in the extended lower body position applying decompression force 194 to the spine and applying longitudinal stretching force 166 with inflated bladders 132, 134 against the spine.

Figure 17:
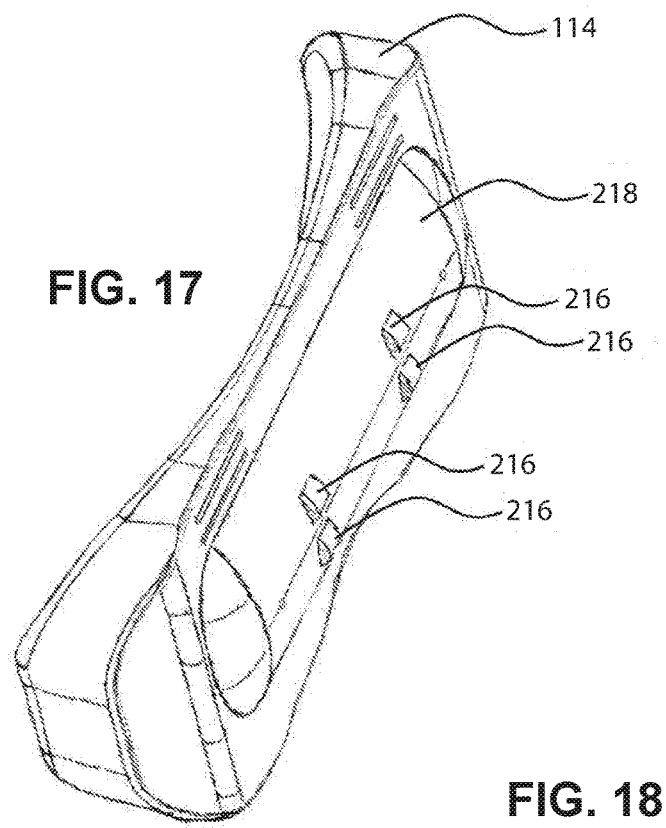
FIG. 17 is a perspective view of an exemplary frame with wheels.

With specific reference to FIG. 17 there is shown an embodiment of a frame 114 having plurality of wheels 216 rotatably attached along the bottom surface 118. The wheels 216 help to allow the frame 114 to move easily when it is used upon a hard surface, such as tile, concrete or wood. The wheels 216 are recessed into the frame 114 such that only a portion of the wheels 216 extend beyond the bottom surface 118. This helps to allow the frame 114 to still work properly on non-hard surfaces such as carpet. The plurality of wheels 216 can be at least one wheel, but is also understood to range from one wheel to many wheels.

Figure 18:
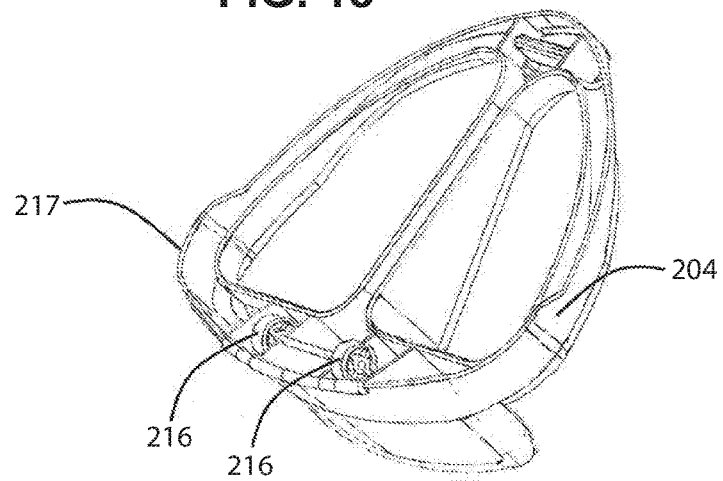
FIG. 18 is a perspective view of an exemplary stirrup with wheels.

With specific reference to FIG. 18 there is shown a stirrup 204 that now also includes a plurality of wheels 216. Just as with the frame 114 of FIG. 17, the wheels 216 of FIG. 18 allow the stirrup 204 to move easily when it is used upon a hard surface, such as tile, concrete or wood. Again, the wheels 216 can be recessed into the stirrup such that only a small portion of the wheels 216 extend beyond a bottom surface 217 of the stirrup 204. The plurality of wheels 216 can be at least one wheel, but is also understood to range from one wheel to many wheels.

Figure 19:
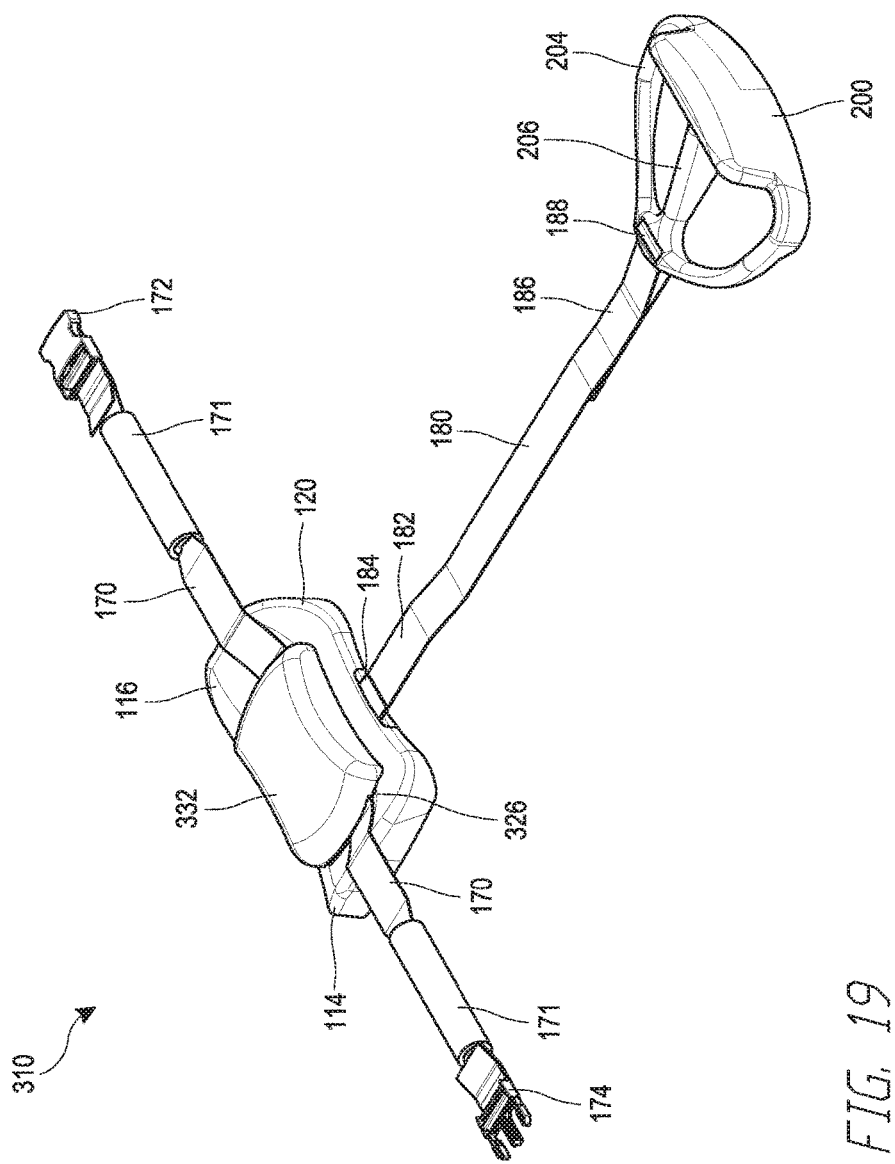
FIG. 19 is a perspective view of the lower body and spinal exercise device in accordance with the present invention, including a frame having a pad disposed thereon, a body attachment, a stirrup strap, and an attached stirrup for feet/legs.
Figure 20:
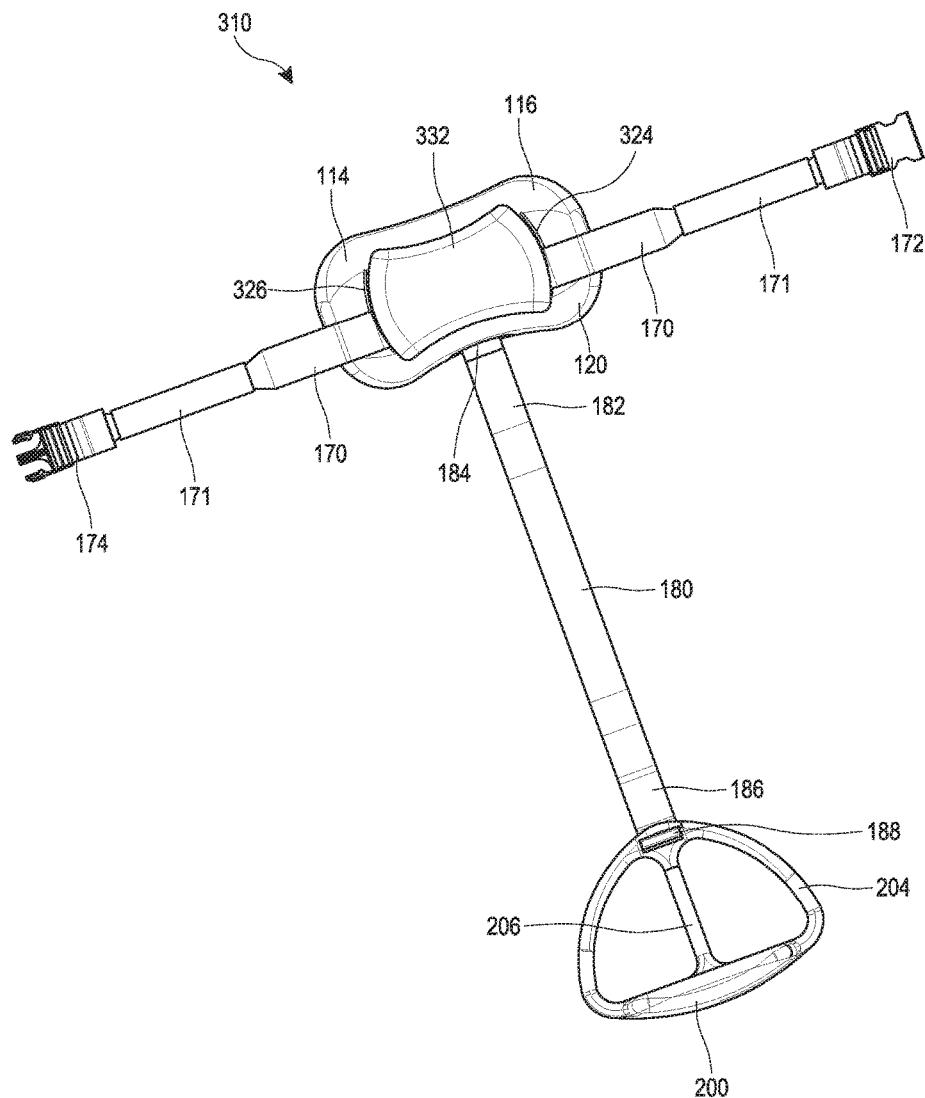
FIG. 20 illustrates a perspective view of the top side of the lower body and spinal exercise device positioned for use in accordance with FIG. 19.
Figure 21:
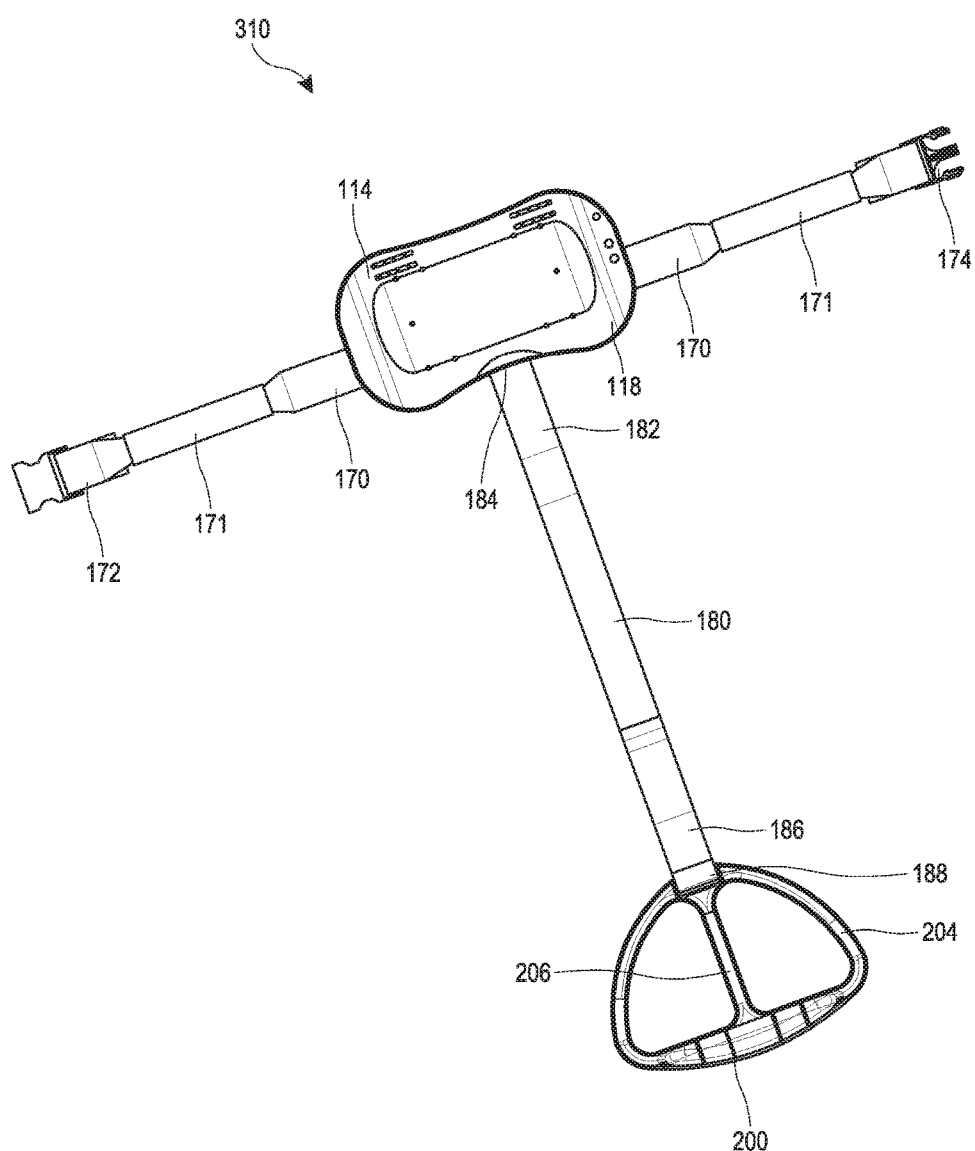
FIG. 21 illustrates a view of the bottom side of the lower body and spinal exercise device positioned for use in accordance with FIG. 19.
Figure 22:
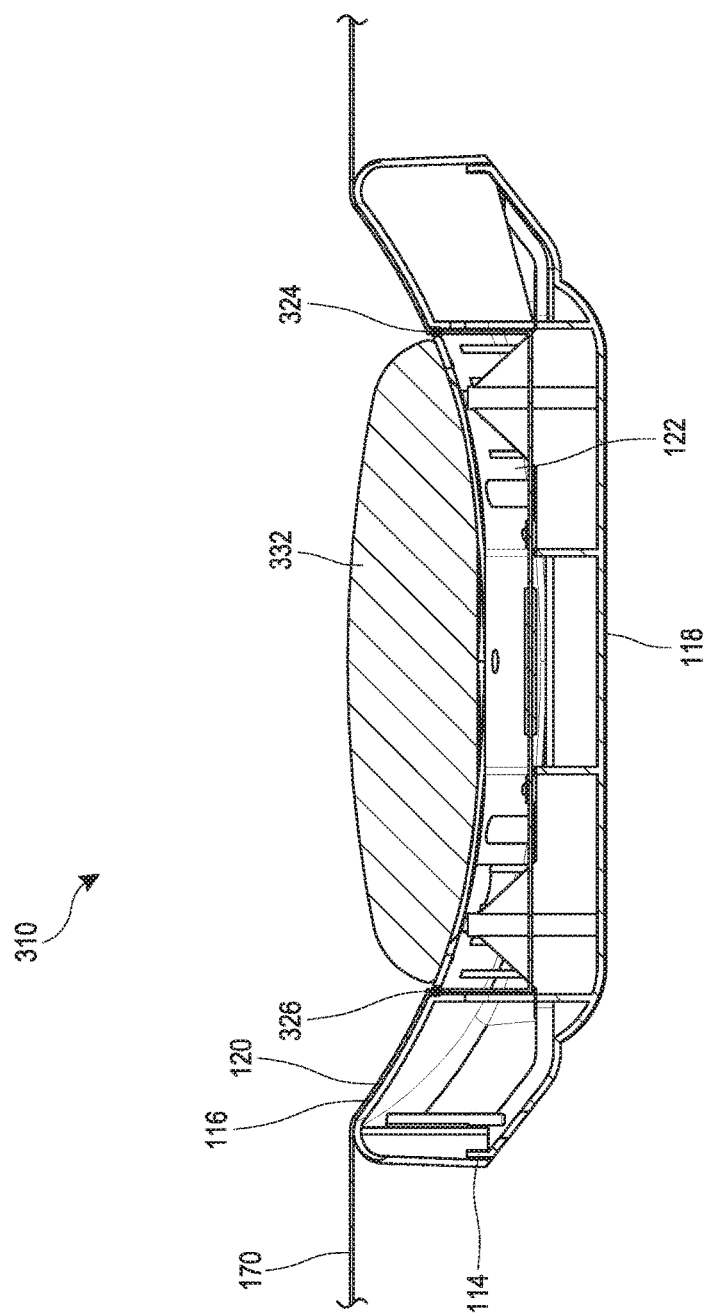
FIG. 22 is a cross sectional view of the device in accordance with the invention showing a pad disposed on a frame and the body strap positioned between the frame and the pad.

With reference to FIGS. 19-22 there is shown a leg muscle, abdominal muscle, and spinal exercise device 310 which includes a frame 114 having a top surface 116 and a bottom surface 118. As best seen in FIGS. 19 and 22, the top surface 116 includes a concave surface 120 and, as best seen in FIG. 21 a bottom surface 118.

The frame 114 structure is preferably molded in suitable lightweight plastic for enabling interconnection of a pad or cushion 332 to the top surface 116. As best seen in FIG. 22, a hollow portion 122 and slotted portions 324 and 326 can enable passage of the body strap attachment 170 through the frame 114.

The exercise device 310 can be used in the same or similar manner as described with respect to the exercise device 110, for example, in the same or similar manner as described with respect to FIGS. 15 and 16. In use, the pad 332 disposed on the frame concave top surface 116 bear directly against the user's spine while frame 114 supports the user's body contour 162. The user can apply longitudinal alignment force 166 and an enhanced spinal arc 168 can be created by an upper portion of the pad 332 bearing against the lower thoracic and upper lumbar vertebrae and a lower portion of the lower portion of the pad 332 bearing against the middle lumbar and lumbo-sacral vertebrae.

In certain embodiments, the pad 332 can be formed of or filled with one or more foam materials. The foam materials can be open cell foam materials or closed cell foam materials. In certain embodiments, the pad 332 may be formed of one or more elastic or viscoelastic materials. In certain embodiments, the pad 332 can be formed of or filled with one or more of polyester, polyether, polystyrene, polyurethane, polyethylene and vinyl, or any other suitable polymer based material. In certain embodiments, the pad 332 may be generally rigid. In other embodiments, the pad 332 may be flexible or deformable.

In certain embodiments, the material of the pad 332 can have a density between 0.5 lb/ft$^3$ to 15 lb/ft$^3$. In certain embodiments, the pad 332 can have a density between 1.5 lb/ft$^3$ to 10 lb/ft$^3$. In certain embodiments, the pad 332 can have a density between 3 lb/ft$^3$ to 8 lb/ft$^3$. In certain embodiments, the pad 332 can have a density of less than 1 lb/ft$^3$, less than 2 lb/ft$^3$, less than 3 lb/ft$^3$, less than 4 lb/ft$^3$, less than 5 lb/ft$^3$, less than 6 lb/ft$^3$, less than 7 lb/ft$^3$, less than 8 lb/ft$^3$, less than 9 lb/ft$^3$, less than 10 lb/ft$^3$, less than 11 lb/ft$^3$, less than 12 lb/ft$^3$, less than 13 lb/ft$^3$, less than 14 lb/ft$^3$, or less than 15 lb/ft$^3$. In certain embodiments, the pad 332 can have a density of more than 1 lb/ft$^3$, more than 2 lb/ft$^3$, more than 3 lb/ft$^3$, more than 4 lb/ft$^3$, more than 5 lb/ft$^3$, more than 6 lb/ft$^3$, more than 7 lb/ft$^3$, more than 8 lb/ft$^3$, more than 9 lb/ft$^3$, more than 10 lb/ft$^3$, more than 11 lb/ft$^3$, more than 12 lb/ft$^3$, more than 13 lb/ft$^3$, more than 14 lb/ft$^3$, or more than 15 lb/ft$^3$.

In certain embodiments, the pad 332 can be compressed to between 10% to 90% of its thickness, between 20% to 80% of its thickness, between 30% to 70% of its thickness, or between 40% to 60% of its thickness. In certain embodiments, the pad 332 can be compressed to less than 10% of its thickness, less than 20% of its thickness, less than 30% of its thickness, less than 40% of its thickness, less than 50% of its thickness, less than 60% of its thickness, less than 70% of its thickness, less than 80% of its thickness, or less than 90% of its thickness. In certain embodiments, the pad 332 can be compressed to more than 10% of its thickness, more than 20% of its thickness, more than 30% of its thickness, more than 40% of its thickness, more than 50% of its thickness, more than 60% of its thickness, more than 70% of its thickness, more than 80% of its thickness, or more than 90% of its thickness In certain embodiments, the material of the pad 332 can have a 25% indentation force-deflection measurement between 25 N to 200 N, between 50 N to 175 N, between 75 N to 150 N, or between 100 N to 125 N. In certain embodiments, the material of the pad 332 can have a 25% indentation force-deflection measurement of less than 25 N, less than 50 N, less than 75 N, less than 100 N, less than 125 N, less than 150 N, less than 175 N, or less than 200 N. In certain embodiments, the material of the pad 332 can have a 25% indentation force-deflection measurement of more than 25 N, more than 50 N, more than 75 N, more than 100 N, more than 125 N, more than 150 N, more than 175 N, or more than 200 N.

In certain embodiments, a pad 332 may be selected from a plurality of pads for use in the exercise device. For example, a pad 332 may be selected from a plurality of pads having different deformation properties. In some embodiments, a pad 332 having a relatively lower degree of deformability may provide improved force distribution to a user during use of the exercise device 310 in comparison to a pad having a relatively higher degree of deformability. In some embodiments, a pad 332 having a relatively higher degree of deformability may provide improved comfort to a user in comparison to a pad having a relatively lower degree of deformability.

As shown in FIGS. 19-22, the pad 332 is non-inflatable. The pad 332 can have a non-adjustable volume. In alternative embodiments, the exercise device 310 may include an inflatable bladder instead of a pad 332.

The bottom surface 118 of the frame 114 can be shaped or otherwise configured to allow for a rocking motion as described herein with respect to FIGS. 1-8. In operation, the rocking action enabled by the arcuate surface works the users abdominal and pelvic muscles while the spine is urged into an elliptical shape. The momentum of the rocking against the urged elliptical shape promotes stretching of the spine which in turn causes longitudinal alignment of the spinal vertebrae and thus provides therapy for reinstating a lordotic arch in the spine as well as aligning the vertebrae along a longitudinal spinal axis. Friction between the back of the user and the pad 332 can cause forces to be applied to the spine of the user when the rocking action is stopped by contact between a section of the frame 114 and a surface upon which the frame is positioned, as described above, for example, with respect to flat portion 76 of device 10. In certain embodiments, the pad 332 can be shapes, sized, or otherwise configured to maintain a desired position of the back during rocking or to impart a desired force to the back during rocking. Through the above-described rocking motion, therapy can be provided without requiring inflation of a bladder. Such embodiments may be advantageous for people with disabilities that prevent or restrict operation of a hand pump.

As seen in FIGS. 19-22, a body strap attachment 170 may be fitted through corresponding slots 324, 326 in the top surface 116 of the frame 114 and fastened in a suitable manner. In some embodiments, the body strap attachment 170 can pass through the frame 114 in a non-fixed relationship. Two ends of the body strap attachment 170, shown in FIGS. 19-21, may include a buckle 172 on one end and a buckle fitting 174 on the other end for adjustably securing the body strap 170 and the frame 114 to the contour of the user's waist/lumbar spinal region 162. In some embodiments, tubes 171 may be positioned over portions of the body strap 170.

With reference to FIGS. 19-21, there is shown an elongate stirrup strap member 180 having a proximal end 182 and a distal end 186. The distal end 186 of the elongate stirrup strap member 180 includes at least one loop for fastening the adjustable distal end portion 188 to the stirrup 200. The elongate stirrup strap member 180 also includes at least one loop 184 for fastening the proximal end 182 to the body strap attachment 170. A portion of the proximal end 182 can extend into the frame 114 through a slot 185 for coupling with the body strap attachment 170. FIGS. 19-21 illustrate the stirrup 200 as annulus 204 attached to the adjustable stirrup strap distal end portion 188. As best seen in FIG. 20, the annulus 204 stirrup is shown with a partition 206 and a support for each foot 190 which aligns each leg 192 with the pelvis and spine while applying decompression force 194 to the spine.

Figure 23:
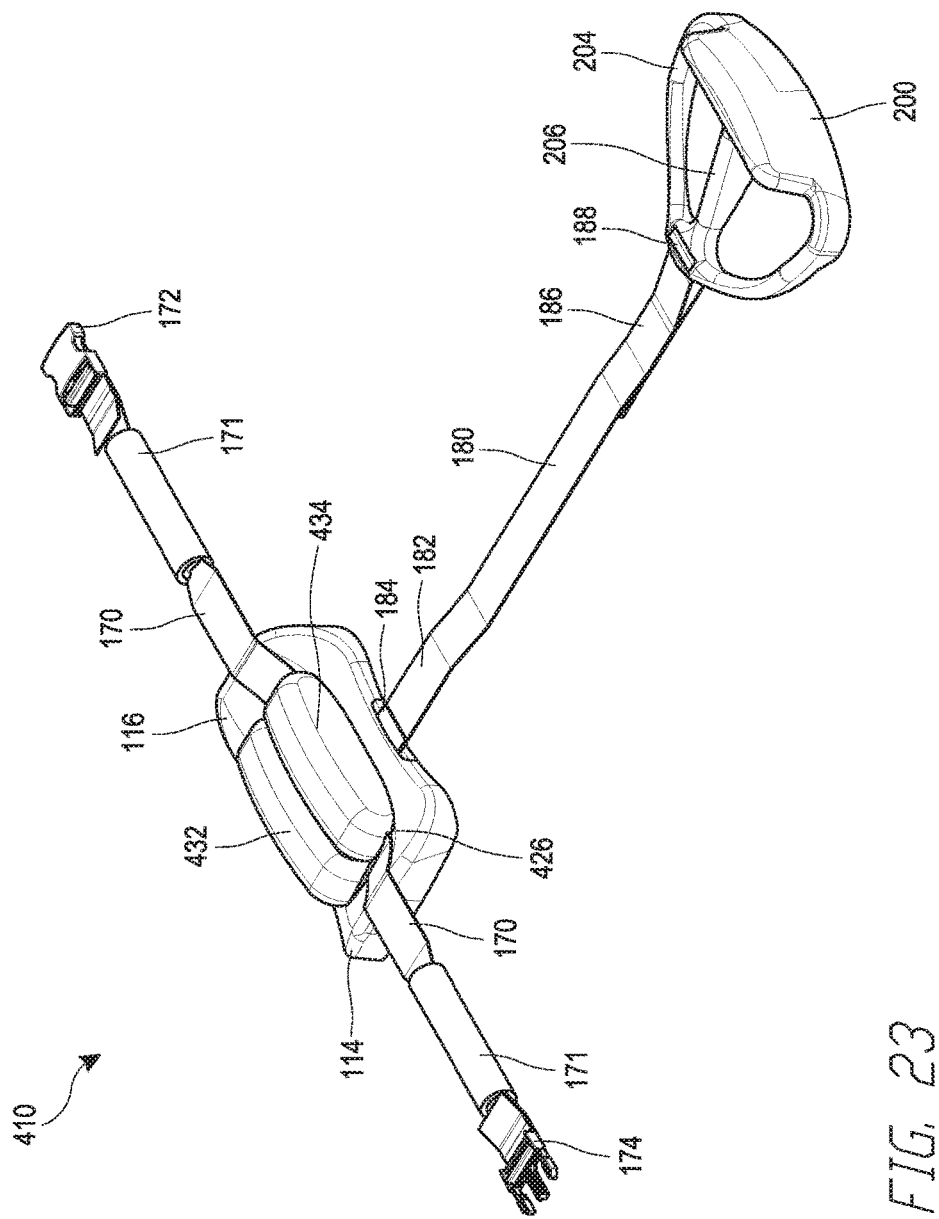
FIG. 23 is a perspective view of the lower body and spinal exercise device in accordance with the present invention, including a frame having two pads disposed thereon, a body attachment, a stirrup strap, and an attached stirrup for feet/legs.
Figure 24:
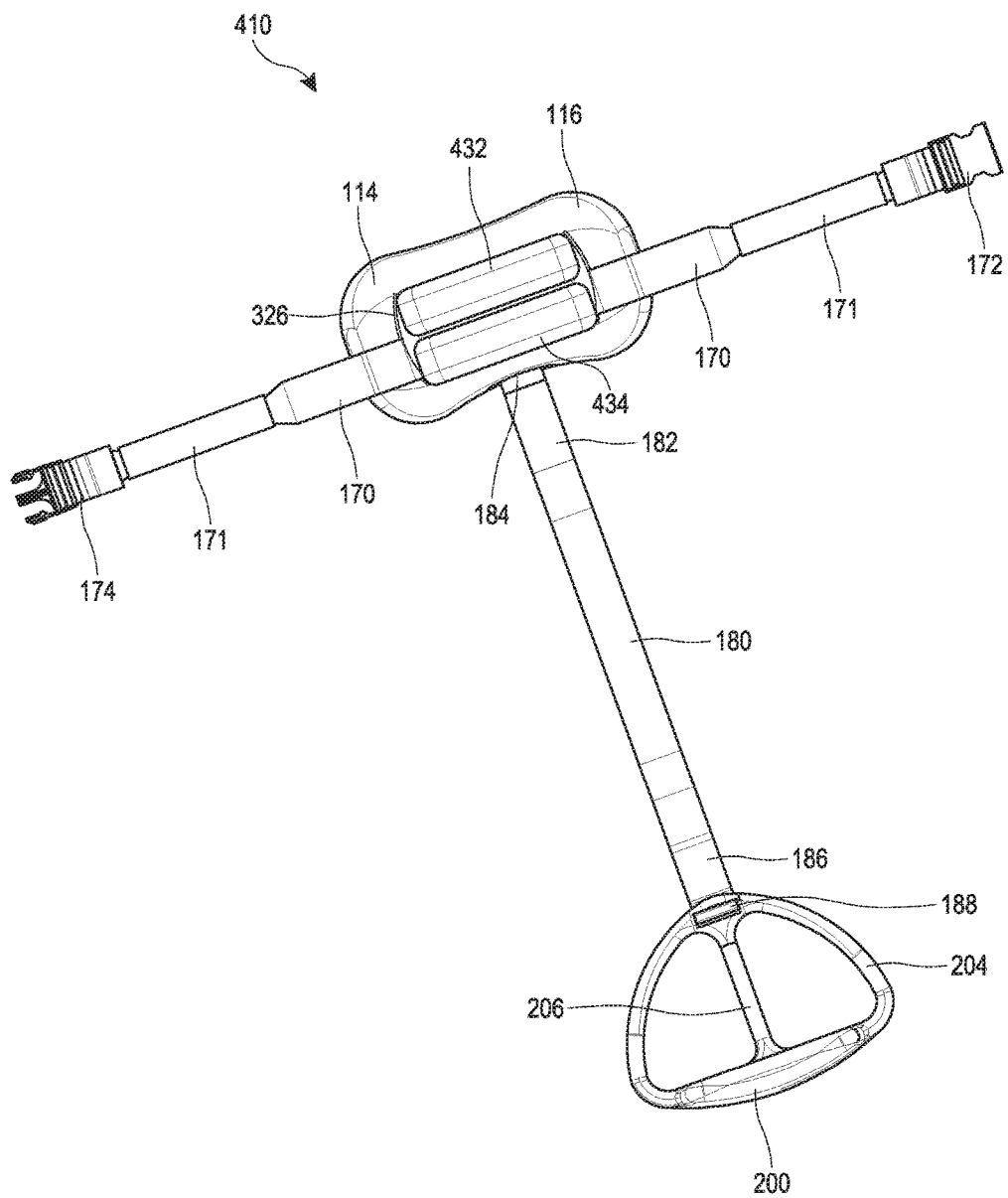
FIG. 24 illustrates a perspective view of the top side of the lower body and spinal exercise device positioned for use in accordance with FIG. 23.
Figure 25:
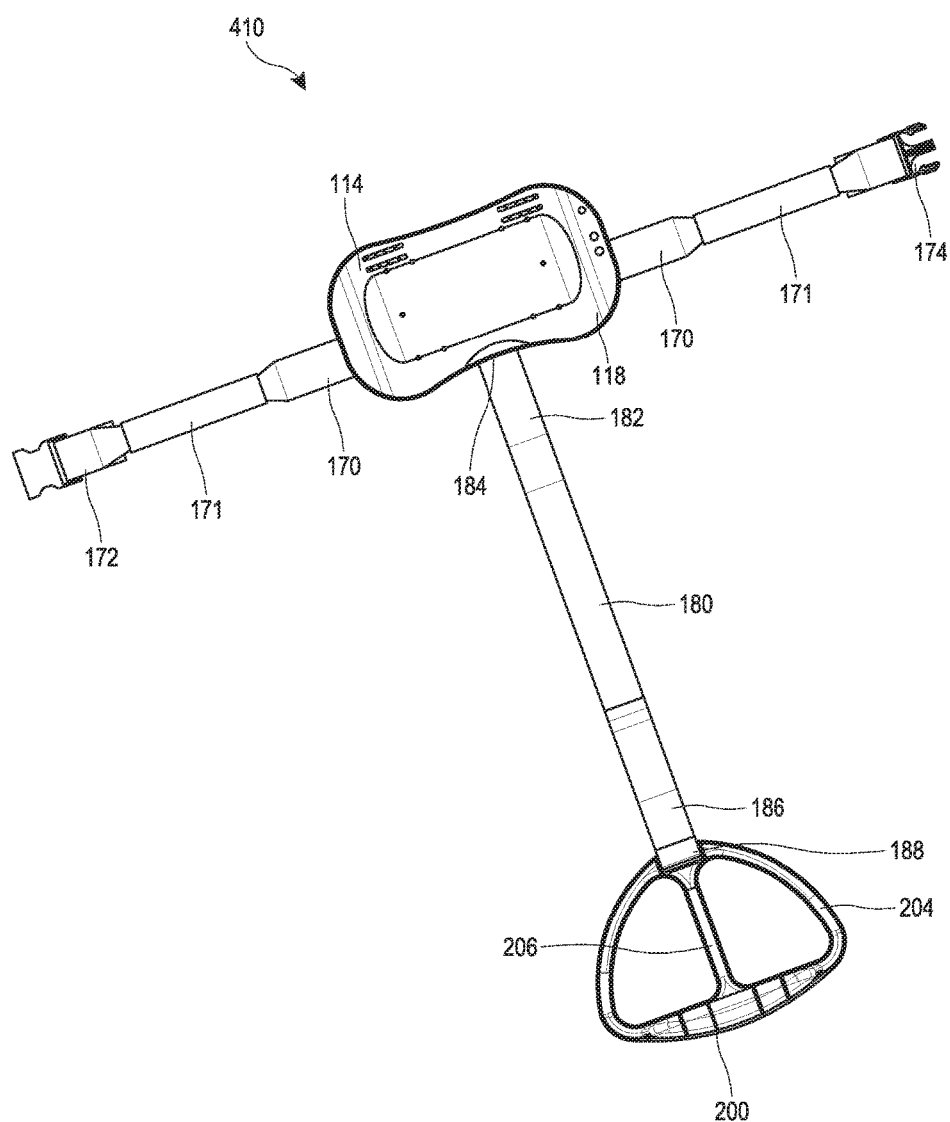
FIG. 25 illustrates a view of the bottom side of the lower body and spinal exercise device positioned for use in accordance with FIG. 23.
Figure 26:
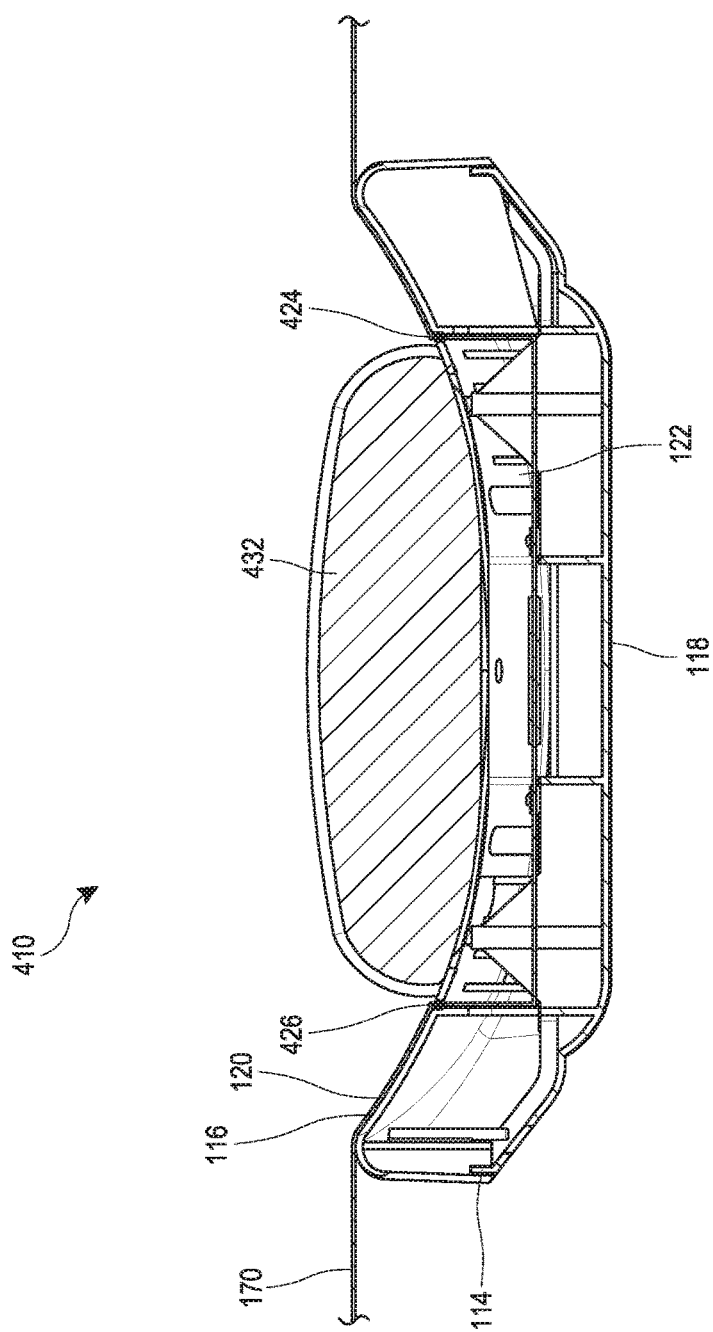
FIG. 26 is a cross sectional view of the device in accordance with the invention showing a pad disposed on a frame and the body strap positioned between the frame and the pad.
Figure 27:
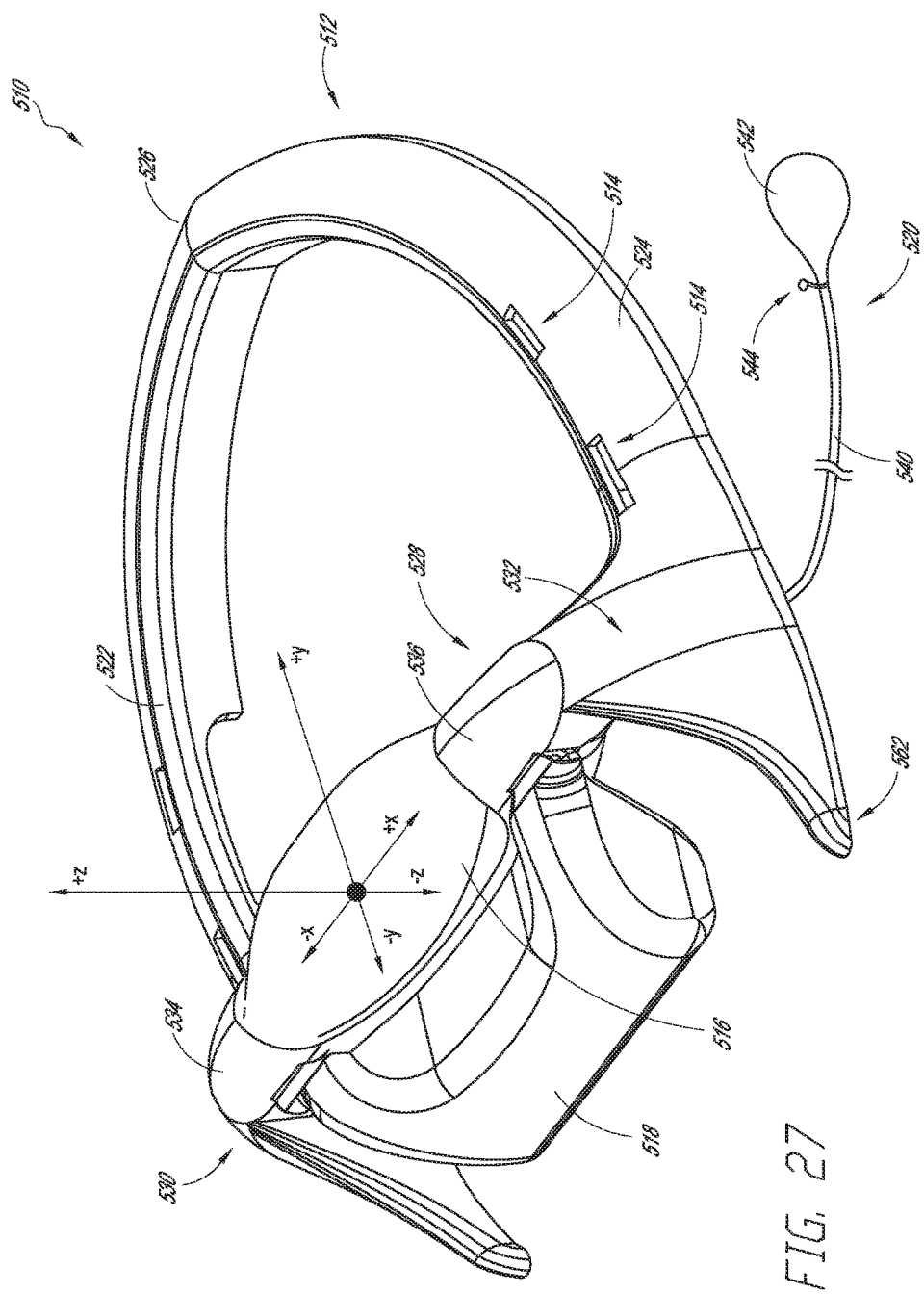
FIG. 27 is a perspective view of one embodiment of a decompression and traction system.
Figure 28:
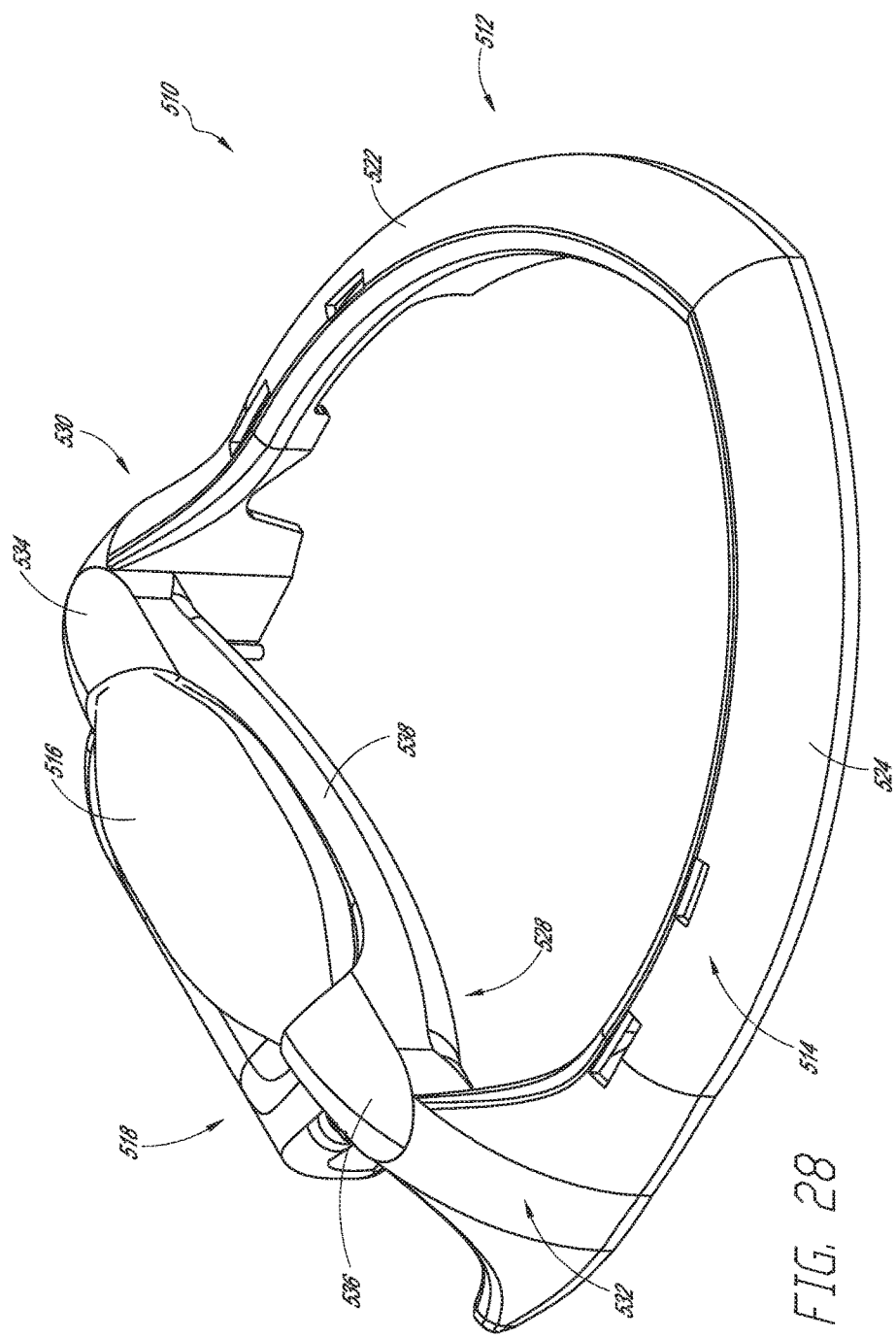
FIG. 28 is a perspective view of a portion of the system shown in FIG. 27.
Figure 29:
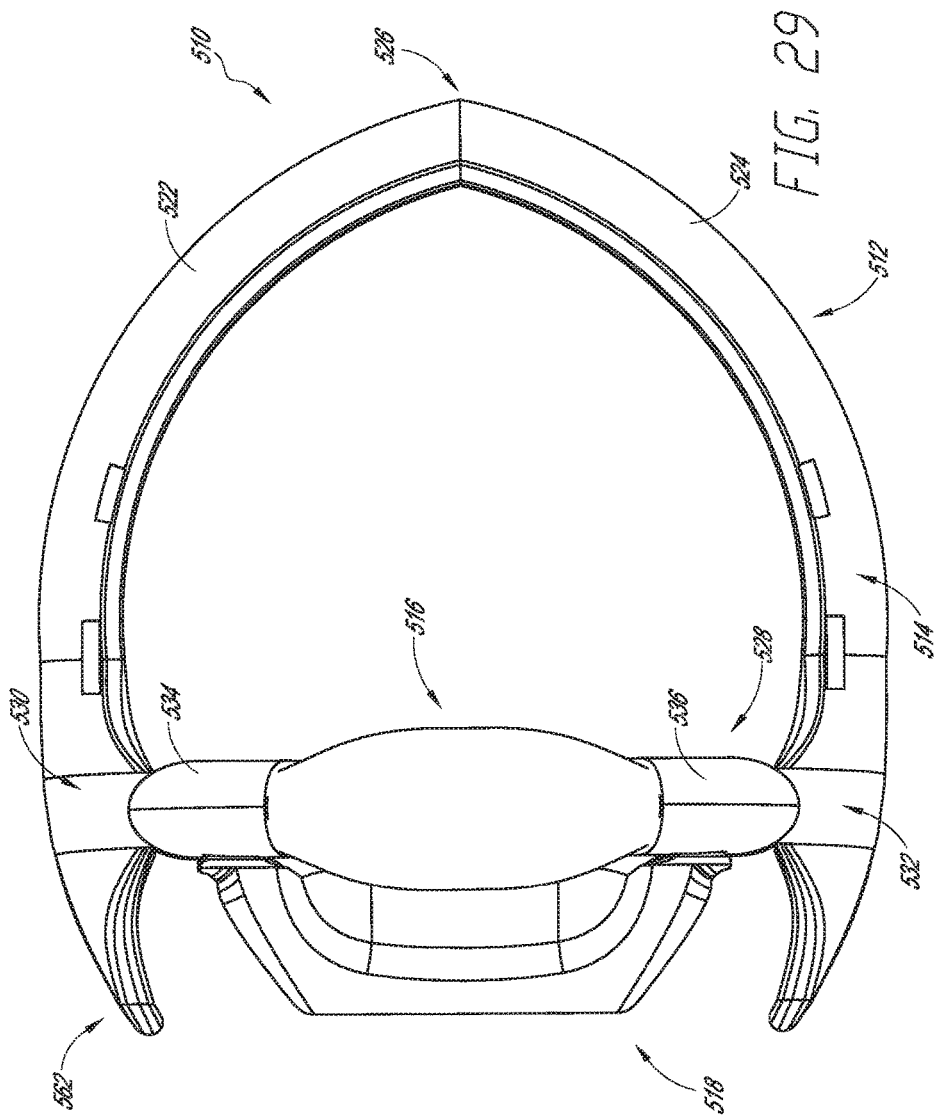
FIG. 29 is a top view of a portion of the system shown in FIG. 27.
Figure 30:
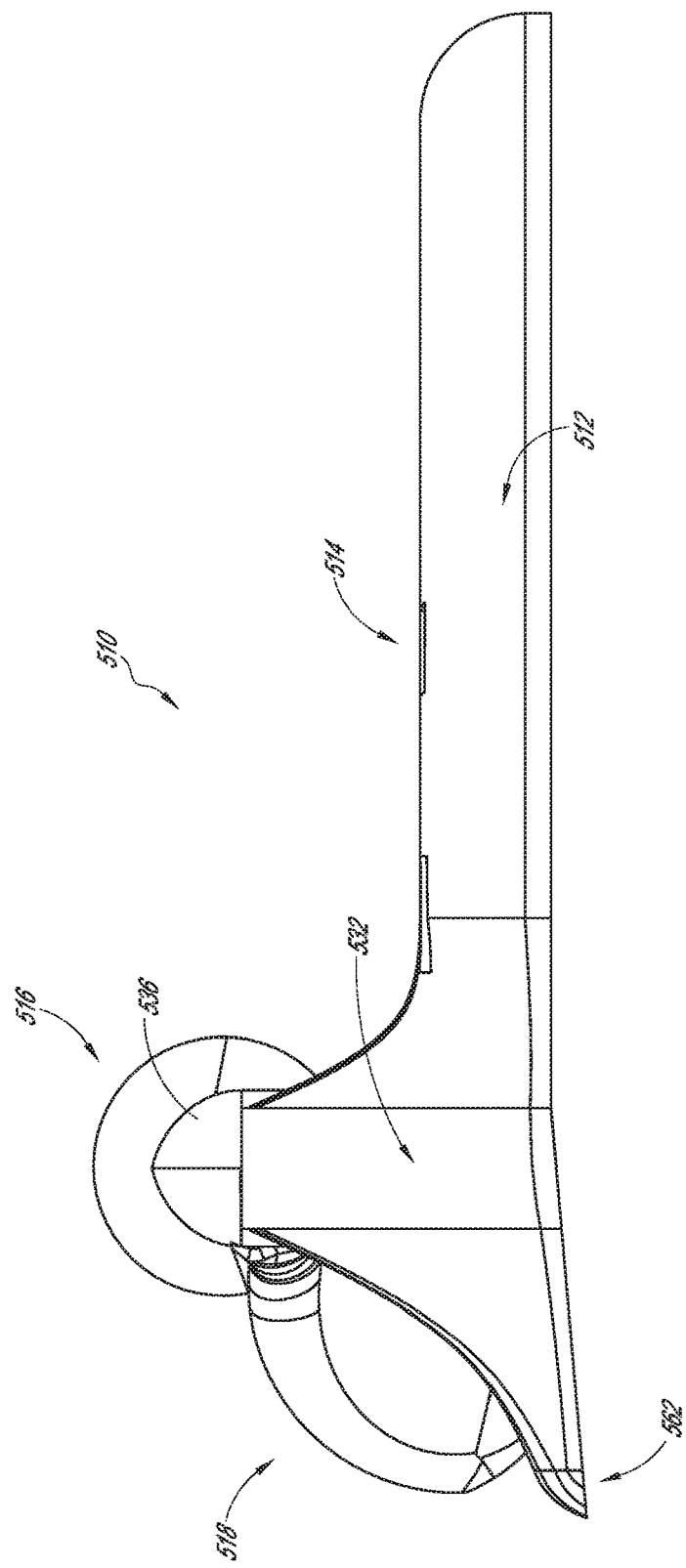
FIG. 30 is a side view of a portion of the system shown in FIG. 27.
Figure 31:
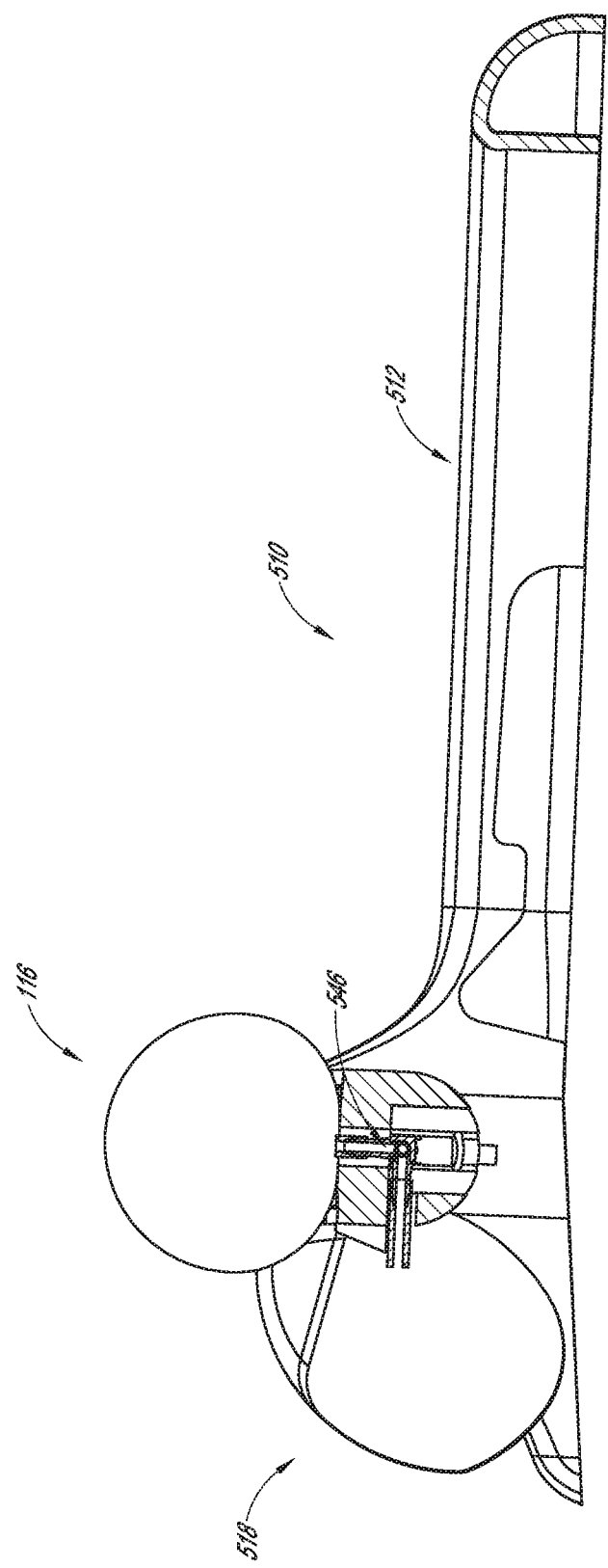
FIG. 31 is a cross-sectional side view of a portion of the system shown in FIG. 27.

With reference to FIGS. 23-26 there is shown a leg muscle, abdominal muscle, and spinal exercise device 410 which includes a frame 14 having a top surface 116 and a bottom surface 118. As best seen in FIGS. 23 and 26, the top surface 116 includes a concave surface 120 and, as best seen in FIG. 25 a bottom surface 118.

The frame 114 structure is preferably molded in suitable lightweight plastic for enabling interconnection of pads or cushions 432, 434 to the top surface 116. As best seen in FIG. 22, the concave surface 120 of the frame 114 includes a hollow portion 122 and slotted portions 424, 426 for enabling interconnection of the pads 432, 434 with the frame 114. Slotted portions 424 and 426 can also enable passage of the body strap attachment 170 through the frame 114.

The exercise device 410 can be used in the same or similar manner as described with respect to the exercise device 410, for example, in the same or similar manner as described with respect to FIGS. 15 and 16. In use, the pads 432, 434 disposed on the frame concave top surface 116 bear directly against the user's spine while frame 114 supports the user's body contour 162. The user can apply longitudinal alignment force 166 and an enhanced spinal arc 168 can be created by the upper pad 432 bearing against the lower thoracic and upper lumbar vertebrae and the lower pad 434 bearing against the middle lumbar and lumbo-sacral vertebrae.

In certain embodiments, the one or both of the pads 432 and 434 can be formed of or filled with one or more foam materials. The foam materials can be open cell foam materials or closed cell foam materials. In certain embodiments, one or both of the pads 432 and 434 may be formed of one or more elastic or viscoelastic materials. In certain embodiments, one or both of the pads 432 and 434 can be formed of or filled with one or more of polyester, polyether, polystyrene, polyurethane, polyethylene and vinyl, or any other suitable polymer based material. In certain embodiments, one or both of the pads 432 and 434 may be generally rigid. In other embodiments, one or both of the pads 432 and 434 may be flexible or deformable.

In certain embodiments, the material of one or both of the pads 432 and 434 can have a density between 0.5 $lb/ft^3$ to 15 $lb/ft^3$. In certain embodiments, one or both of the pads 432 and 434 can have a density between 1.5 $lb/ft^3$ to 10 $lb/ft^3$. In certain embodiments, one or both of the pads 432 and 434 can have a density between 3 $lb/ft^3$ to 8 $lb/ft^3$. In certain embodiments, one or both of the pads 432 and 434 can have a density of less than 1 $lb/ft^3$, less than 2 $lb/ft^3$, less than 3 $lb/ft^3$, less than 4 $lb/ft^3$, less than 5 $lb/ft^3$, less than 6 $lb/ft^3$, less than 7 $lb/ft^3$, less than 8 $lb/ft^3$, less than 9 $lb/ft^3$, less than 10 $lb/ft^3$, less than 11 $lb/ft^3$, less than 12 $lb/ft^3$, less than 13 $lb/ft^3$, less than 14 $lb/ft^3$, or less than 15 $lb/ft^3$. In certain embodiments, one or both of the pads 432 and 434 can have a density of more than 1 $lb/ft^3$, more than 2 $lb/ft^3$, more than 3 $lb/ft^3$, more than 4 $lb/ft^3$, more than 5 $lb/ft^3$, more than 6 $lb/ft^3$, more than 7 $lb/ft^3$, more than 8 $lb/ft^3$, more than 9 $lb/ft^3$, more than 10 $lb/ft^3$, more than 11 $lb/ft^3$, more than 12 $lb/ft^3$, more than 13 $lb/ft^3$, more than 14 $lb/ft^3$, or more than 15 $lb/ft^3$.

In certain embodiments, one or both of the pads 432 and 434 can be compressed to between 10% to 90% of its thickness, between 20% to 80% of its thickness, between 30% to 70% of its thickness, or between 40% to 60% of its thickness. In certain embodiments, one or both of the pads 432 and 434 can be compressed to less than 10% of its thickness, less than 20% of its thickness, less than 30% of its thickness, less than 40% of its thickness, less than 50% of its thickness, less than 60% of its thickness, less than 70% of its thickness, less than 80% of its thickness, or less than 90% of its thickness. In certain embodiments, one or both of the pads 432 and 434 can be compressed to more than 10% of its thickness, more than 20% of its thickness, more than 30% of its thickness, more than 40% of its thickness, more than 50% of its thickness, more than 60% of its thickness, more than 70% of its thickness, more than 80% of its thickness, or more than 90% of its thickness In certain embodiments, the material of one or both of the pads 432 and 434 can have a 25% indentation force-deflection measurement between 25 N to 200 N, between 50 N to 175 N, between 75 N to 150 N, or between 100 N to 125 N. In certain embodiments, the material of one or both of the pads 432 and 434 can have a 25% indentation force-deflection measurement of less than 25 N, less than 50 N, less than 75 N, less than 100 N, less than 125 N, less than 150 N, less than 175 N, or less than 200 N. In certain embodiments, the material of one or both of the pads 432 and 434 can have a 25% indentation force-deflection measurement of more than 25 N, more than 50 N, more than 75

N, more than 100 N, more than 125 N, more than 150 N, more than 175 N, or more than 200 N.

In certain embodiments, one or both of the pads 432 and 434 may be selected from a plurality of pads for use in the exercise device. For example, one or both of the pads 432 and 434 may be selected from a plurality of pads having different deformation properties. In some embodiments, a pad 432 or 434 having a relatively lower degree of deformability may provide improved force distribution to a user during use of the exercise device 410 in comparison to a pad having a relatively higher degree of deformability. In some embodiments, a pad 432 or 434 having a relatively higher degree of deformability may provide improved comfort to a user in comparison to a pad having a relatively lower degree of deformability.

As shown in FIGS. 23-26, the pads 432 and 434 are non-inflatable. In certain embodiments, the pads 432 and 434 can each have a non-adjustable volume. In alternative embodiments, the exercise device 410 may include inflatable bladders instead of pads 432 and 434. In some embodiments, the exercise device 410 can include one of the pads 432 and 434 and an inflatable bladder. For example, the exercise device 410 can include a pad 432 and an inflatable bladder. The inflatable bladder may include any of the features and/or functions of the inflatable bladder 134. In other embodiments, the exercise device 410 can include a pad 434 and an inflatable bladder. The inflatable bladder can include any of the features and/or functions of the inflatable bladder 132.

The bottom surface 118 of the frame 114 can be shaped or otherwise configured to allow for a rocking motion as described herein with respect to FIGS. 1-8. In operation, the rocking action enabled by the arcuate surface works the users abdominal and pelvic muscles while the spine is urged into an elliptical shape. The momentum of the rocking against the urged elliptical shape promotes stretching of the spine which in turn causes longitudinal alignment of the spinal vertebrae and thus provides therapy for reinstating a lordotic arch in the spine as well as aligning the vertebrae along a longitudinal spinal axis. Friction between the back of the user and the pads 432 and 434 can cause forces to be applied to the spine of the user when the rocking action is stopped by contact between a section of the frame 114 and a surface upon which the frame is positioned, as described above, for example, with respect to flat portion 76 of device 10. In certain embodiments, the pads 432 and 434 can be shapes, sized, or otherwise configured to maintain a desired position of the back during rocking or to impart a desired force to the back during rocking. Through the above-described rocking motion, therapy can be provided without requiring inflation of a bladder. Such embodiments may be advantageous for people with disabilities that prevent or restrict operation of a hand pump. [0161] As seen in FIGS. 23-26, a body strap attachment 170 may be fitted through corresponding slots 424, 426 between the top surface 116 of the frame and fastened in a suitable manner. In some embodiments, the body strap attachment 170 can pass through the frame 114 in a non-fixed relationship. Two ends of the body strap attachment 170, shown in FIGS. 23-25, may include a buckle 172 on one end and a buckle fitting 174 on the other end for adjustably securing the body strap 170 and the frame 114 to the contour of the user's waist/lumbar spinal region 162. In some embodiments, tubes 171 may be positioned over portions of the body strap 170.

With reference to FIGS. 23-25, there is shown an elongate stirrup strap member 180 having a proximal end 182 and a distal end 186. The distal end 186 of the elongate stirrup strap member 180 includes at least one loop for fastening the adjustable distal end portion 188 to the stirrup 200. The elongate stirrup strap member 180 also includes at least one loop 184 for fastening the proximal end 182 to the body strap attachment 170. A portion of the proximal end 182 can extend into the frame 114 through a slot 185 for coupling with the body strap attachment 170. FIGS. 23-25 illustrate the stirrup 200 as annulus 204 attached to the adjustable stirrup strap distal end portion 188. As best seen in FIG. 24, the annulus 204 stirrup is shown with a partition 206 and a support for each foot 190 which aligns each leg 192 with the pelvis and spine while applying decompression force 194 to the spine.

In some embodiments, a decompression and traction system can impart the desired lordotic shape into the cervical region of the spine and counteract hyper-kyphosis of the area of the upper thoracic spine. Some systems can be used to work the spine and surrounding tissue to promote fluid and cellular exchange in and around the intervertebral discs.

In some embodiments, a device for decompression and traction comprises a frame, a first substantially ellipsoidal inflatable bladder transversely in a neck support cradle carried by the frame, a second inflatable bladder supported on the neck support cradle carried by the frame and configured to provide a force vector against the upper thoracic spine when inflated, one or more restraining straps for securing the device to the user's head such that the first and second bladders are disposed against the back of the neck under a stress point in the cervical spine and against the hyper-kyphotic upper thoracic spine, respectively. Controlled inflation of the bladders by the user by a hand-held pump causes a controlled lifting and a stretching of the cervical and thoracic spine. As the first bladder is inflated, the configuration of the first bladder causes the first bladder to expand vertically and, to a lesser extent, transversely. The vertical expansion lifts the spine, creating a spinal apex while the transverse expansion of the bladder applies an angular traction to the neck on both sides of the apex. As the second bladder is inflated, preferably simultaneously, the configuration of the second bladder causes the second bladder to expand vertically and transversely. The vertical and transverse expansion lifts the spine and applies an angular traction to the thoracic region.

By controlling the inflation of the bladders, the user can control the lifting and stretching of the spine and incrementally increase the magnitude of spinal arc and decompression of the cervical and thoracic regions to his or her own tolerance. As the bladders are repetitively inflated to the tolerance of the user and deflated, the cervical spine is alternatively and actively forced from a lesser arc to a greater or hyper-lordotic arc and the hyper-kyphotic arc of the upper thoracic spine is simultaneously reduced and decompressed, thereby promoting nutrient transport to the intervertebral discs while simultaneously increasing the cervical lordotic arc and decreasing the thoracic hyper-kyphosis. These decompression and traction systems and related methods are described in greater detail below.

Referring now to the drawings, as shown in FIGS. 27-31, according to one embodiment, a traction device 510 comprises a frame 512, openings or slots 514 configured to receive one or more straps to restrain the forehead and/or chin of a user, a first inflatable air bladder 516, a second inflatable air bladder 518, and an air pump assembly 520.

The frame 512 is preferably molded of a durable plastic material in a tubular configuration so as to define a pair of side members 522 and 524 curved and meeting at an apex 526, and a transverse neck support 528. The frame side members 522 and 524 preferably form a stable base. The neck support 528 preferably comprises vertically extending portions 530 and 532 which project upwardly from the side members 522 and 524 respectively and project inwardly to define inwardly directed raised lateral portions 534 and 536. A neck cradle 538 extends transversely between portions 534 and 536, spanning frame side members 522 and 524. In some embodiments, the frame can be provided with side members that are not connected at an apex 526, such as in some embodiments where side members are shorter.

The first and second air bladders 516 and 518 are preferably configured for inflation and simultaneous application of force to the cervical and thoracic spine, when the patient is in a treatment position, to decompressed the spine into its proper lordotic or curved configuration (</\>) with −Y +Z +Y force vectors being applied to the cervical spine while the hyper-kyphotic area of the upper thoracic spine is simultaneously decompressed with a combination +Z/−Y force mid-vector. The cervical spine's lordotic curve is powerfully decompressed and enhanced while the thoracic hyper-kyphosis is simultaneously reduced. In some embodiments, the devices, systems and methods described herein use the entire cervical spine including the occiput (base of skull) as the first anchor point and the upper thoracic spine as the second point. The pneumatic air chambers can directly contact the cervical spine/occiput and the upper 25%-40% of the thoracic spine. The first and second inflatable bladders 516, 518, are described in more detail below.

Figure 32:
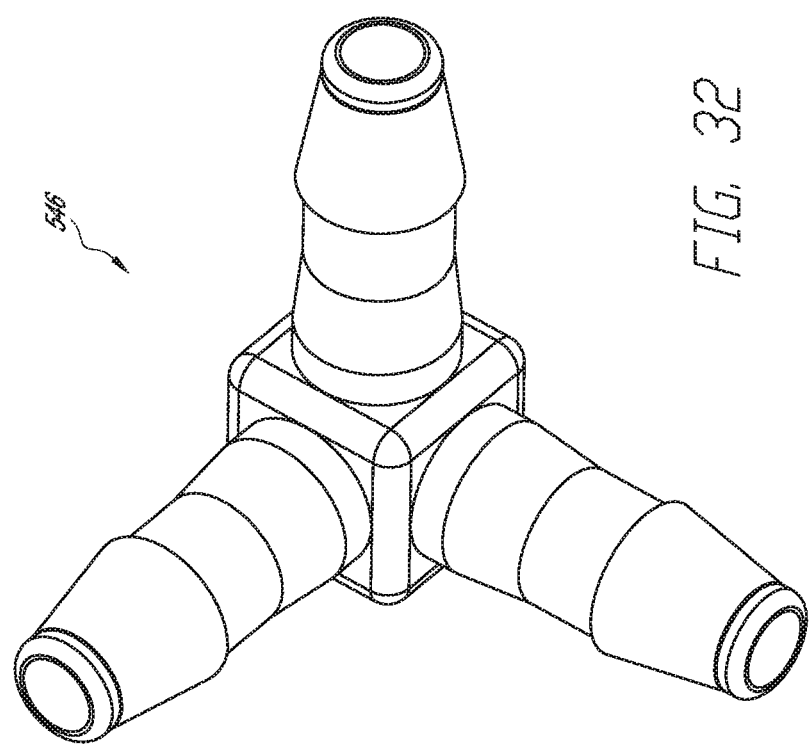
FIG. 32 is a perspective view of a valve component shown in the cross-sectional side view of FIG. 31.

To provide selective inflation and deflation of the first and second inflatable bladders 516, 518, a flexible air line 540 of the air pump assembly 520 communicates the interior of the first and second inflatable bladders 516, 518 with a hand-operated air pump 542. In other embodiments an automated pump can be used. A pressure relief valve 544 is preferably disposed between the air line 540 and pump 542. Air line 540 preferably extends from the relief valve 544 through an opening in the neck support 528 and communicates with the first and second inflatable bladders 516, 518. In some embodiments, the air can be communicated through openings formed in the underside or ends of the bladders. In some embodiments, a valve 546, such as a multi-directional metering valve, shown in FIGS. 31 and 32 for example, can be coupled with the air line 540 and can direct air to the first and second inflatable bladders 516, 518. In some embodiments the valve 546 comprises different lumen diameters to vary the air flow directed to the opposing traction pneumatic air chambers of the first and second inflatable bladders 516, 518. Different valve components can be used to adjust the amount or flow of air to the respective pneumatic air chambers. While air is an example fluid used in the pneumatic decompression described herein, other suitable fluids can be used to increase or decrease the volume of the bladders, including using liquids in some embodiments. In some embodiments, a two pump system can be employed to alternate or unevenly inflate the pneumatic air chambers. In some embodiments, a single complex multi-vectored cell or bladder can be used in place of two individual cells.

According to one embodiment, by way of example, a frame 512 of a traction device 510 defines a spacing of about nine inches between the curved side members 522 and 524 at a wide portion with the side members coming together at the apex 526 of the frame. The frame 512 is preferably between about 11 to 17 inches in length in some embodiments. The frame 512 preferably elevates the neck support 528 about 0.5 to about 1.5 inches above the floor or surface. In such a configuration, the frame 512 preferably bears against the floor or surface during use and reduces the tendency of the frame to twist about its transverse axis. The cradle 538 in neck support 528 preferably tapers from an elevation of about 3 inches above the floor proximate side members 522 and 524 to a central elevation of about 2.5 inches.

The first expandable bladder 516 is preferably coupled to and carried by the neck support 528 in the cradle 538 defined therein. The first expandable bladder 516 is preferably secured in place as will be described further herein. The lateral portions 534 and 536 of neck support 528 are preferably provided with oppositely facing recesses formed therein adjacent the lateral ends of cradle 538 for receiving the extended ends of the first expandable bladder 516 to facilitate retention and alignment of the bladder on the cradle 538.

According to some embodiments, the upper portion of the first expandable bladder 516 is of a generally semi-ellipsoidal configuration having relatively pointed ends similar to the upper half of a football bladder. In one preferred bladder configuration, the underside of the first expandable bladder 516 is formed with undercut portions so as to define a central depending portion. At least a portion of the cradle is preferably configured to receive the underside of the first expandable bladder 516. Preferably, the first expandable bladder 516, when inflated, will expand upwardly from the cradle 538 to a slightly greater extent than in a transverse direction. Additionally, in some embodiments, provision of the depending portion on the underside of the bladder provides a cushioning effect under the apex of the expanded bladder which bears against the user's neck, making the device more comfortable for the user. Thus, as the bladder is inflated under and against the user's neck, it expands vertically and transversely, lifting the spine to create a spinal apex and applying an angular traction to the neck on both sides of the spinal apex. The amount of traction exerted in the vertical direction, however, will be somewhat greater than that exerted longitudinally to obtain the vertical lift necessary to restore the normal lordotic shape to the cervical region of the spine without overly tractioning the neck longitudinally.

In some embodiments, the first inflatable bladder 516 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 516 is constructed of a material that resists expansion. In some embodiments, the bladder 516 is constructed of a heat-sealable urethane with 200 Denier nylon. The bladder 516 can comprise a cover of any suitable material, including, for example, a neoprene material. The semi-ellipsoidal upper portion of the first inflatable bladder 516, when inflated, defines a transverse arc of about 4 inches in length about the center of the bladder. It is to be understood that these dimensions are by way of example only and can be varied, as can the configuration of the frame, straps, and first and second bladders without departing from the spirit and scope of the invention. For example, in some embodiments the bladder 116 can have a length of between about 6 to 9 inches, a height of about 2 to 3 inches in a deflated state, a height of about 3 to 4 inches in an inflated state. In some embodiments a deflated circumference of the bladder is about 4 inches and an inflated circumference of the bladder is between about 7 and 8 inches. In an inflated configuration, the bladder 116 can be taller than it is wide, for example, it can be approximately 4 inches tall and approximately 3 inches wide when inflated in some embodiments.

Figure 33:
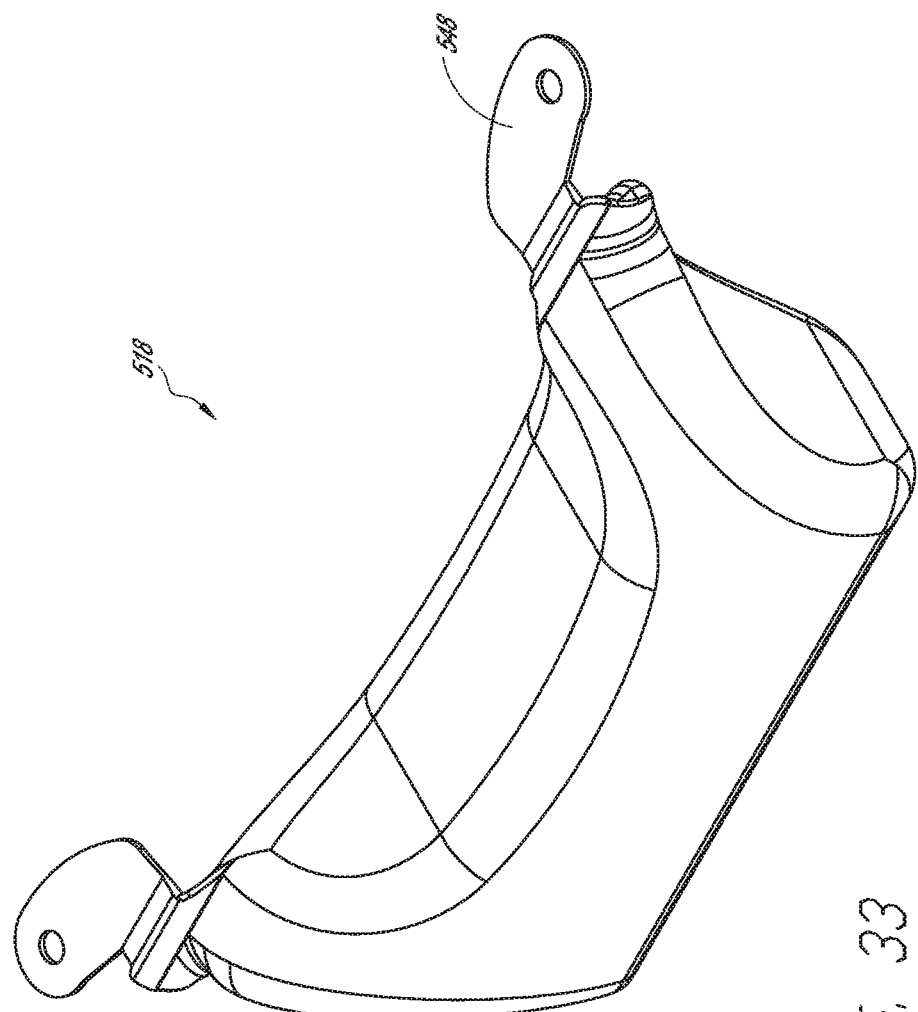
FIG. 33 is a perspective view of a portion of the system shown in FIG. 27, showing a second inflatable bladder in an unassembled configuration.

The second expandable bladder 518 is coupled to and carried by the neck support 528. The second expandable bladder 518 is preferably adjustable in some embodiments to accommodate patient anatomy and align with desired force vector directions as will be described further herein. The lateral portions 534 and 536 of neck support 528 are preferably configured with recesses formed therein for receiving the extended ends 548, shown in FIG. 33, of the second expandable bladder 518 to facilitate retention and alignment of the bladder on the neck support 528.

According to some embodiments, the second expandable bladder 518 is of a generally semi-ellipsoidal configuration having a relatively curved portion upon inflation for engaging a portion of the thoracic spine. Preferably, the second expandable bladder 518, when inflated, will expand about the same amount transversely and upwardly from the neck support 528. In some embodiments, the second expandable bladder 518 when inflated expands more transversely than upwardly. In some embodiments, the second expandable bladder 518 when inflated expands more upwardly than transversely. Thus, as the second expandable bladder 518 is inflated under and against the user's thoracic spine, it expands transversely and vertically, lifting the spine to counter hyper-kyphosis and applying an angular traction to the thoracic spine. The amount of traction exerted in the longitudial direction, preferably, will be similar to the amount of lift exerted vertically to obtain the necessary decompression and lift to restore the normal shape to the thoracic region of the spine.

In some embodiments, the second inflatable bladder 518 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 518 is constructed of a material that resists expansion. In some embodiments, the bladder 518 is constructed of a heat-sealable urethane with 200 Denier nylon. The bladder 518 can comprise a cover of any suitable material, including, for example, a neoprene material. The second inflatable bladder 518, when inflated, defines a transverse arc of about 4 inches in length about the center of the bladder. It is to be understood that these dimensions are by way of example only and can be varied without departing from the spirit and scope of the invention. For example, in some embodiments the bladder 518 can have a length of about 9 inches where it is coupled to the frame, a length of between about 6 and 7 inches where the bladder 518 contacts the patient. The bladder 518 can have a height of about 3 to 4 inches. The bladder 518 can have a circumference of about 6 to 7 inches.

In some embodiments the bladders preferably have a finite shape and expand while being filled until the bladders reach the finite shape. Once the bladder has been filled to the finite shape, the pressure release valve of the pump assembly allows for gas or fluid to escape from the system to maintain a desired pressure within the bladder. The pressure release valve is preferably an automatic pressure release valve. The system preferably also comprises a manual release valve, such as a push button release valve. The desired pressure is preferably held at a proven clinical level. In some embodiments the pressure release valve is configured to maintain a pressure of about 8 psi. At a pressure of about 8 psi the system preferably provides over 50 pounds of tractional force. In some embodiments the tractional force preferably is between about 50 and 60 pounds of tractional force.

While the above described bladder configurations are preferred, it is to be understood that other configurations of expandable bladders could be employed in the present invention, either with or without an expansion controlling casing to provide the desired lifting and traction of the user's neck and spine. Moreover, in some embodiments, mechanically expandable components can be used in place of the first and second bladders. Mechanically expandable components can be coupled to the frame and selectively expanded to apply force vectors to the cervical and thoracic spine in a manner similar to those produced by the expandable bladders as described herein. For example, in some embodiments an expanding mechanical component within a cushioned cover can be selectively actuated to provide the desired force distribution.

In some embodiments, one or more of the first and second expandable bladders 516, 518 are of a tubular configuration and are disposed in a non-expandable casing, preferably constructed of a vinyl or other suitable material. The casing is preferably formed in the above described generally ellipsoidal configurations. As the tubular bladder expands upon inflation, the expansion is limited by the configuration of the casing to provide the desired increase in the vertical and transverse directions.

In some embodiments, as shown in FIG. 8, the first expandable bladder 516 is preferably rotatably secured to the neck support 528. The first expandable bladder 516 can be tilted in a forward position, a backward position, or maintained in a central position. In some embodiments, the bladder can be locked into a desired position. Providing a rotatable first expandable bladder 516 preferably provides mobility for the pneumatic air chamber to comfortably accommodate various spinal configurations. In some embodiments, the second expandable bladder 518 can be rotatably secured to the neck support 528.

Figure 34:
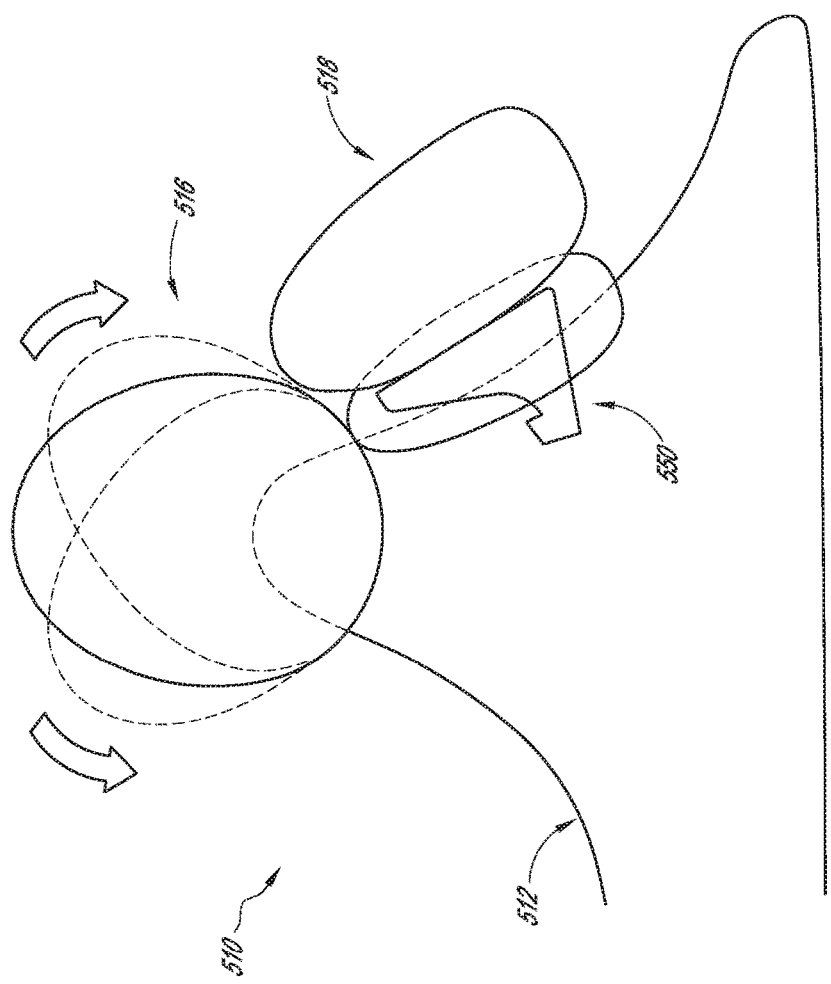
FIG. 34 is a schematic view of another embodiment of a decompression and traction system, showing mobile pneumatic air chambers comprising a first inflatable bladder being pivotably adjustable and showing a spacer component configured to be selectively coupled to the frame to adjust a position of a second inflatable bladder.
Figure 35:
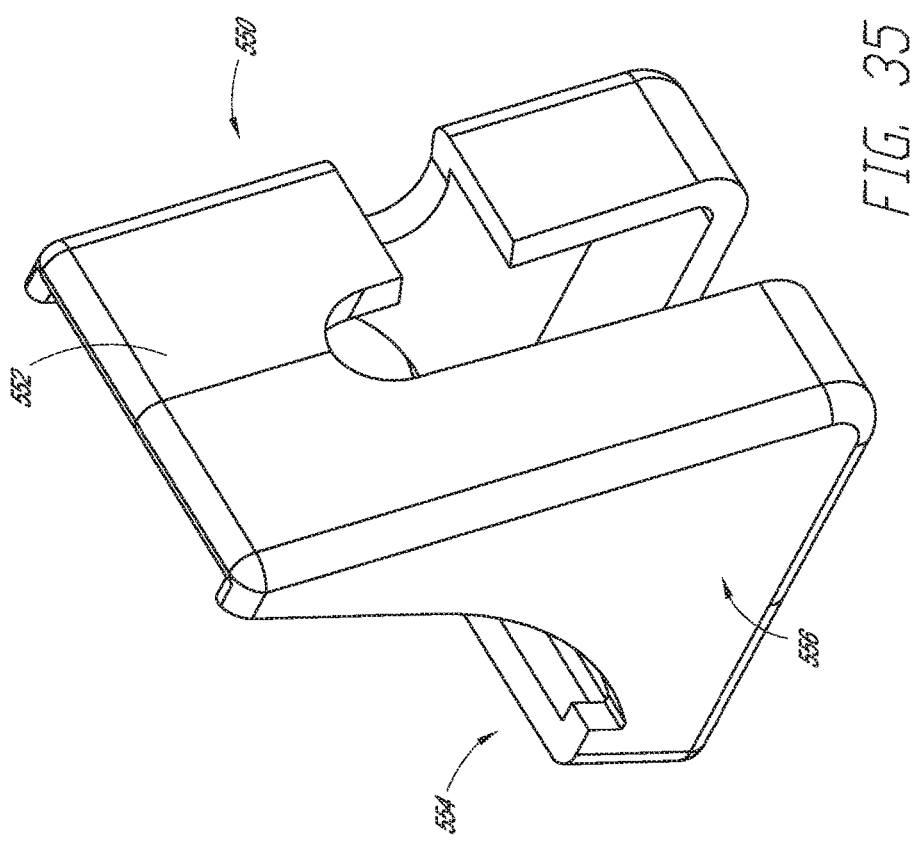
FIG. 35 is a perspective view of the spacer component shown in FIG. 34.

In some embodiments, as shown in FIGS. 34 and 35, a spacer component 550 is preferably configured to be selectively coupled to the frame 512 to adjust a position of a second inflatable bladder 518. The spacer component can be attached to the frame and can allow clinicians and users to increase the negative Y directional component of the lower pneumatic air chamber. In one embodiment, the spacer component comprises an pneumatic air chamber or bladder engaging face 552, a notched connector portion 554 and opposing side portions 556. Other spacer configurations can be used to modify the directional component of the second inflatable bladder 518.

FIGS. 36A-F are illustrative views of a patient's spine in multiple configurations, including some embodiments of decompression and traction systems in use in deflated and inflated configurations. FIG. 36A shows a patient with cervical curve loss, forward head carriage, and disc compression. FIG. 36B shows a patient with normal spinal curves. FIGS. 36C and 36D show a patient and one embodiment of a decompression system 510 having a chin and forehead restraint, wherein the views show the decompression system 510 in a deflated configuration and an inflated configuration, respectively. FIGS. 36E and 36F show a patient and another embodiment of a decompression system 510 having a forehead restraint, wherein the views show the decompression system 510 in a deflated configuration and an inflated configuration, respectively.

As shown in FIGS. 36C-F, restraint straps 558 and/or 560 can be secured at the ends thereof to one or more of slots 514. Straps can be passed under the user's chin and over the user's forehead in some embodiments. In other embodiments, a strap can be passed over the user's forehead only. The straps can be secured and fastened in any suitable manner. For example, interlocking hook and loop type fasteners, snaps, buckles or other fasteners can be used. According to some embodiments, the traction device 510 can be easily and securely affixed to the user's head with a strap configuration such that with the user lying flat on his or her back on a horizontal surface, the frame 512 rests on the surface and the neck support 528 is disposed under the user's neck and tapered ends 562 of the frame side members 522, 524 are substantially adjacent the user's shoulders and generally near the upper thoracic region. The tightness of the securement of the device 510 to the user's head can be readily adjusted as needed by the securement straps 558, 560.

In some embodiments, the system preferably comprises a frame made of virgin acrylonitrile butadiene styrene (ABS) plastic material. ABS is an engineering thermoplastic that is advantageous due to its strength, toughness, chemical resistance, and ability to maintain necessary stiffness. The expandable pneumatic air chambers are preferably made of heat-sealable urethane with 200 Denier nylon. The expandable pneumatic air chambers preferably have a neoprene cover. The facial straps are preferably made of a durable and waterproof neoprene material. The hand pump and tubing are preferably made of rubber/plastic. Other embodiments can include different materials.

According to some embodiments, the system is lightweight (for example, about 3 lbs), portable, easy to operate, requires no assembly, no weights, cables or ropes to set-up, comes with choice of ballistic nylon carrying case or educational box, instruction page and instructional DVD. In one embodiment, the device comprises a built-in frame, an expanding elliptical pneumatic air chamber (with neoprene cover) that creates radial tractional force and thoracic decompressive force, a patient-controlled pneumatic hand pump with a push button release and automatic safety valve connected to approximately 30 inches of tubing, and one dual action head restraint designed for patients who suffer with TMJ (does not aggravate temporomandibular joint), which comprises an adjustable forehead strap, and a removable chin strap (which is optional in some other embodiments).

Accordingly to one aspect disclosed herein, methods for pneumatic radial traction can restore the cervical and thoracic spine to the proper configuration. Pneumatic radial traction, also known in some embodiments as expanding ellipsoidal decompression (EED), is a process in which joints of the cervical spine are pneumatically tractioned and simultaneously aligned into the cervical spine's proper radial or curved configuration. A major clinical difference between some embodiments of a pneumatic radial traction device disclosed herein and some prior art devices is that the prior art devices flatten or reverse the proper cervical curve to attain joint separation. In some embodiments, a pneumatic radial traction device enhances or maintains the proper cervical curve while attaining over twice the joint separation as some prior art devices.

With reference to FIGS. 36A and 36B, in the upright position, the cervical "lordotic" curve is what allows the weight of the head (10-15 lbs.) to be directed toward the hard boney posterior articular surfaces of the neck rather than toward the softer anterior discs as in the compressed neck. Through modern healthcare imaging it can be seen that that loss of the normal forward cervical curve)(approx. 43° and the resulting anterior disc compression this causes, was a contributing factor in osteophyte formation (Wolff's Law), posterior disc bulging, disc herniation, disc degeneration, neck pain and loss in cervical range of motion.

With reference to FIGS. 36C to 36F, pneumatic radial traction separates and simultaneously aligns the spinal joints in a curved or radial configuration. In some embodiments, an elliptical pneumatic air chamber directs multi-vectored expansive forces from within the posterior spinal concavity (back of neck), vertically (+Z axis translation) and in both horizontal directions. The spine is simultaneously tractioned in three main directions. The radial configuration created by these multi-vectored forces produces high level joint separation at the posterior, middle and anterior of the disc while forcefully enhancing the cervical spine's proper curve, rather than flattening or reversing the curve. Pneumatic radial traction is preferably achieved when the joints are separated by a vertical displacement greater than the horizontal displacement, however, displacement of equal height and width is also advantageous in some embodiments. An advantage of a pneumatic radial traction device is that it does not flatten or reverse the proper cervical curve while attaining joint separation. In some embodiments, the system provides a traction device with multiple fulcrums. For example, at least two fulcrums are provided to provide treatment to the cervical and thoracic spine of the patient.

As the head is stabilized in the cervical device, joints are actively tractioned in 3 main directions instead of one or two. The cervical spine is tractioned vertically along the +Z axis with a pneumatic force of over 58 lbs. This force expands into and against the posterior cervical concavity. Simultaneously the spine is tractioned horizontally in the two traditional directions (+Y and −Y) with a pneumatic force of over 40-lbs in each direction. These forces expand against the occiput and against the upper thoracic region. The combination of these simultaneously applied pneumatic forces produce radial traction. When fully inflated the elliptical pneumatic cell expands to a 7.5 inch radius, affecting the entire cervical spine. High level joint traction occurs at the posterior, center and anterior aspect of the vertebral bodies in a ratio coinciding with the discs' natural wedged spacing. While the pneumatic radial traction device separates the posterior of the joints to a magnitude typical of traditional traction, it separates the overall disc more than twice as much as linear traction.

With the simultaneous application of two separate pneumatic air chambers the cervical spine is decompressed into its proper lordotic or curved configuration (</\>) with −Y +Z +Y force vectors while the hyper kyphotic area of the upper thoracic spine is simultaneously decompressed with a combination +Z/−Y force mid-vector. The cervical spine's lordotic curve is powerfully decompressed and enhanced while the thoracic hyper-kyphosis is simultaneously reduced.

Continuous expansion and contraction of the pneumatic air chambers can be employed to create alternating hydration and milking of the intervertebral discs, activating their sponge-like imbibition action. Holding the air pressure constant over a period of 15 to 20 minutes has the effect of simultaneously molding the spine into a curved or elliptical shape, decompressing discs and relaxing the dura, cord and nerve-roots in the cervical canal.

Embodiments described herein are preferably prescribed for patients with chronic neck pain due to a musculoskeletal or neurological impairment. The system applies radial tractional force to the cervical spine, enhancing the cervical lordotic curve while achieving high level joint separation at the anterior, center and posterior aspect of the vertebral bodies and discs in a ratio corresponding with their natural wedged spacing, reducing disc protrusions, compression and increasing range of motion. In some applications, devices advantageously decrease pain in chronic neck pain patients, decrease headaches and increase range of motion while reducing the necessity for chronic pain medication and neck surgery.

With continued reference to FIGS. 36A-36F, according to some embodiments in use, the traction device 510 rests on a horizontal surface such that the neck support 528 projects upwardly therefrom. The user lies on the device in a prone position such that the back of the neck rests on the deflated first expandable bladder 516 carried in the cradle 538 of the neck support 528. The deflated second expandable bladder 518 is positioned between the neck support 528 and portions of the thoracic spine of the user. The chin and/or forehead restraining restraint straps are respectively extended under the user's chin and/or about the user's forehead and secured, thereby affixing the traction device 510 to the user such that the neck and cervical spine extend over the neck support and first expandable bladder 516 and the thoracic spine is adjacent the second expandable bladder 518. According to one preferred embodiment, the outward extension of the neck support 528 is relatively slight so that when the bladder is in the deflated position with the forehead and chin restraints secured, very little or no force is exerted on the neck by the neck support. This is achieved by elevating the neck support 528 above the frame such that the neck cradle 538 formed therein is about 2 to 3 inches above the floor or other horizontal surface on which the device 510 is used. The first expandable bladder 516 is sized such that upon full inflation, the apex of the curved upper surface of the bladder will extend about 5 inches above the floor or surface. The second expandable bladder 518 is sized such that upon full inflation, a surface of the second expandable bladder engaging the thoracic spine will extend toward the thoracic spine about 2 to 3 inches in the −Y/+Z direction.

In some embodiments, as the user slowly inflates the first and second inflatable bladders 516, 518 using the air pump 542, the first inflatable bladder 516 expands upwardly and, to a lesser extent, transversely, thereby forcing the cervical spine forwardly creating a spinal apex while concurrently stretching the spine angularly along both sides of the formed spinal apex. The second inflatable bladder 518 expands transversely in the −Y direction, thereby forcing the thoracic spine forwardly to offset the effects of hyper-khyphosis. The user then continues to inflate the first and second bladders 516 and 518 until his or her individual tolerance level is reached. The bladders are then deflated by use of the one way valve 544. The process is preferably repeated several times, slowly increasing the spinal arc in the cervical region and placing pressure on the thoracic region as the level of tolerance increases. In addition, the first and second bladders 516 and 518 can be held in an inflated state at or slightly below the level of tolerance for varying periods of time up to ten to twenty minutes. Through such repetition, the cervical spine, thoracic spine and surrounding tissue receive a workout promoting cellular exchange in and around the intervertebral disc and a forward curve is reinstated into the cervical spine while achieving proper spine configuration in the thoracic region. FIGS. 36A-36F illustrate the effects of the traction and exercise devices 110 of some embodiments on the cervical and thoracic spine.

Figure 37:
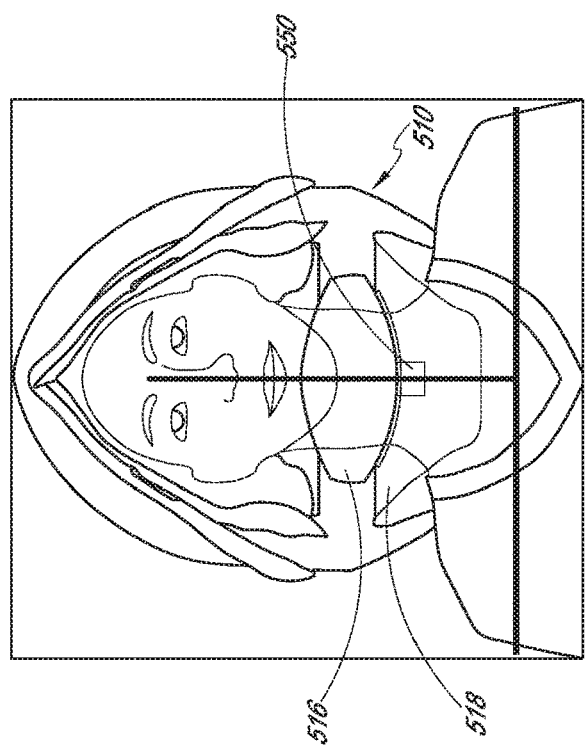
FIG. 37 is a schematic top view of a patient positioned on another embodiment of a decompression and traction system, showing pneumatic air chambers comprising first and second inflatable bladders and an adjustable spacer component configured to be selectively coupled to the frame to adjust a position of the second inflatable bladder, in the shown configuration the spacer component adjusts the position of the second inflatable bladder to provide an even distribution of force generally along a force vector in the −Y and +Z plane.

With reference to FIGS. 37-40, an adjustable spacer component 550 can be provided in some implementations of a traction system 510 to provide for lateral flexion traction. For example, FIG. 37 is a schematic top view of a patient positioned on another embodiment of a decompression and traction system, showing pneumatic air chambers comprising first and second inflatable bladders 516, 518 and an adjustable wedge-shaped spacer component 550 configured to be selectively coupled to the frame to adjust a position of the second inflatable bladder, in the shown configuration the spacer component is in a vertical orientation and adjusts the position of the second inflatable bladder to provide an even distribution of force generally along a force vector in the −Y and +Z plane without providing any lateral flexion traction to the patient.

Figure 38:
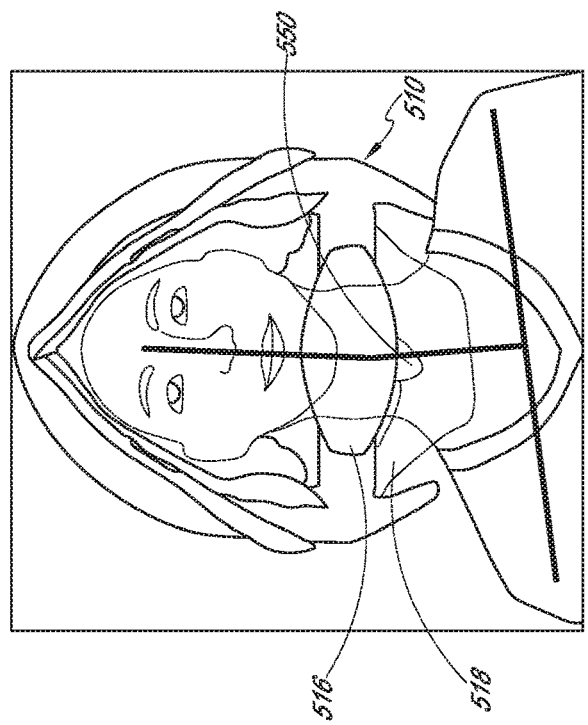
FIG. 38 is a schematic top view of a patient and the embodiment of FIG. 37, showing a configuration wherein the spacer component is moved to adjust the position of the second inflatable bladder to provide an uneven distribution of force on one side of the patient in that a force vector is directed, for example, in a −Y, +Z, and −X direction.

FIG. 38 shows a configuration wherein the spacer component is moved to adjust the position of the second inflatable bladder to provide an uneven distribution of force on one side of the patient in that a force vector is directed, for example, in a −Y, +Z, and −X direction. For example, the spacer component is turned or rotated to a horizontal position, whereby the wedge shape of the spacer contacts the second inflatable bladder and causes the bladder to deflect in one lateral direction more than another lateral direction. As shown, the spacer is placed in right horizontal position and causes more deflection on the right side of the patient. In other configurations, the spacer can be positioned in a left horizontal position to cause more deflection on the left side of the patient. Based on the positioning of the spacer, the second bladder can expand in an angular direction. Turning the spacer component sideways creates lateral flexion traction by forcing the shoulder/trapezius down while the head is held in traction.

Figure 40:
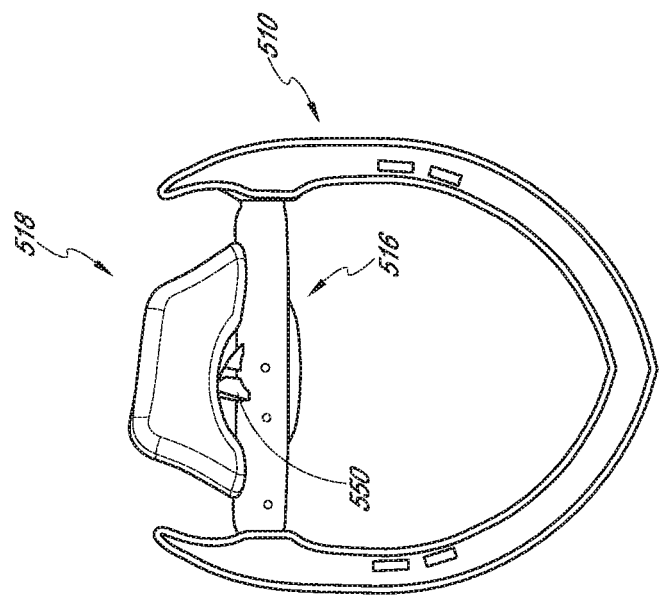
FIG. 40 is a bottom view of the embodiment of FIG. 37, showing a configuration wherein the spacer component is moved to adjust the position of the second inflatable bladder to provide an uneven distribution of force to a patient in that a force vector is directed, for example, in a −Y, +Z, and −X direction.
Figure 39:
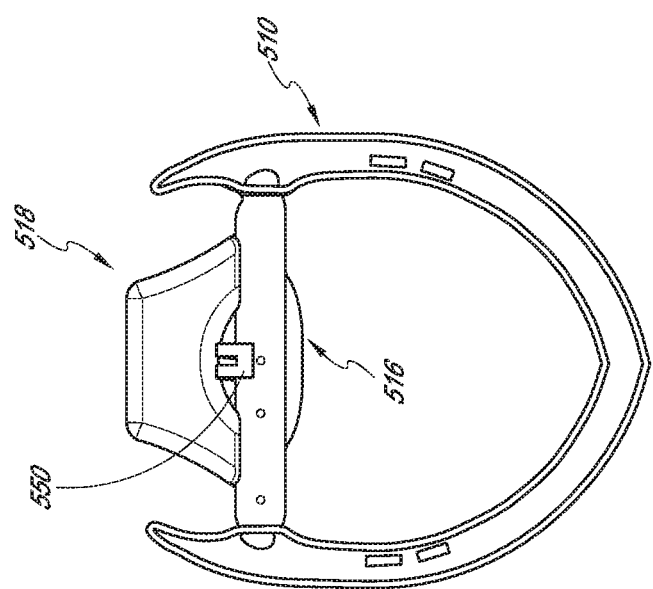
FIG. 39 is a bottom view of the embodiment of FIG. 37, in the shown configuration the spacer component adjusts the position of the second inflatable bladder to provide an even distribution of force generally along a force vector in the −Y and +Z plane.
Figure 41:
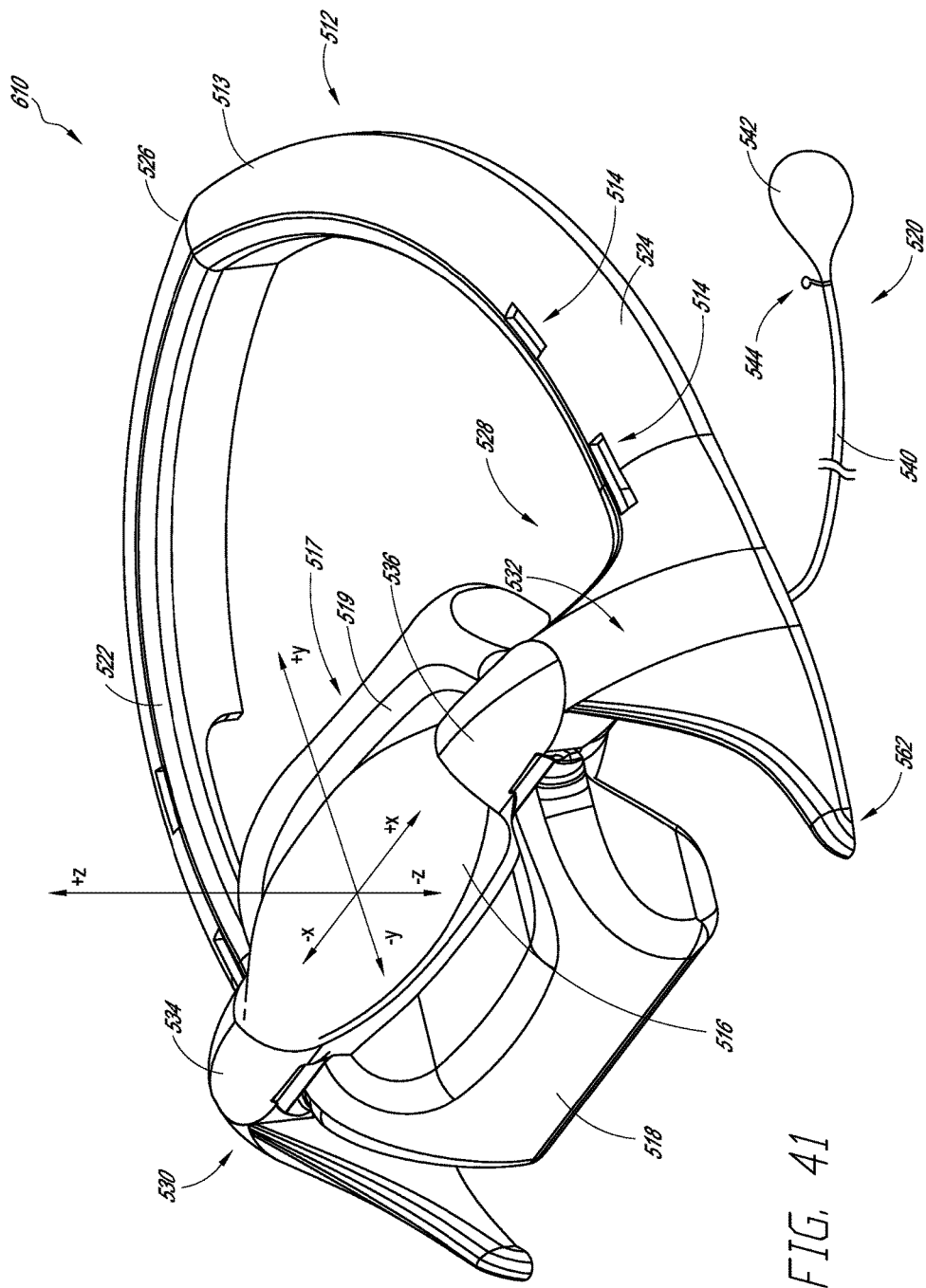
FIG. 41 is a perspective view of one embodiment of a decompression and traction system.
Figure 42:
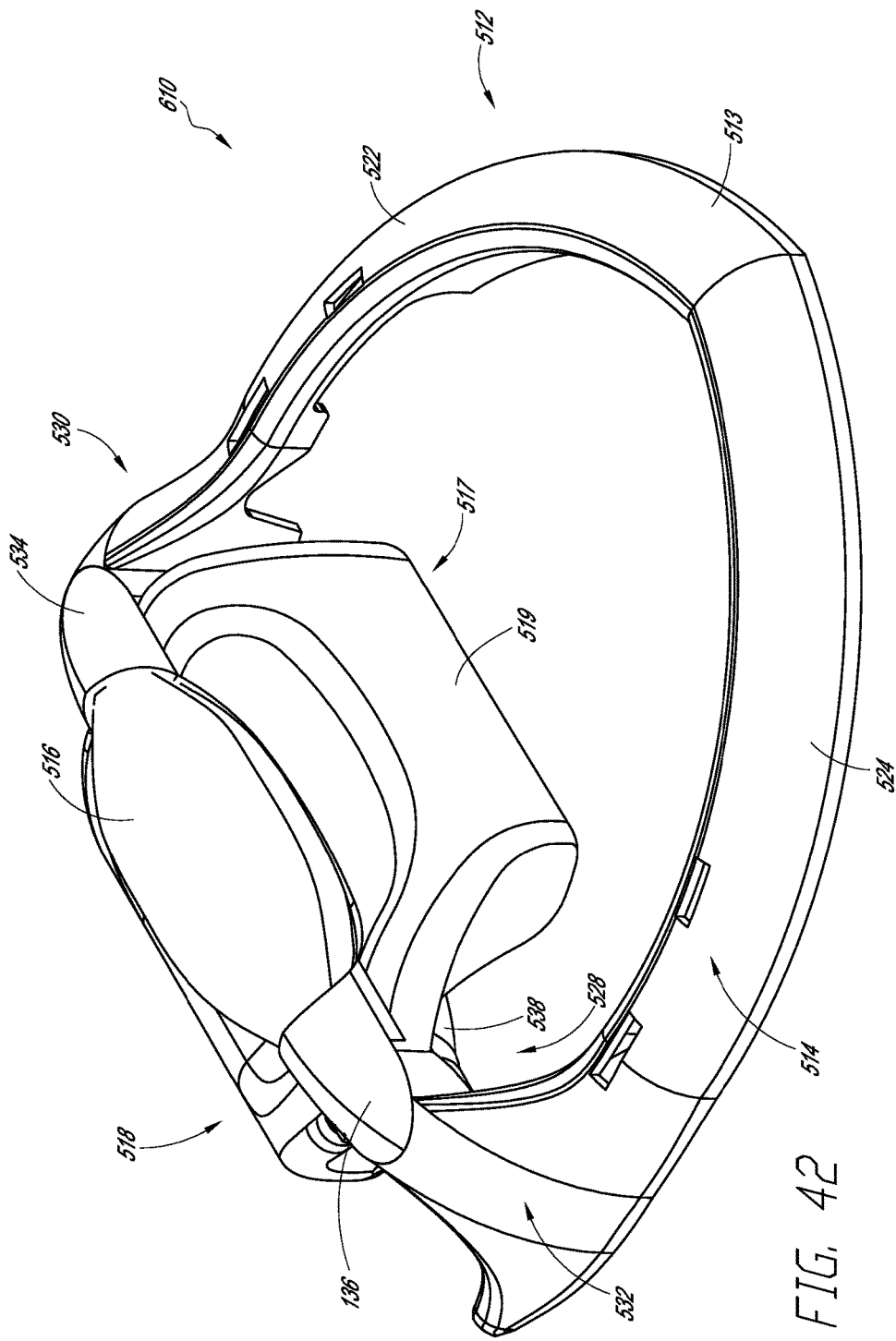
FIG. 42 is a perspective view of a portion of the system shown in FIG. 41.
Figure 43:
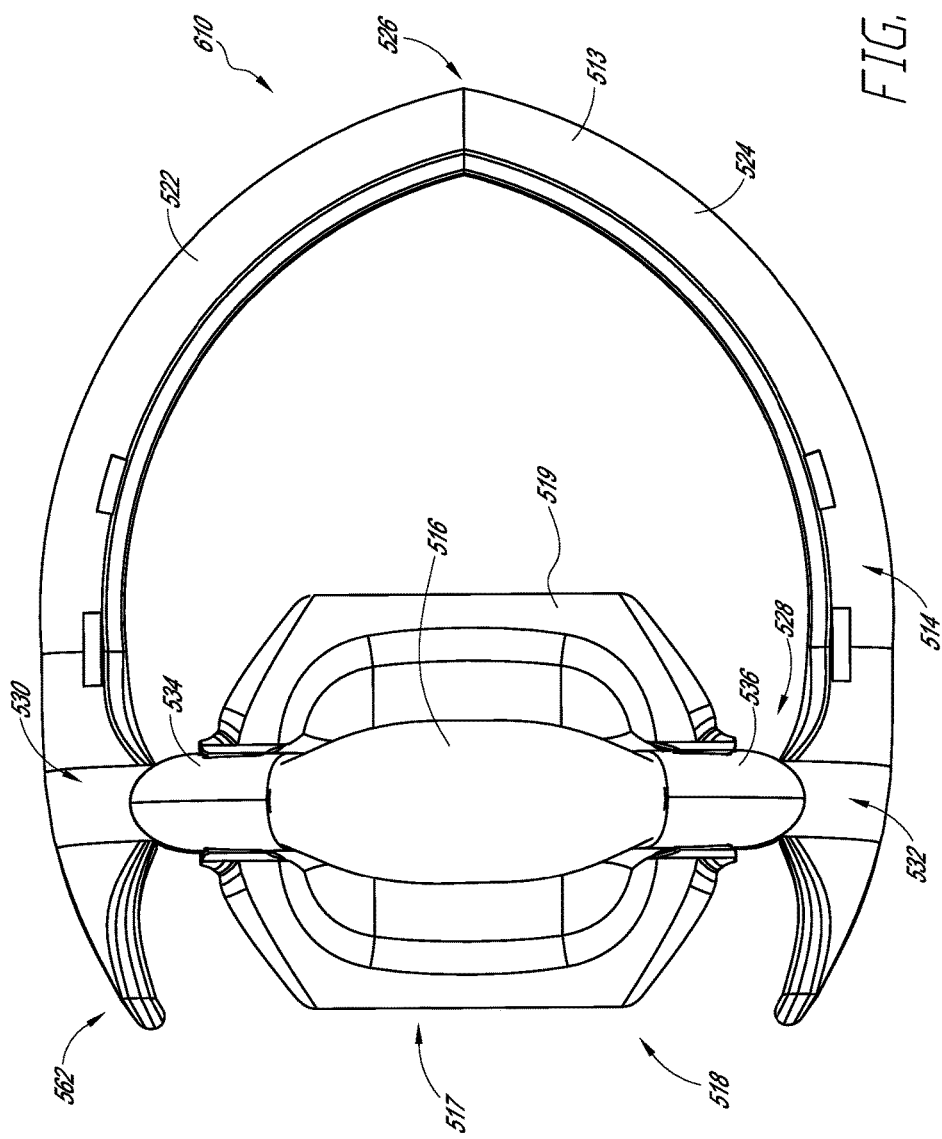
FIG. 43 is a top view of a portion of the system shown in FIG. 41.
Figure 44:
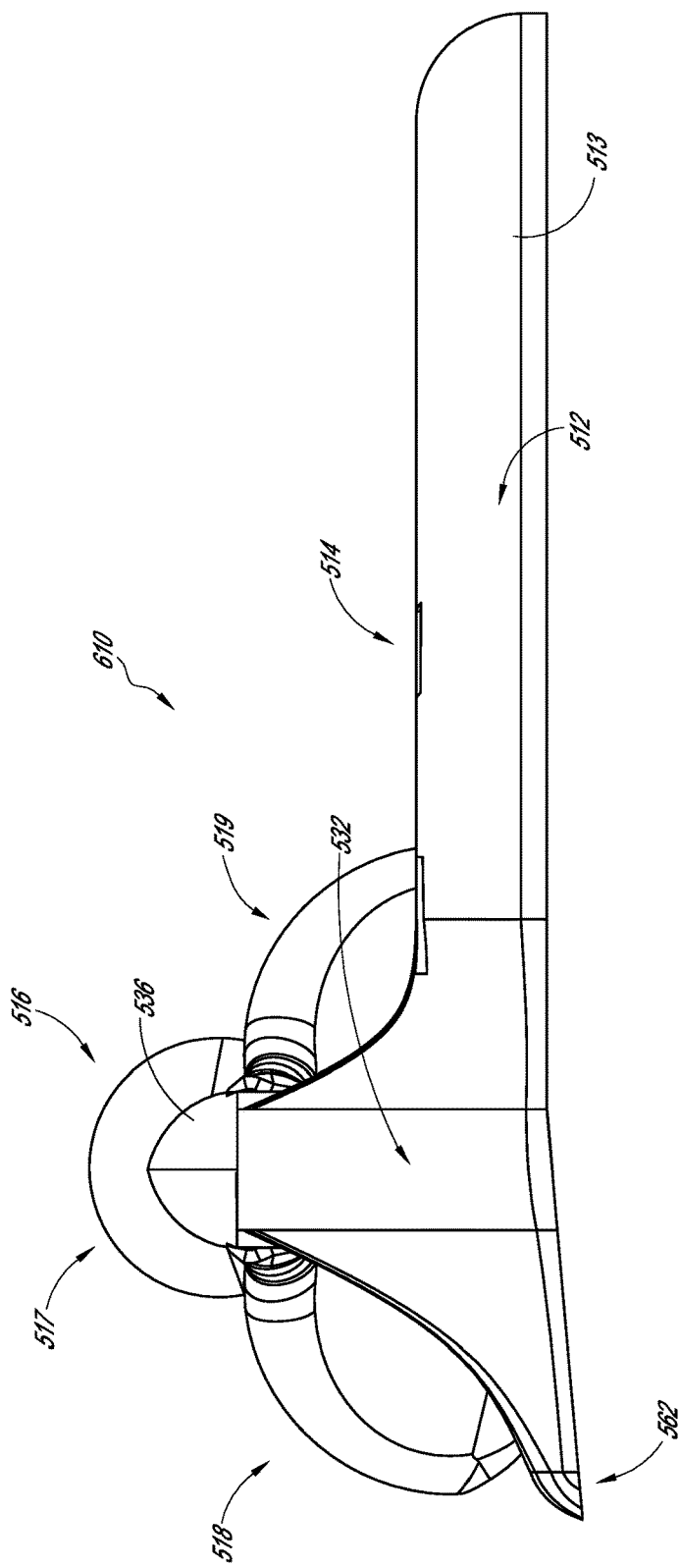
FIG. 44 is a side view of a portion of the system shown in FIG. 41.
Figure 45:
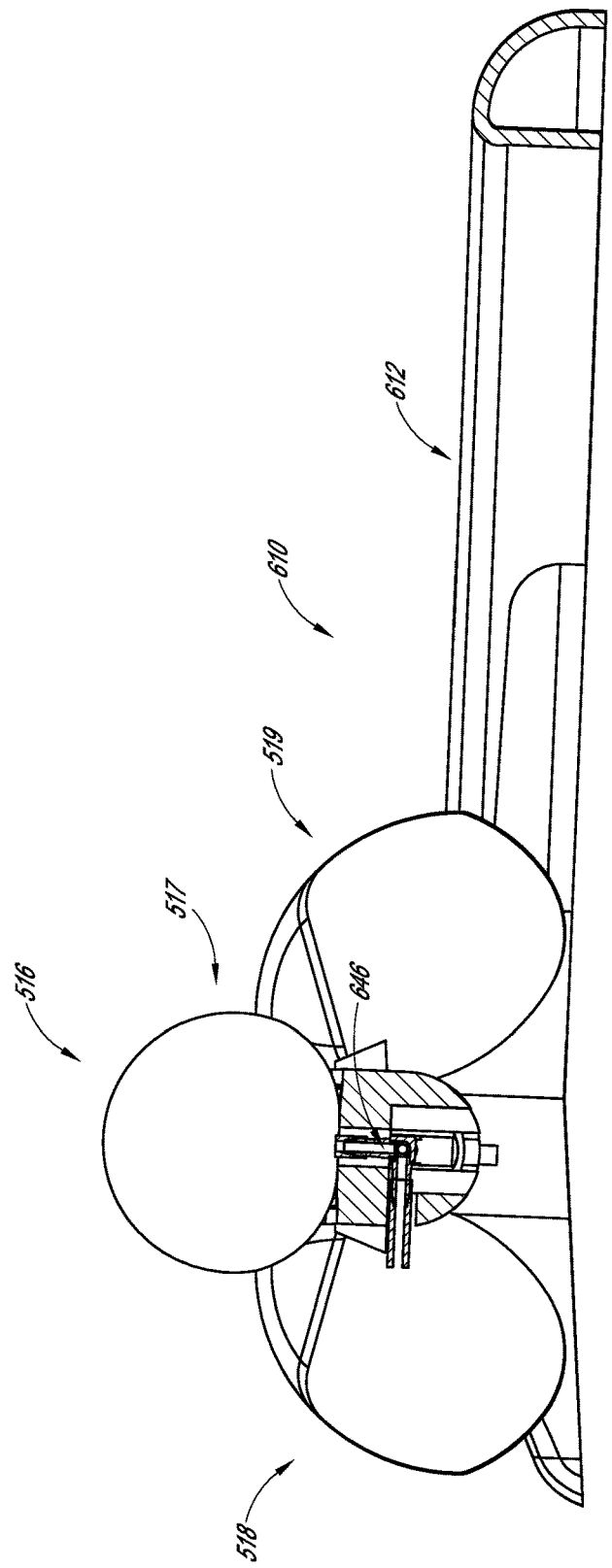
FIG. 45 is a cross-sectional side view of a portion of the system shown in FIG. 41.

FIG. 39 is a bottom view of the embodiment of FIG. 37 and shows the spacer component in a vertical position that adjusts the position of the second inflatable bladder to provide an even distribution of force generally along a force vector in the −Y and +Z plane, but does not direct force laterally in a −X or +X direction. FIG. 40 is a bottom view of the embodiment of FIG. 37, showing a configuration wherein the spacer component is moved to adjust the position of the second inflatable bladder to provide an uneven distribution of force to a patient in that a force vector is directed, for example, in a −Y, +Z, and −X direction as described in connection with FIG. 38. The lower linear displacement pneumatic air chamber is adjusted with a rotating wedge shaped spacer component, allowing clinicians to increase the angle and force of the mid (−Y)/(+Z) vector of this pneumatic air chamber. When adjusted to the right or left horizontal position, the rotating wedge allows clinicians to unilaterally increase and rotate the (−Y) directional component on either the right or left side (+/−X) of the upper thoracic region, producing lateral flexion traction. The rotating wedge shaped spacer component can be removed in some implementations to accommodate extreme kyphotic thoracic spines.

In some embodiments, the device comprises a frame, a first substantially ellipsoidal inflatable bladder transversely in a neck support cradle carried by the frame, a second inflatable bladder supported on the neck support cradle carried by the frame and configured to provide a force vector against the upper thoracic spine when inflated, a third inflatable bladder supported on the neck support cradle carried by the frame and configured to provide a force vector against the occiput when inflated, one or more restraining straps for securing the device to the user's head such that the first and second bladders are disposed against the back of the neck under a stress point in the cervical spine and against the hyper-kyphotic upper thoracic spine, respectively. Controlled inflation of the bladders by the user by a hand-held pump causes a controlled lifting and a stretching of the cervical and thoracic spine and decompression of the occipital-cervical junction. As the first bladder is inflated, the configuration of the first bladder causes the first bladder to expand vertically and, to a lesser extent, transversely. The vertical expansion lifts the spine, creating a spinal apex while the transverse expansion of the bladder applies an angular traction to the neck on both sides of the apex. As the second bladder is inflated, preferably simultaneously, the configuration of the second bladder causes the second bladder to expand vertically and transversely. The vertical and transverse expansion lifts the spine and applies an angular traction to the thoracic region. As the third bladder is inflated, preferably simultaneously, the configuration of the third bladder causes the third bladder to expand vertically and transversely. The vertical and transverse expansion lifts the head and applies an angular traction to the occiput.

By controlling the inflation of the bladders, the user can control the lifting and stretching of the spine and incrementally increase the magnitude of spinal arc and decompression of the cervical region, thoracic region, and occipital-cervical junction to his or her own tolerance. As the bladders are repetitively inflated to the tolerance of the user and deflated, the cervical spine is alternatively and actively forced from a lesser arc to a greater or hyper-lordotic arc, the hyper-kyphotic arc of the upper thoracic spine is simultaneously reduced and decompressed, and the occipital-cervical junction is simultaneously decompressed, thereby promoting nutrient transport to the intervertebral discs while simultaneously increasing the cervical lordotic arc and decreasing the thoracic hyper-kyphosis. These decompression and traction systems and related methods are described in greater detail below.

Referring now to the drawings, as shown in FIGS. 41-45, according to one embodiment, a traction device 610 comprises the frame 512, openings or slots 514 configured to receive one or more straps to restrain the forehead and/or chin of a user, an inflatable bladder system 517 including the first inflatable air bladder 516, the second inflatable air bladder 518, and a third inflatable bladder 519, and an air pump assembly 520.

The frame 512 is preferably molded of a durable plastic material in a tubular configuration so as to define a pair of side members 522 and 524 curved and meeting at an apex 526, and a transverse neck support 528. The frame side members 522 and 524 preferably form a stable base 513. The neck support 528 preferably comprises vertically extending portions 530 and 532 which project upwardly from the side members 522 and 524 respectively and project inwardly to define inwardly directed raised lateral portions 534 and 536. A neck cradle 538 extends transversely between portions 534 and 536, spanning frame side members 522 and 524. In some embodiments, the frame can be provided with side members that are not connected at an apex 526, such as in some embodiments where side members are shorter.

The first, second, and third air bladders 516, 518, and 519 are preferably configured for inflation and simultaneous application of force to the cervical spine, the thoracic spine, and the occiput, when the patient is in a treatment position, to decompress the spine into its proper lordotic or curved configuration (</\>) with −Y +Z +Y force vectors being applied to the cervical spine while the hyper-kyphotic area of the upper thoracic spine is simultaneously decompressed with a combination +Z/−Y force mid-vector and +Z/+Y force vectors are applied to the occiput to decompress the occipital-cervical junction. The cervical spine's lordotic curve is powerfully decompressed and enhanced while the thoracic hyper-kyphosis is simultaneously reduced. In some embodiments, the devices, systems and methods described herein use the entire cervical spine as a first anchor point, the upper thoracic spine as a second point, and the occiput as a third anchor point. The pneumatic air chambers can directly contact the cervical spine, the upper 25%-40% of the thoracic spine, and the occiput. The first, second, and third inflatable bladders 516, 518, and 519 are described in more detail below.

To provide selective inflation and deflation of the first, second, and third inflatable bladders 516, 518, and 519, a flexible air line 540 of the air pump assembly 520 communicates the interior of the first, second, and third inflatable bladders 516, 518, and 519 with a hand-operated air pump 542. In other embodiments an automated pump or electronic pump can be used. The electronic pump may be part of an electronic pump system. In certain embodiments, the electronic pump system can include a processor configured to execute one or more software applications that cause the electronic pump to fill one or more of the first, second, and third inflatable bladders 516, 518, and 519. In certain embodiments, the electronic pump can be configured to inflate one or more of the first, second, and third inflatable bladders 516, 518, and 519 to one or more predefined or user selected inflation amounts. For example, in some embodiments, the software applications allow for selective inflation of one or more of the first, second, and third inflatable bladders 516, 518, and 519 to low, medium, and/or high amounts of inflation. In certain embodiments, the electronic pump system can include a user interface that allows a user to select and/or control one or more settings of the pump. For example, the user interface can allow for a selection of one or more of the first, second, and third inflatable bladders 516, 518, and 519 for inflation. In some embodiments, the user interface can allow for a selection of one or more inflation amounts for each inflatable bladder. In certain embodiments, the user interface can be provided on the electronic pump. In some embodiments, the user interface can be provided on an external device.

Figure 46:
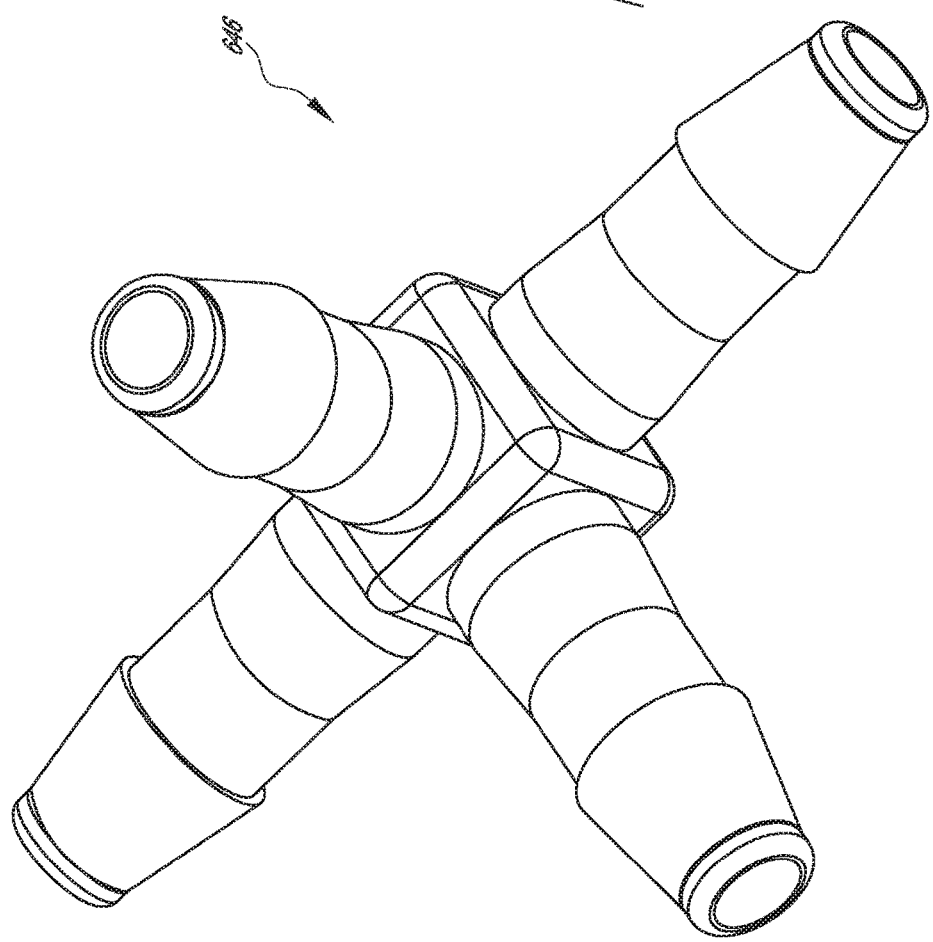
FIG. 46 is a perspective view of a valve component shown in the cross-sectional side view of FIG. 45.

A pressure relief valve 544 is preferably disposed between the air line 540 and pump 542. Air line 540 preferably extends from the relief valve 544 through an opening in the neck support 528 and communicates with the first and second inflatable bladders 516, 518. In some embodiments, the air can be communicated through openings formed in the underside or ends of the bladders. In some embodiments, a valve 646, such as a multi-directional metering valve, shown in FIGS. 45 and 46 for example, can be coupled with the air line 540 and can direct air to the first, second, and third inflatable bladders 516, 518, and 519. In some embodiments the valve 646 comprises different lumen diameters to vary the air flow directed to the opposing traction pneumatic air chambers of the first, second, and third inflatable bladders 516, 518, and 519. Different valve components can be used to adjust the amount or flow of air to the respective pneumatic air chambers. While air is an example fluid used in the pneumatic decompression described herein, other suitable fluids can be used to increase or decrease the volume of the bladders, including using liquids in some embodiments. In some embodiments, a two pump system or a three pump system can be employed to alternate or unevenly inflate the pneumatic air chambers. For example, in some embodiments, a first pump can be employed to inflate the first inflatable bladder 516 and a second pump can be employed to inflate the second and third inflatable bladders 518 and 519. In some embodiments, a first pump can be employed to inflate the first and second inflatable bladders 516 and 518 and a second pump can be employed to inflate the third inflatable bladder 519. In some embodiments, a pump can be employed to inflate the first and third inflatable bladders 516 and 519 and a second pump can be employed to inflate the second inflatable bladder 518. In some embodiments, a single complex multi-vectored cell or bladder can be used in place of three individual cells. In some embodiments, a single complex multi-vectored cell or bladder can be used in place of two of three inflatable bladders 516, 518, and 519. For example, in some embodiments, a single complex multi-vectored cell or bladder can be used in place of the first and second inflatable bladders 516 and 518. In some embodiments, a single complex multi-vectored cell or bladder can be used in place of the first and third inflatable bladders 516 and 519.

According to one embodiment, by way of example, a frame 512 of a traction device 510 defines a spacing of about nine inches between the curved side members 522 and 524 at a wide portion with the side members coming together at the apex 526 of the frame. The frame 512 is preferably between about 11 to 17 inches in length in some embodiments. The frame 512 preferably elevates the neck support 528 about 0.5 to about 1.5 inches above the floor or surface. In such a configuration, the frame 512 preferably bears against the floor or surface during use and reduces the tendency of the frame to twist about its transverse axis. The cradle 538 in neck support 528 preferably tapers from an elevation of about 3 inches above the floor proximate side members 522 and 524 to a central elevation of about 2.5 inches.

The first expandable bladder 516 is preferably coupled to and carried by the neck support 528 in the cradle 538 defined therein. The first expandable bladder 516 is preferably secured in place as will be described further herein. The lateral portions 534 and 536 of neck support 528 are preferably provided with oppositely facing recesses formed therein adjacent the lateral ends of cradle 538 for receiving the extended ends of the first expandable bladder 516 to facilitate retention and alignment of the bladder on the cradle 538.

According to some embodiments, the upper portion of the first expandable bladder 516 is of a generally semi-ellipsoidal configuration having relatively pointed ends similar to the upper half of a football bladder. In one preferred bladder configuration, the underside of the first expandable bladder 516 is formed with undercut portions so as to define a central depending portion. At least a portion of the cradle is preferably configured to receive the underside of the first expandable bladder 516. Preferably, the first expandable bladder 516, when inflated, will expand upwardly from the cradle 538 to a slightly greater extent than in a transverse direction. Additionally, in some embodiments, provision of the depending portion on the underside of the bladder provides a cushioning effect under the apex of the expanded bladder which bears against the user's neck, making the device more comfortable for the user. Thus, as the bladder is inflated under and against the user's neck, it expands vertically and transversely, lifting the spine to create a spinal apex and applying an angular traction to the neck on both sides of the spinal apex. The amount of traction exerted in the vertical direction, however, will be somewhat greater than that exerted longitudinally to obtain the vertical lift necessary to restore the normal lordotic shape to the cervical region of the spine without overly tractioning the neck longitudinally.

In some embodiments, the first inflatable bladder 516 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 516 is constructed of a material that resists expansion. In some embodiments, the bladder 516 is constructed of a heat-sealable urethane with 200 Denier nylon. The bladder 516 can comprise a cover of any suitable material, including, for example, a neoprene material. The semi-ellipsoidal upper portion of the first inflatable bladder 516, when inflated, defines a transverse arc of about 4 inches in length about the center of the bladder. It is to be understood that these dimensions are by way of example only and can be varied, as can the configuration of the frame, straps, and first and second bladders without departing from the spirit and scope of the invention. For example, in some embodiments the bladder 516 can have a length of between about 6 to 9 inches, a height of about 2 to 3 inches in a deflated state, a height of about 3 to 4 inches in an inflated state. In some embodiments a deflated circumference of the bladder is about 4 inches and an inflated circumference of the bladder is between about 7 and 8 inches. In an inflated configuration, the bladder 516 can be taller than it is wide, for example, it can be approximately 4 inches tall and approximately 3 inches wide when inflated in some embodiments.

The second expandable bladder 518 is coupled to and carried by the neck support 528. The second expandable bladder 518 is preferably adjustable in some embodiments to accommodate patient anatomy and align with desired force vector directions as will be described further herein. The lateral portions 534 and 536 of neck support 528 are preferably configured with recesses formed therein for receiving the extended ends 548, for example, as described with respect to FIG. 7, of the second expandable bladder 518 to facilitate retention and alignment of the bladder on the neck support 528.

According to some embodiments, the second expandable bladder 518 is of a generally semi-ellipsoidal configuration having a relatively curved portion upon inflation for engaging a portion of the thoracic spine. Preferably, the second expandable bladder 518, when inflated, will expand about the same amount transversely and upwardly from the neck support 528. In some embodiments, the second expandable bladder 518 when inflated expands more transversely than upwardly. In some embodiments, the second expandable bladder 518 when inflated expands more upwardly than transversely. Thus, as the second expandable bladder 518 is inflated under and against the user's thoracic spine, it expands transversely and vertically, lifting the spine to counter hyper-kyphosis and applying an angular traction to the thoracic spine. The amount of traction exerted in the longitudial direction, preferably, will be similar to the amount of lift exerted vertically to obtain the necessary decompression and lift to restore the normal shape to the thoracic region of the spine.

In some embodiments, the second inflatable bladder 518 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 518 is constructed of a material that resists expansion. In some embodiments, the bladder 518 is constructed of a heat-sealable urethane with 200 Denier nylon. The bladder 518 can comprise a cover of any suitable material, including, for example, a neoprene material. The second inflatable bladder 518, when inflated, defines a transverse arc of about 4 inches in length about the center of the bladder. It is to be understood that these dimensions are by way of example only and can be varied without departing from the spirit and scope of the invention. For example, in some embodiments the bladder 518 can have a length of about 9 inches where it is coupled to the frame, a length of between about 6 and 7 inches where the bladder 518 contacts the patient. The bladder 518 can have a height of about 3 to 4 inches. The bladder 518 can have a circumference of about 6 to 7 inches.

Figure 47:
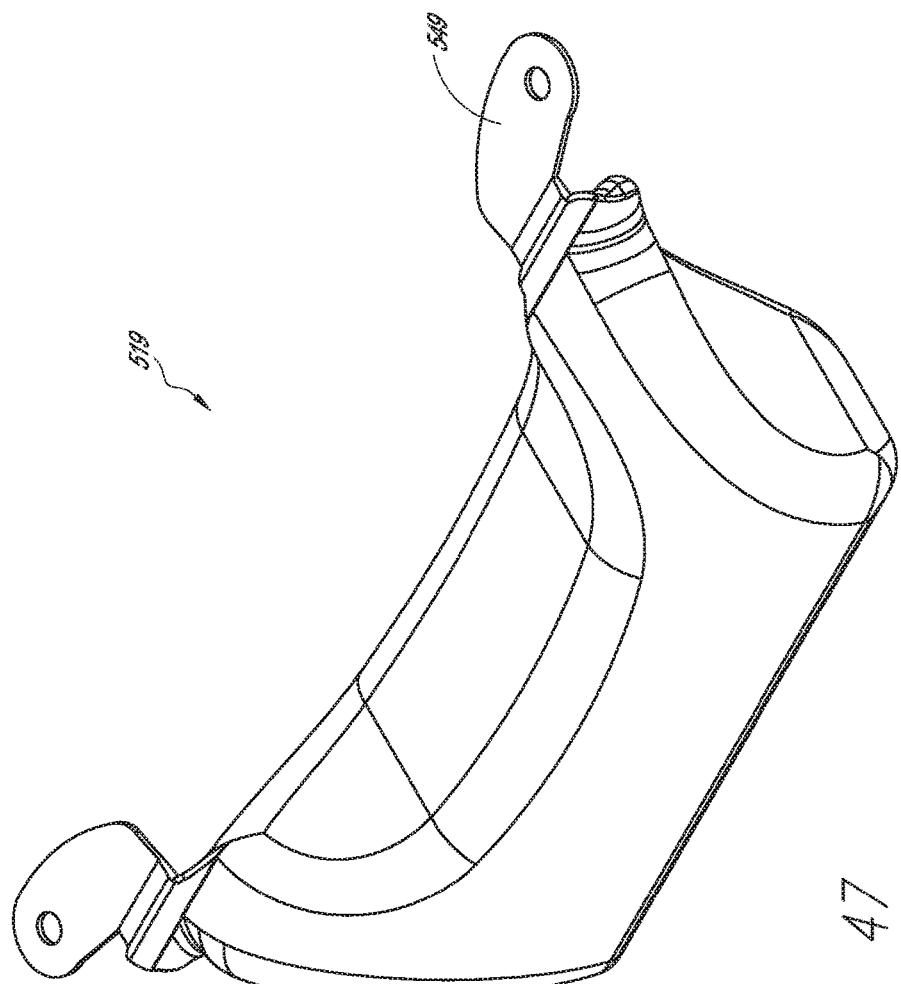
FIG. 47 is a perspective view of a portion of the system shown in FIG. 41, showing a third inflatable bladder in an unassembled configuration.

The third expandable bladder 519 is coupled to and carried by the neck support 528. The third expandable bladder 519 is preferably adjustable in some embodiments to accommodate patient anatomy and align with desired force vector directions as will be described further herein. The lateral portions 534 and 536 of neck support 528 are preferably configured with recesses formed therein for receiving the extended ends 549, shown in FIG. 47, of the third expandable bladder 519 to facilitate retention and alignment of the bladder on the neck support 528.

According to some embodiments, the third expandable bladder 519 is of a generally semi-ellipsoidal configuration having a relatively curved portion upon inflation for engaging a portion of the thoracic spine. Preferably, the third expandable bladder 519, when inflated, will expand about the same amount transversely and upwardly from the neck support 528. In some embodiments, the third expandable bladder 519 when inflated expands more transversely than upwardly. In some embodiments, the third expandable bladder 519 when inflated expands more upwardly than transversely. Thus, as the third expandable bladder 519 is inflated under and against the user's occiput, it expands transversely and vertically, lifting the occiput to apply an angular traction to the occiput. The amount of traction exerted in the longitudinal direction, preferably, will be similar to the amount of lift exerted vertically to decompress the occipital-cervical junction.

In some embodiments, the third inflatable bladder 519 is constructed of an expandable material such as neoprene rubber, defines a length of between about 8 to 10 inches, a height of about 3 to 4 inches in an uninflated state, and depending on the configuration of the bladder a transverse width of about 3 inches. In some embodiments, the bladder 519 is constructed of a material that resists expansion. In some embodiments, the bladder 519 is constructed of a heat-sealable urethane with 200 Denier nylon. The bladder 519 can comprise a cover of any suitable material, including, for example, a neoprene material. The third inflatable bladder 519, when inflated, defines a transverse arc of about 4 inches in length about the center of the bladder. It is to be understood that these dimensions are by way of example only and can be varied without departing from the spirit and scope of the invention. For example, in some embodiments the bladder 519 can have a length of about 9 inches where it is coupled to the frame, a length of between about 6 and 7 inches where the bladder 519 contacts the patient. The bladder 519 can have a height of about 3 to 4 inches. The bladder 519 can have a circumference of about 6 to 7 inches.

In some embodiments the bladders preferably have a finite shape and expand while being filled until the bladders reach the finite shape. Once the bladder has been filled to the finite shape, the pressure release valve of the pump assembly allows for gas or fluid to escape from the system to maintain a desired pressure within the bladder. The pressure release valve is preferably an automatic pressure release valve. The system preferably also comprises a manual release valve, such as a push button release valve. The desired pressure is preferably held at a proven clinical level. In some embodiments the pressure release valve is configured to maintain a pressure of about 8 psi. At a pressure of about 8 psi the system preferably provides over 50 pounds of tractional force. In some embodiments the tractional force preferably is between about 50 and 60 pounds of tractional force.

While the above described bladder configurations are preferred, it is to be understood that other configurations of expandable bladders could be employed in the present invention, either with or without an expansion controlling casing to provide the desired lifting and traction of the user's neck, spine, and head. Moreover, in some embodiments, mechanically expandable components can be used in place of the first, second, and/or third bladders. Mechanically expandable components can be coupled to the frame and selectively expanded to apply force vectors to the cervical and thoracic spine in a manner similar to those produced by the expandable bladders as described herein. For example, in some embodiments an expanding mechanical component within a cushioned cover can be selectively actuated to provide the desired force distribution.

In some embodiments, one or more of the first, second, and third expandable bladders 516, 518, and 519 are of a tubular configuration and are disposed in a non-expandable casing, preferably constructed of a vinyl or other suitable material. The casing is preferably formed in the above described generally ellipsoidal configurations. As the tubular bladder expands upon inflation, the expansion is limited by the configuration of the casing to provide the desired increase in the vertical and transverse directions.

Figure 48:
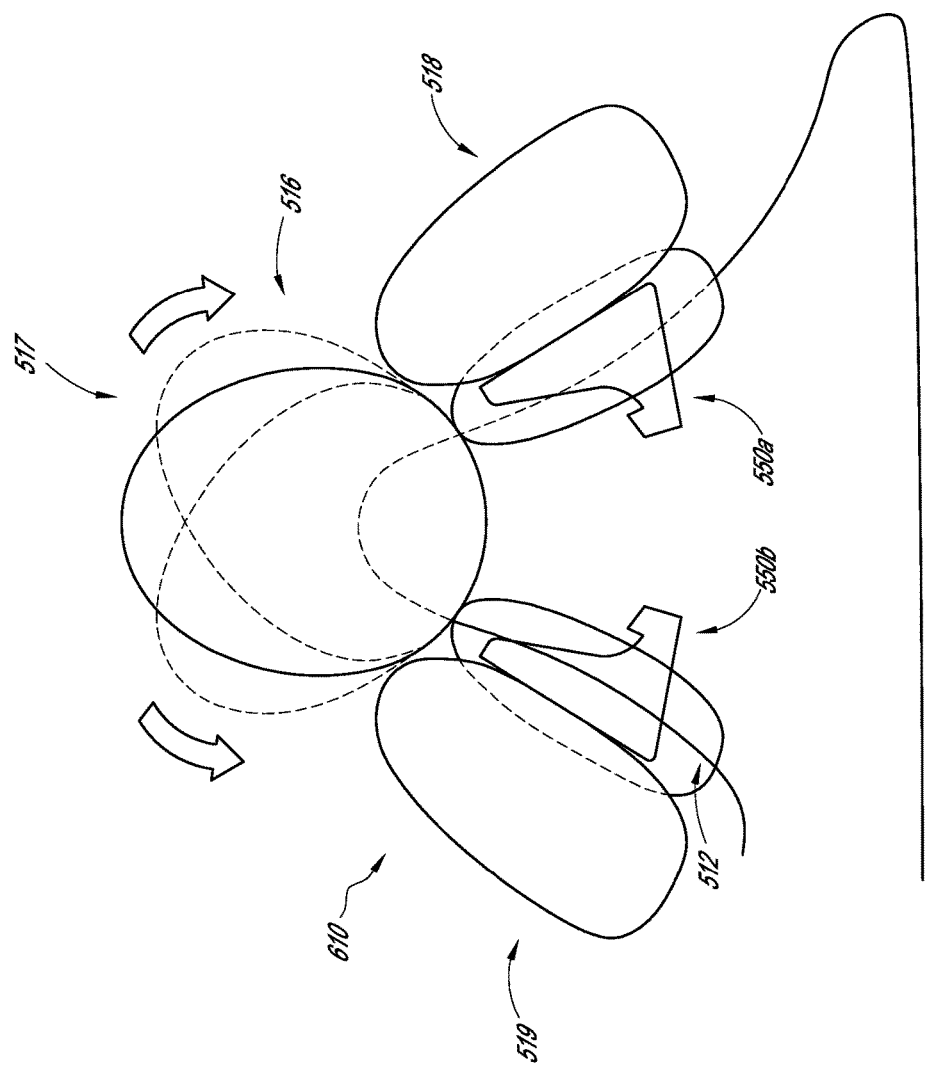
FIG. 48 is a schematic view of another embodiment of a decompression and traction system, showing mobile pneumatic air chambers comprising a first inflatable bladder being pivotably adjustable, showing a spacer component configured to be selectively coupled to the frame to adjust a position of a second inflatable bladder, and showing a spacer component configured to be selectively coupled to the frame to adjust a position of a third inflatable bladder.

In some embodiments, as shown in FIG. 48, the first expandable bladder 516 is preferably rotatably secured to the neck support 528. The first expandable bladder 516 can be tilted in a forward position, a backward position, or maintained in a central position. In some embodiments, the bladder can be locked into a desired position. Providing a rotatable first expandable bladder 516 preferably provides mobility for the pneumatic air chamber to comfortably accommodate various spinal configurations. In some embodiments, the second expandable bladder 518 can be rotatably secured to the neck support 528. In some embodiments, the third expandable bladder 519 can be rotatably secured to the neck support 528.

In some embodiments, as shown in FIG. 48, a first spacer component 550A is preferably configured to be selectively coupled to the frame 512 to adjust a position of a second inflatable bladder 518. The spacer component can be attached to the frame and can allow clinicians and users to increase the negative Y directional component of the lower pneumatic air chamber. A second spacer component 550B is preferably coupled to the frame 512 to adjust a position of the third inflatable bladder 519. The spacer component can be attached to the frame and can allow clinicians and users to increase the positive Y direction of the upper pneumatic air chamber. Each of the spacer components 550A and 550B can include the same or generally similar features as the spacer component 550 described with respect to FIGS. 8 and 9. For example, in one embodiment, each spacer component comprises an pneumatic air chamber or bladder engaging face 552, a notched connector portion 554 and opposing side portions 556. Other spacer configurations can be used to modify the directional component of the second inflatable bladder 518 and the third inflatable bladder 519.

FIGS. 49A and 49B show a patient and an embodiment of a decompression and traction system 610 having a forehead restraint, wherein the views show the decompression system 610 in an inflated configuration, respectively.

As shown in FIGS. 49A and 49B, restraint straps 558 and/or 560 can be secured at the ends thereof to one or more of slots 514. Straps can be passed under the user's chin and over the user's forehead in some embodiments. In other embodiments, a strap can be passed over the user's forehead only. The straps can be secured and fastened in any suitable manner. For example, interlocking hook and loop type fasteners, snaps, buckles or other fasteners can be used. According to some embodiments, the traction device 610 can be easily and securely affixed to the user's head with a strap configuration such that with the user lying flat on his or her back on a horizontal surface, the frame 512 rests on the surface and the neck support 528 is disposed under the user's neck and tapered ends 562 of the frame side members 522, 524 are substantially adjacent the user's shoulders and generally near the upper thoracic region. The tightness of the securement of the device 510 to the user's head can be readily adjusted as needed by the securement straps 558, 560.

In some embodiments, the system preferably comprises a frame made of virgin acrylonitrile butadiene styrene (ABS) plastic material. ABS is an engineering thermoplastic that is advantageous due to its strength, toughness, chemical resistance, and ability to maintain necessary stiffness. The expandable pneumatic air chambers are preferably made of heat-sealable urethane with 200 Denier nylon. The expandable pneumatic air chambers preferably have a neoprene cover. The facial straps are preferably made of a durable and waterproof neoprene material. The hand pump and tubing are preferably made of rubber/plastic. Other embodiments can include different materials.

According to some embodiments, the system is lightweight (for example, about 3 lbs), portable, easy to operate, requires no assembly, no weights, cables or ropes to set-up, comes with choice of ballistic nylon carrying case or educational box, instruction page and instructional DVD. In one embodiment, the device comprises a built-in frame, an expanding elliptical pneumatic air chamber (with neoprene cover) that creates radial tractional force and thoracic decompressive force, a patient-controlled pneumatic hand pump with a push button release and automatic safety valve connected to approximately 30 inches of tubing, and one dual action head restraint designed for patients who suffer with TMJ (does not aggravate temporomandibular joint), which comprises an adjustable forehead strap, and a removable chin strap (which is optional in some other embodiments).

Accordingly to one aspect disclosed herein, methods for pneumatic radial traction can restore the cervical and thoracic spine to the proper configuration. Pneumatic radial traction, also known in some embodiments as expanding ellipsoidal decompression (EED), is a process in which joints of the cervical spine are pneumatically tractioned and simultaneously aligned into the cervical spine's proper radial or curved configuration. A major clinical difference between some embodiments of a pneumatic radial traction device disclosed herein and some prior art devices is that the prior art devices flatten or reverse the proper cervical curve to attain joint separation. In some embodiments, a pneumatic radial traction device enhances or maintains the proper cervical curve while attaining over twice the joint separation as some prior art devices.

With reference to FIGS. 49A and 49B, pneumatic radial traction separates and simultaneously aligns the spinal joints in a curved or radial configuration. In some embodiments, an elliptical pneumatic air chamber directs multi-vectored expansive forces from within the posterior spinal concavity (back of neck), vertically (+Z axis translation) and in both horizontal directions. The spine is simultaneously tractioned in three main directions. The radial configuration created by these multi-vectored forces produces high level joint separation at the posterior, middle and anterior of the disc while forcefully enhancing the cervical spine's proper curve, rather than flattening or reversing the curve. Pneumatic radial traction is preferably achieved when the joints are separated by a vertical displacement greater than the horizontal displacement, however, displacement of equal height and width is also advantageous in some embodiments. An advantage of a pneumatic radial traction device is that it does not flatten or reverse the proper cervical curve while attaining joint separation. In some embodiments, the system provides a traction device with multiple fulcrums. For example, at least two fulcrums, and preferably three fulcrums, are provided to provide treatment to the cervical spine, thoracic spine, and occiputal-cervical junction of the patient.

As the head is stabilized in the cervical device, joints are actively tractioned in 3 main directions instead of one or two. The cervical spine is tractioned vertically along the +Z axis with a pneumatic force of over 58 lbs. This force expands into and against the posterior cervical concavity. Simultaneously the spine is tractioned horizontally in the two traditional directions (+Y and −Y) with a pneumatic force of over 40-lbs in each direction. These forces expand against the occiput and against the upper thoracic region. The combination of these simultaneously applied pneumatic forces produce radial traction. When fully inflated the elliptical pneumatic cell expands to a 7.5 inch radius, affecting the entire cervical spine. High level joint traction occurs at the posterior, center and anterior aspect of the vertebral bodies in a ratio coinciding with the discs' natural wedged spacing. While the pneumatic radial traction device separates the posterior of the joints to a magnitude typical of traditional traction, it separates the overall disc more than twice as much as linear traction.

With the simultaneous application of three separate pneumatic air chambers the cervical spine is decompressed into its proper lordotic or curved configuration (<∧>) with −Y +Z +Y force vectors while the hyper kyphotic area of the upper thoracic spine is simultaneously decompressed with a combination +Z/−Y force mid-vector and the occiputal-cervical junction is simultaneously decompressed with +Z/+Y force vectors. The cervical spine's lordotic curve is powerfully decompressed and enhanced while the thoracic hyper-kyphosis is simultaneously reduced and the occipital-cervical junction is decompressed. In certain embodiments, 15° to 20° of forward head flexion can be imparted by the application of +Z/+Y force vectors to the occiput.

Continuous expansion and contraction of the pneumatic air chambers can be employed to create alternating hydration and milking of the intervertebral discs, activating their sponge-like imbibition action. Holding the air pressure constant over a period of 15 to 20 minutes has the effect of simultaneously molding the spine into a curved or elliptical shape, decompressing discs and relaxing the dura, cord and nerve-roots in the cervical canal.

Embodiments described herein are preferably prescribed for patients with chronic neck pain due to a musculoskeletal or neurological impairment. The system applies radial tractional force to the cervical spine, enhancing the cervical lordotic curve while achieving high level joint separation at the anterior, center and posterior aspect of the vertebral bodies and discs in a ratio corresponding with their natural wedged spacing, reducing disc protrusions, compression and increasing range of motion. The system further applies angular traction forces to the occiput, achieving decompression of the occipital-cervical junction. In some applications, devices advantageously decrease pain in chronic neck pain patients, decrease headaches and increase range of motion while reducing the necessity for chronic pain medication and neck surgery.

With continued reference to FIGS. 49A and 49B, according to some embodiments in use, the traction device 510 rests on a horizontal surface such that the neck support 528 projects upwardly therefrom. The user lies on the device in a prone position such that the back of the neck rests on the deflated first expandable bladder 516 carried in the cradle 538 of the neck support 528. The deflated second expandable bladder 518 is positioned between the neck support 528 and portions of the thoracic spine of the user. The deflated third expandable bladder 519 is positioned between the neck support 528 and the occiput of the user. The chin and/or forehead restraining restraint straps are respectively extended under the user's chin and/or about the user's forehead and secured, thereby affixing the traction device 510 to the user such that the neck and cervical spine extend over the neck support and first expandable bladder 516, the thoracic spine is adjacent the second expandable bladder 518, and the occiput is adjacent the third expandable bladder 519. According to one preferred embodiment, the outward extension of the neck support 528 is relatively slight so that when the bladder is in the deflated position with the forehead and chin restraints secured, very little or no force is exerted on the neck by the neck support. This is achieved by elevating the neck support 528 above the frame such that the neck cradle 538 formed therein is about 2 to 3 inches above the floor or other horizontal surface on which the device 510 is used. The first expandable bladder 516 is sized such that upon full inflation, the apex of the curved upper surface of the bladder will extend about 5 inches above the floor or surface. The second expandable bladder 518 is sized such that upon full inflation, a surface of the second expandable bladder engaging the thoracic spine will extend toward the thoracic spine about 2 to 3 inches in the −Y/+Z direction. In certain embodiments, the second expandable bladder 518 is sized and/or positioned such that during inflation, a surface of the second expandable bladder 518 engaging the thoracic spine will impart a force to the thoracic spine in the −Y direction during a first period of inflation and will impart a force to the thoracic spine in the −Y/+Z direction during a second period of inflation following the first period of inflation. In certain embodiments, the expandable bladder 518 is sized and/or positioned such that upon full inflation, a surface of the expandable bladder 518 engaging the thoracic spine will impart a force to the thoracic spine in the −Y direction. The third expandable bladder 519 is sized such that upon inflation, a surface of the third expandable bladder engaging the occiput will extend toward the occiput about 2 to 3 inches in the +Y/+Z direction. Upon inflation, the third expandable bladder 519 can impart 15° to 20° of forward head flexion. In certain embodiments, the third expandable bladder 519 is sized and/or positioned such that during inflation, a surface of the third expandable bladder 519 engaging the occiput will impart a force to the occiput in the +Y direction during a first period of inflation and will impart a force to the occiput in the +Y/+Z direction during a second period of inflation following the first period of inflation. In certain embodiments, the expandable bladder 519 is sized and/or positioned such that upon full inflation, a surface of the expandable bladder 519 engaging the occiput will impart a force to the thoracic spine in the +Y direction.

In some embodiments, as the user slowly inflates the first, second, and third inflatable bladders 516, 518, and 519 using the air pump 542, the first inflatable bladder 516 expands upwardly and, to a lesser extent, transversely, thereby forcing the cervical spine forwardly creating a spinal apex while concurrently stretching the spine angularly along both sides of the formed spinal apex. The second inflatable bladder 518 expands transversely in the −Y direction, thereby forcing the thoracic spine forwardly to offset the effects of hyperkhyphosis. The third inflatable platter expands transversely in the +Y direction, thereby forcing the occiput forwardly and upwardly to create radial traction to attain joint separation of the occipital-cervical junction. The user then continues to inflate the first, second, and third bladders 516, 518, and 519 until his or her individual tolerance level is reached. The bladders are then deflated by use of the one way valve 544. The process is preferably repeated several times, slowly increasing the spinal arc in the cervical region and placing pressure on the thoracic region as the level of tolerance increases. In addition, the first, second, and third bladders 516, 518, and 519 can be held in an inflated state at or slightly below the level of tolerance for varying periods of time up to ten to twenty minutes. Through such repetition, the cervical spine, thoracic spine and surrounding tissue receive a workout promoting cellular exchange in and around the intervertebral disc and a forward curve is reinstated into the cervical spine while achieving proper spine configuration in the thoracic region. FIGS. 49A and 49B illustrate the effects of the traction and exercise devices 610 of some embodiments on the cervical and thoracic spine.

Figure 50:
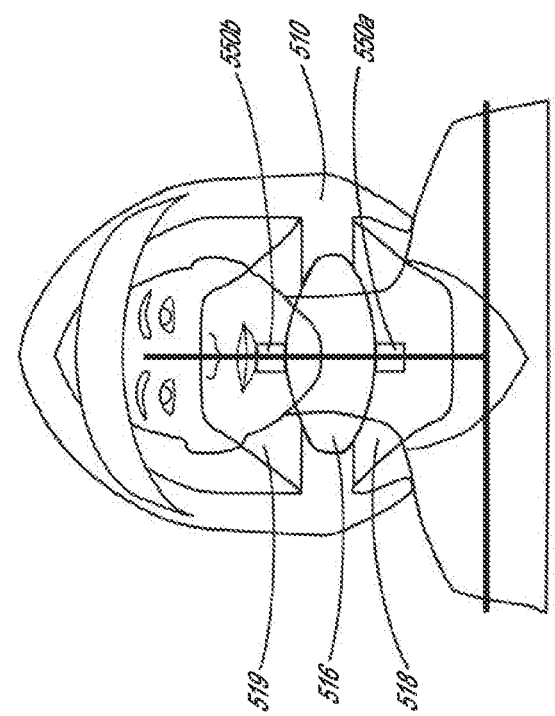
FIG. 50 is a schematic top view of a patient positioned on another embodiment of a decompression and traction system, showing pneumatic air chambers comprising first, second, and third inflatable bladders, a first adjustable spacer component configured to be selectively coupled to the frame to adjust a position of the second inflatable bladder, wherein in the shown configuration the spacer component adjusts the position of the second inflatable bladder to provide an even distribution of force generally along a force vector in the −Y and +Z plane, and a second adjustable spacer component configured to be selectively coupled to the frame to adjust a position of the third inflatable bladder, wherein in the shown configuration the spacer component adjusts the position of the third inflatable bladder to provide an even distribution of force generally along a force vector in the +Y and +Z plane

With reference to FIGS. 50-53, an adjustable spacer component 550A and a spacer component 550B can be provided in some implementations of a traction system 510 to provide for lateral flexion traction. For example, FIG. 50 is a schematic top view of a patient positioned on another embodiment of a decompression and traction system, showing pneumatic air chambers comprising first, second, and third inflatable bladders 516, 518, and 519, a first adjustable wedge-shaped spacer component 550A configured to be selectively coupled to the frame to adjust a position of the second inflatable bladder, and a second adjustable wedge-shaped spacer component 550B configured to be selectively coupled to the frame to adjust a position of the third inflatable bladder. In the shown configuration, the first spacer component 550A is in a vertical orientation and adjusts the position of the second inflatable bladder to provide an even distribution of force generally along a force vector in the −Y and +Z plane without providing any lateral flexion traction to the patient. In the shown configuration, the second spacer component 550B is in a vertical orientation and adjusts the position of the third inflatable bladder to provide an even distribution of force generally along a force vector in the +Y and +Z plane without providing any lateral flexion traction to the patient.

Figure 51:
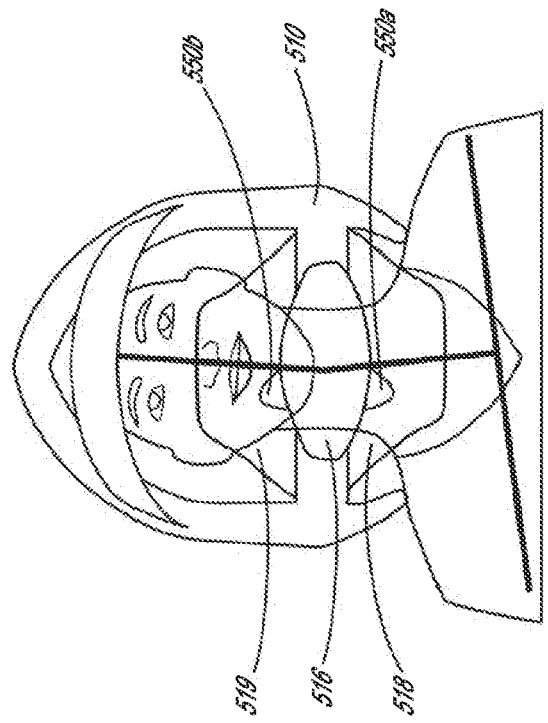
FIG. 51 is a schematic top view of a patient and the embodiment of FIG. 50, showing a configuration wherein the first spacer component is moved to adjust the position of the second inflatable bladder to provide an uneven distribution of force on one side of the patient in that a force vector is directed, for example, in a −Y, +Z, and −X direction, and wherein the second spacer component is moved to adjust the position of the third inflatable bladder to provide an uneven distribution of force on one side of the patient in that a force vector is directed, for example, in a +Y, +Z, and −X direction.

FIG. 51 shows a configuration wherein the first spacer component 550A is moved to adjust the position of the second inflatable bladder to provide an uneven distribution of force on one side of the patient in that a force vector is directed, for example, in a −Y, +Z, and −X direction. For example, the spacer component is turned or rotated to a horizontal position, whereby the wedge shape of the spacer contacts the second inflatable bladder and causes the bladder to deflect in one lateral direction more than another lateral direction. As shown, the spacer is placed in right horizontal position and causes more deflection on the right side of the patient. In other configurations, the spacer can be positioned in a left horizontal position to cause more deflection on the left side of the patient. Based on the positioning of the spacer, the second bladder can expand in an angular direction. Turning the spacer component sideways creates lateral flexion traction by forcing the shoulder/trapezius down while the head is held in traction.

In the configuration shown in FIG. 51, the second spacer component 550B is moved to adjust the position of the third inflatable bladder to provide an uneven distribution of force on one side of the patient in that a force vector is directed, for example, in a +Y, +Z, and −X direction. For example, the spacer component is turned or rotated to a horizontal position, whereby the wedge shape of the spacer contacts the third inflatable bladder and causes the bladder to deflect in one lateral direction more than another lateral direction. As shown, the spacer is placed in right horizontal position and causes more deflection on the right side of the patient. In other configurations, the spacer can be positioned in a left horizontal position to cause more deflection on the left side of the patient. Based on the positioning of the spacer, the third bladder can expand in an angular direction. Turning the spacer component sideways creates lateral flexion traction by forcing the head up while the shoulder/trapezius is held in traction. In certain embodiments, the spacer component 550B can be moved to adjust the position of the third inflatable bladder to provide an uneven force distribution of force on one side of the patient, as described herein, to treat a misalignment or deformity of the spine which causes the cervical spine to angle or curve in the +X or −X direction. For example, if the cervical spine of a patient is angled or curved in the +X direction, a −X force can be imparted to restore the cervical spine to its proper configuration. If the cervical spine of a patient is angled or curved in the −X direction, a +X force can be imparted to restore the cervical spine to its proper configuration.

Figure 53:
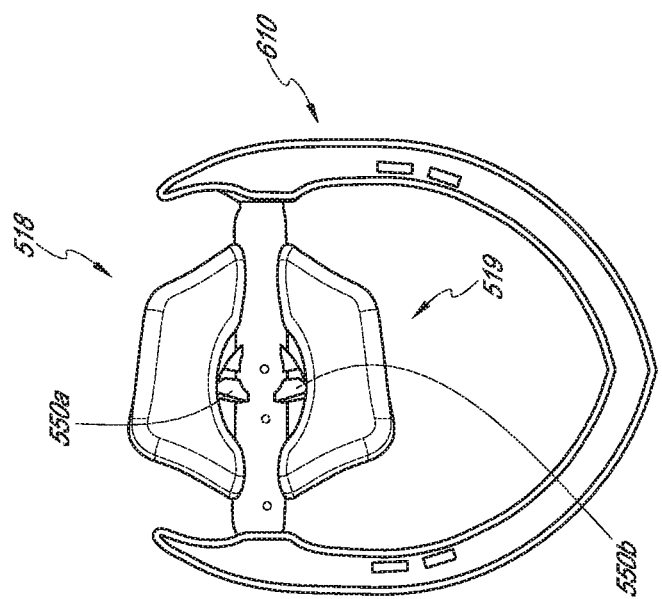
FIG. 53 is a bottom view of the embodiment of FIG. 50, showing a configuration wherein the first spacer component is moved to adjust the position of the second inflatable bladder to provide an uneven distribution of force to a patient in that a force vector is directed, for example, in a −Y, +Z, and −X direction and the second spacer component is moved to adjust the position of the third inflatable bladder to provide an uneven distribution of force to a patient in that a force vector is directed, for example, in a +Y, +Z, and −X direction.
Figure 52:
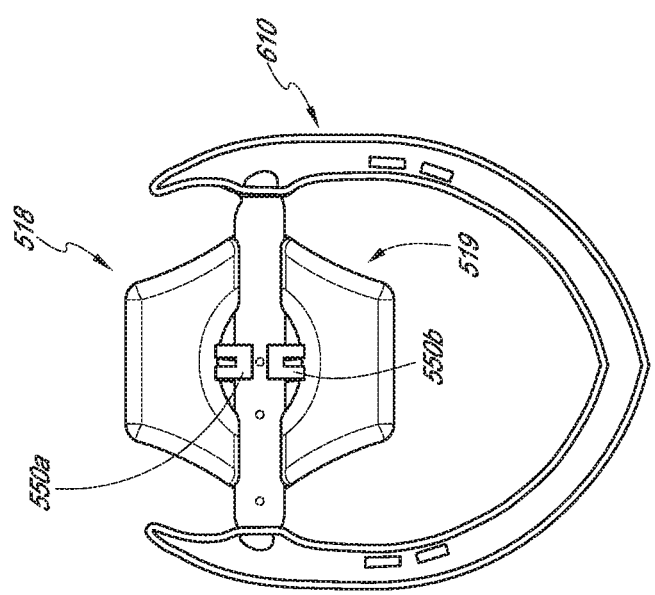
FIG. 52 is a bottom view of the embodiment of FIG. 50, in the shown configuration the first spacer component adjusts the position of the second inflatable bladder to provide an even distribution of force generally along a force vector in the −Y and +Z plane and the second spacer component adjusts the position of the second inflatable bladder to provide an even distribution of force generally along a force vector in the +Y and +Z plane.

FIG. 52 is a bottom view of the embodiment of FIG. 50 and shows the spacer component 550A in a vertical position that adjusts the position of the second inflatable bladder to provide an even distribution of force generally along a force vector in the −Y and +Z plane, but does not direct force laterally in a −X or +X direction. FIG. 52 shows the spacer component 550B in a vertical position that adjusts the position of the third inflatable bladder to provide an even distribution of force generally along a force vector in the +Y and +Z plane, but does not direct force laterally in a −X or +X direction. FIG. 53 is a bottom view of the embodiment of FIG. 50, showing a configuration wherein the first spacer component 550A is moved to adjust the position of the second inflatable bladder to provide an uneven distribution of force to a patient in that a force vector is directed, for example, in a Y, +Z, and −X direction as described in connection with FIG. 51. The lower linear displacement pneumatic air chamber is adjusted with a rotating wedge shaped spacer component, allowing clinicians to increase the angle and force of the mid (−Y)/(+Z) vector of this pneumatic air chamber. When adjusted to the right or left horizontal position, the rotating wedge allows clinicians to unilaterally increase and rotate the (−Y) directional component on either the right or left side (+/−X) of the upper thoracic region, producing lateral flexion traction. The rotating wedge shaped spacer component can be removed in some implementations to accommodate extreme kyphotic thoracic spines. In the configuration of FIG. 53, the second spacer component 550B is moved to adjust the position of the third inflatable bladder to provide an uneven distribution of force to a patient in that a force vector is directed, for example, in a +Y, Z, and −X direction as described in connection with FIG. 51. The upper linear displacement pneumatic air chamber is adjusted with a rotating wedge shaped spacer component allowing clinicians to increase the angle and force of the mid (+Y)/(+Z) vector of this pneumatic air chamber. When adjusted to the right or left horizontal position, the rotating wedge allows clinicians to unilaterally increase and rotate the (+Y) directional component on either the right or left side (+/−X) of the occiput, producing lateral flexion traction. The rotating wedge shaped spacer component can be removed in some implementations.

Figure 54:
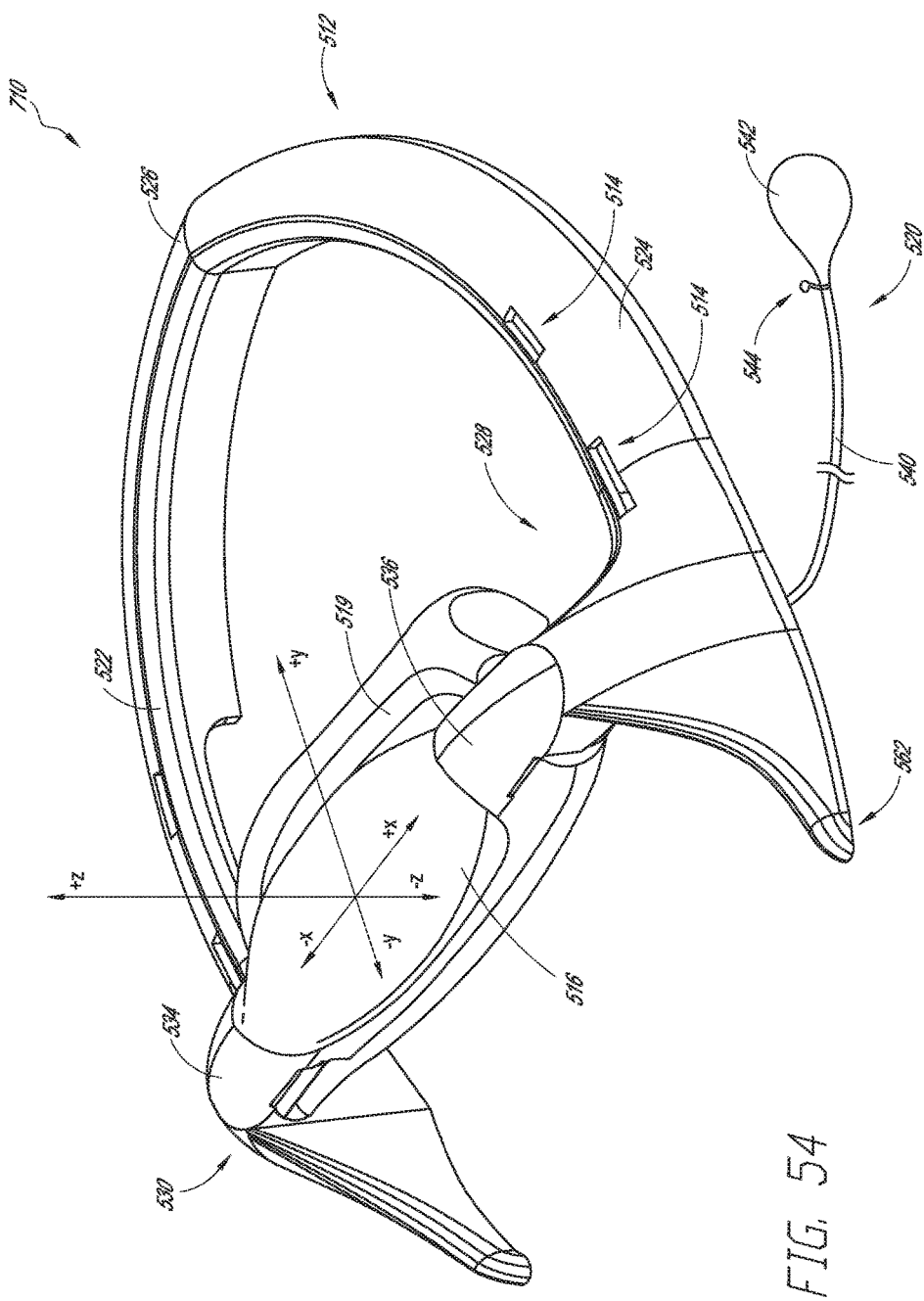
FIG. 54 is a perspective view of one embodiment of a decompression and traction system.

While three expandable bladders 516, 518, and 519 are described with respect to FIGS. 41-53, certain embodiments may employ only two of the inflatable bladders 516, 518, and 519, as shown in FIGS. 27-40, or only one of the inflatable bladders 516, 518, and 519. For example, in some embodiments, a decompression and traction system 710 may include only the first inflatable bladder 516 and the third inflatable bladder 519 as shown in FIG. 54. Such an embodiment may be less expensive to manufacture than an embodiment having three inflatable bladders. As described herein, the first inflatable bladder 516 and third inflatable bladder 519 can be employed to apply −Y +Z +Y force vectors to the cervical spine while +Z/+Y force vectors are applied to the occiput. The cervical spine's lordotic curve is powerfully decompressed and enhanced while the occipital-cervical junction is decompressed. Such an embodiment may be advantageous if treatment of the thoracic spine is not desired. For example, in some embodiments, damage to the thoracic spine or an obstruction, such as a tumor or implant, may make the application of force to the thoracic spine undesirable. The system 710 may be utilized to treat symptoms associated with compression, damage, deformity, and/or misalignment of the cervical spine and the occipital-cervical junction, including, for example, headaches, neck pain, and arm pain, which may be caused by pinched nerves. In certain embodiments, the decompression and traction system 710 can include a spacer component 550B as described with respect to the decompression and traction system 210 as shown in FIGS. 41-53.

In some embodiments, a similar application of force can be imparted by the system 610 through selective inflation of the bladders 519 and 516 without inflation of the bladder 518 or with minimal inflation of the bladder 518. As described herein, in some embodiments, a two pump system or a three pump system can be employed to alternate or unevenly inflate the pneumatic air chambers. For example, in some embodiments, a first pump can be employed to inflate the first and third inflatable bladders 516 and 519 and a second pump can be employed to inflate the second inflatable bladder 518.

Figure 55:
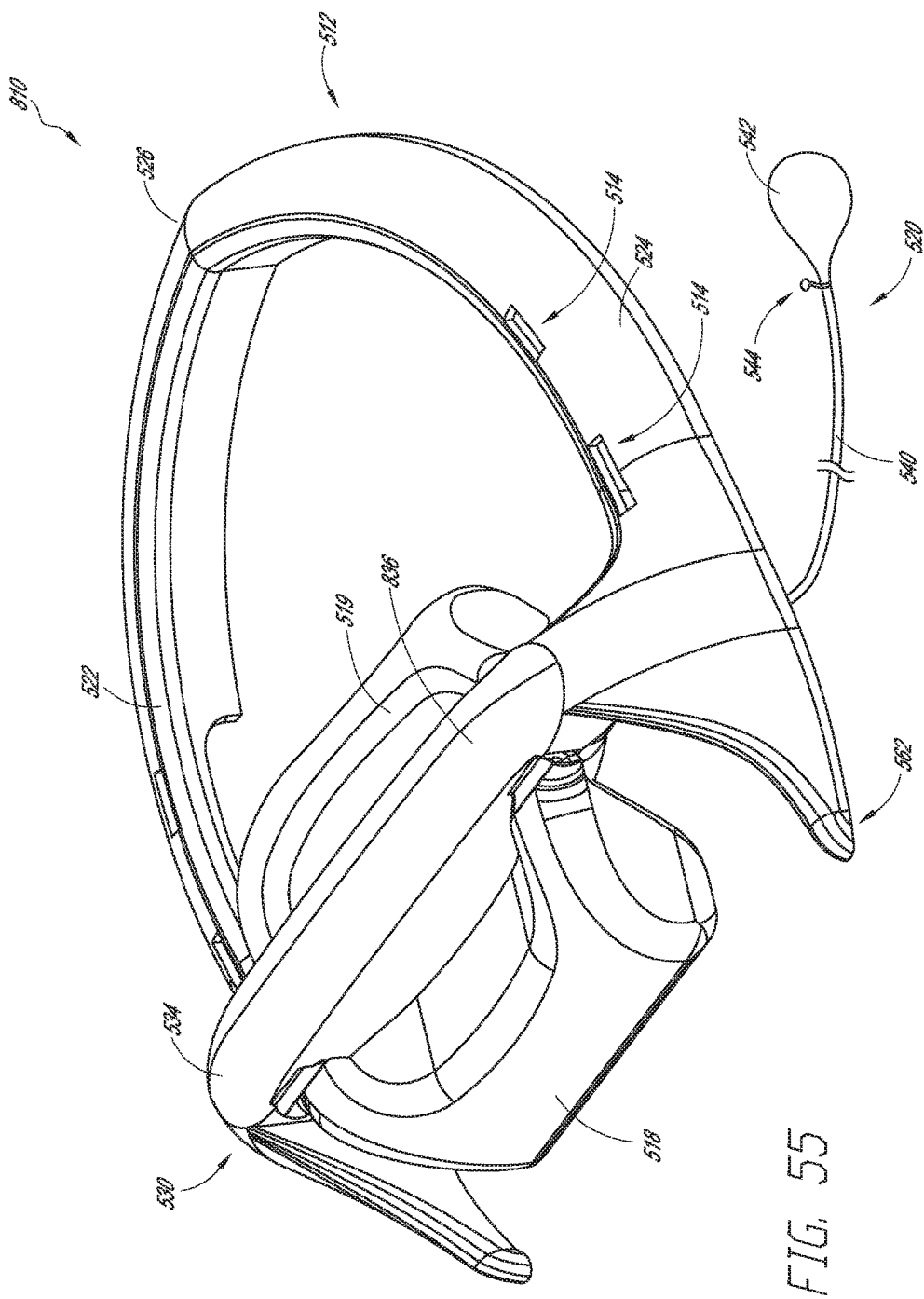
FIG. 55 is a perspective view of one embodiment of a decompression and traction system.

In some embodiments, a decompression and traction system 810 may include only the second inflatable bladder 518 and the third inflatable bladder 519 as shown in FIG. 55. Such an embodiment may be less expensive to manufacture than an embodiment having three inflatable bladders. In some embodiments, the system 810 includes a pad or cushion 836 configured to be positioned against the cervical spine when the system 810 is secured to a user. As described herein, the second bladder 518 and third inflatable bladder 519 can be employed to decompress a hyper kyphotic area of the upper thoracic spine with a combination +Z/−Y force mid-vector while +Z/+Y force vectors are simultaneously applied to the occiput to decompress the occipital-cervical junction. Thoracic hyper-kyphosis is simultaneously reduced while the occipital-cervical junction is decompressed. In certain embodiments, the second inflatable bladder 518 can be employed to apply a −Y force vector to the upper thoracic spine, and the third inflatable bladder 519 can be employed to apply a +Y force vector to the occipital-cervical junction. In some embodiments, the system 710 can be used to impart linear traction to the spine. In certain embodiments, the decompression and traction system 810 can include a spacer component 550A as described with respect to the decompression and traction system 610 as shown in FIGS. 41-53. In certain embodiments, the decompression and traction system 810 can include a spacer component 550B as described with respect to the decompression and traction system 610 as shown in FIGS. 41-53.

In some embodiments, a similar application of force can be imparted by the system 610 through selective inflation of the bladders 519 and 518 without inflation of the bladder 516 or with minimal inflation of the bladder 516. As described herein, in some embodiments, a two pump system or a three pump system can be employed to alternate or unevenly inflate the pneumatic air chambers. For example, in some embodiments, a first pump can be employed to inflate the second and third inflatable bladders 518 and 519 and a second pump can be employed to inflate the first inflatable bladder 516. By inflating the bladders 519 and 518 without inflating the bladder 516 or with minimal inflation of the bladder 516, linear traction can be imparted to the spine.

Figure 56:
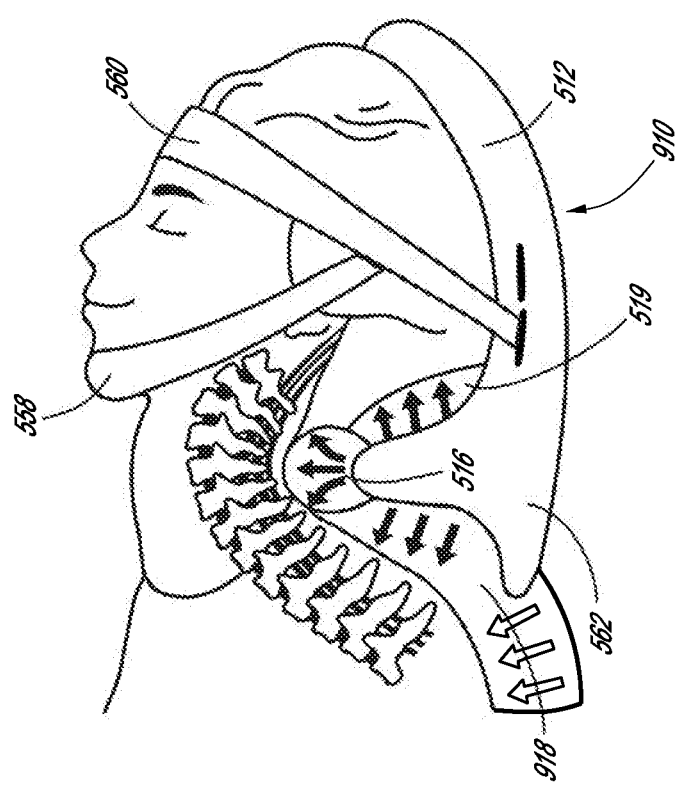
FIG. 56 is an illustrative view of a patient's spine including an embodiment of a decompression and traction systems in use in an inflated configuration.

FIG. 56 shows a patient and an embodiment of a decompression and traction system 910 having an elongated inflatable bladder 918. The elongated inflatable bladder 918 can extend from the neck support to the mid-thoracic spine when the decompression and traction system 910 is secured to the user. In some embodiments as described herein, the mid-thoracic spine can include the T4-T9 vertebrae, the T5-T8 vertebrae, or the T6-T7 vertebrae. In addition to the application of forces to the upper thoracic spine, as described herein, the inflatable bladder 918 can be configured for inflation and simultaneous application of force to the mid-thoracic spine, when the patient is in a treatment position, to decompress the spine into its proper curved configuration with a +Z force vector, and in some embodiments, −Y and/or +Y force vectors, being applied to the mid-thoracic spine. The elongated inflatable bladder 918 can apply pressure to the apex of the kyphosis of the thoracic spine. In some embodiments, the thoracic hyper-kyphosis can be further reduced by the application of force to the mid-thoracic spine. The elongated bladder 918 can directly contact the upper 25%-75% of the thoracic spine. In certain embodiments, the elongated bladder 518 can directly contact the upper 25% to 45%, upper 25% to 50%, upper 25% to 55%, upper 25% to 60%, upper 25% to 65%, or upper 25% to 70% of the thoracic spine. In certain embodiments, the elongated bladder 518 can directly contact the upper 50% of the thoracic spine.

As described herein, the inflatable bladder 918 can be inflated using a pump assembly. A pump for inflation of the inflatable bladder 918 can be the same as or a separate pump from one or more pumps used for inflation of the inflatable bladders 516 and 519. In some embodiments, two or more pumps can be employed to alternate or unevenly inflate portions of the elongated inflatable bladder 918. For example, in some embodiments, a first pump can be employed to inflate a first portion of the elongated inflatable bladder 918 positioned to apply a force to the upper thoracic spine and a second pump can be employed to inflate a second portion of the elongated inflatable bladder 918 positioned to apply a force to the mid-thoracic spine. Although a single elongated inflatable bladder 918 is shown in FIG. 56, in some embodiments, a separate inflatable bladder may be employed to apply a force to the mid-thoracic spine. In such embodiments, the separate inflatable bladder configured to apply a force to the mid-thoracic spine can be inflated using a pump that can be separate from or shared with the inflatable bladder positioned to apply a force to the upper thoracic spine.

In certain embodiments, the decompression and traction system 910 can include one or more spacer components having the same or similar features to spacer components 550, 550A, and 550B. For example, in some embodiments, the decompression and traction system 510 can include a spacer between a portion of the frame 512 and the elongated inflatable bladder 518. The spacer can be employed to adjust the angulation of the inflatable bladder 518 during inflation. In certain embodiments, the decompression and traction system 510 can include a spacer between a portion of the frame 512 and the inflatable bladder 519. The spacer can be employed to adjust the angulation of the inflatable bladder 519 during inflation. Spacers used in the decompression and traction system 510 can include a wedge-shaped spacer, a rotatable spacer, and/or a spacer in a horizontal position that is configured to adjust the angulation of the inflatable bladder portion 519 or the inflatable bladder portion 518 during inflation to provide lateral flexion traction. Other spacer systems are contemplated and can also be used. For example, any component or device that can be selectively adjusted and can contact at least a portion of the inflatable bladder portion 519 and/or the inflatable bladder portion 518 can be used to impart lateral flexion traction. Additionally, in some cases a component or device need not be adjustable, for example, a spacer or other component could be provided on a traction device to cause the inflatable bladder portion 519 and/or the inflatable bladder portion 518 to consistently provide for lateral flexion traction on one side, while other systems can provide for lateral flexion traction on the other side. Additionally, while adjustments made with the spacer may be rotational, other movements or adjustments can be made with other mechanisms and arrangements, such as by sliding, for example.

While three expandable bladders 516, 918, and 519 are described with respect to FIG. 56, certain embodiments may employ only the elongated inflatable bladder portion 918 or only the elongated inflatable bladder portion 918 and one of the inflatable bladder portion 516 and the inflatable bladder portion 519.

In some embodiments, an embodiment of a decompression and traction system as described with respect to FIGS. 27-55, can be used in combination with an embodiment of an abdominal muscle and spine exercising device as described with respect to FIGS. 1-8, and/or in combination with an embodiment of a lower body and spinal exercise device as described with respect to FIGS. 9-26.

Figure 57:
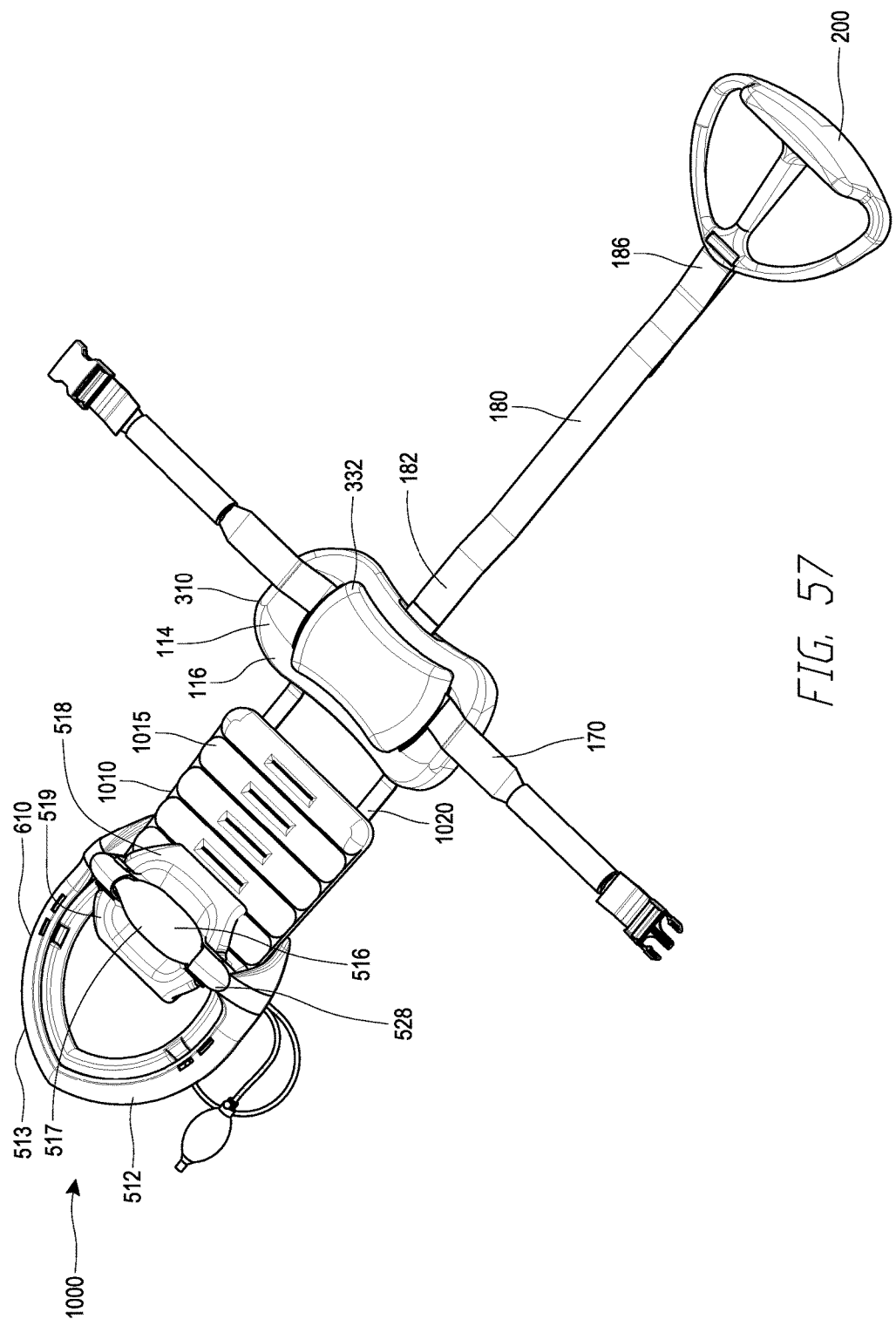
FIG. 57 is a perspective view of one embodiment of a decompression, traction, and lower body exercise system in accordance with the present invention.

FIG. 57 depicts an embodiment of a spinal treatment system 1000 comprising a traction device 610 and an exercise device 310. The traction device 610 can be coupled to a cushion or pad 1010. The cushion 1010 can include a portion extending beyond the bladder 519 in the +y direction. The cushion 1010 can also include a portion extending beyond the bladder 518 in the −y direction. The cushion 1010 can be positioned to provide comfort and support to the head and upper/mid thoracic spine of the user during spinal traction/exercise. The cushion 1010 can include a plurality of cushion sections 1015. In some embodiments, one or more of the cushion sections 1015 may be inflatable bladder sections 1015. The inflatable bladder sections 1015 may be inflatable to apply force to the mid-thoracic spine, when the patient is in a treatment position, to decompress the spine into its proper curved configuration with a +Z force vector, and in some embodiments, −Y and/or +Y force vectors, being applied to the mid-thoracic spine. In certain embodiments, one or more of the cushion sections 1015 can be pad sections 1015. The pad sections 1015 can be shaped and/or dimensioned to apply force to the mid thoracic spine, when the patient is in a treatment position, to decompress the spine into its proper curved configuration with a +Z force vector, and in some embodiments, −Y and/or +Y force vectors, being applied to the mid-thoracic spine. The pad sections 1015 can be formed of any of the materials and/or have any of the same material properties as the pads 332, 432, and 434.

The exercise device 310 can be coupled to the traction device 610 through one or more straps 1020. As shown in FIG. 57, the straps extend between the cushion 1010 and the frame 114 of the exercise device 310. The straps 1020 may be adhered, integrally formed with, or otherwise attached to the cushion 1010. In some embodiments, the straps 1020 may extend through one or more slots within the cushion 1010 and may include a loop for fastening an portion of the strap 1020 to the cushion 1010. The straps 1020 may be adhered, integrally formed with, or otherwise attached to the cushion frame 114 of the device 310. In some embodiments, the straps 1020 may extend through one or more slots within the frame 114 and may include a loop for fastening an portion of the strap 1020 to the frame 114. In alternative embodiments, one or more straps 1020 may connect directly to the traction device 610.

The system 1000 can provide for full spinal traction. In combination, the exercise device 310 and traction device 610 cause traction in both the lumbosacral and cervicothoracic regions of the spine. The combination of the exercise device 310 and traction device 610 can cause hydration of more spinal discs simultaneously than either the exercise device 310 or traction device 610 alone, allowing for more efficient and less time consuming treatment of the spine. The combination of the exercise device 310 and traction device 610 may also maintain a proper posture of a patient during traction of the lumbosacral region.

Although FIG. 57 depicts the exercise device 310 coupled to the traction device 610, one of skill in the art would understand that any of the traction devices 510, 610, 710, and 810 may be coupled to any of the exercise devices 10, 110, 210, and 310. In certain embodiments, exercise device 210 may be coupled with a traction device 510, 610, 710, or 810, without the stirrup 200 and elongate strap 180. Similarly, in certain embodiments, exercise device 310 may be coupled with a traction device 510, 610, 710, or 810, without the stirrup 200 and elongate strap 180.

Figure 58:
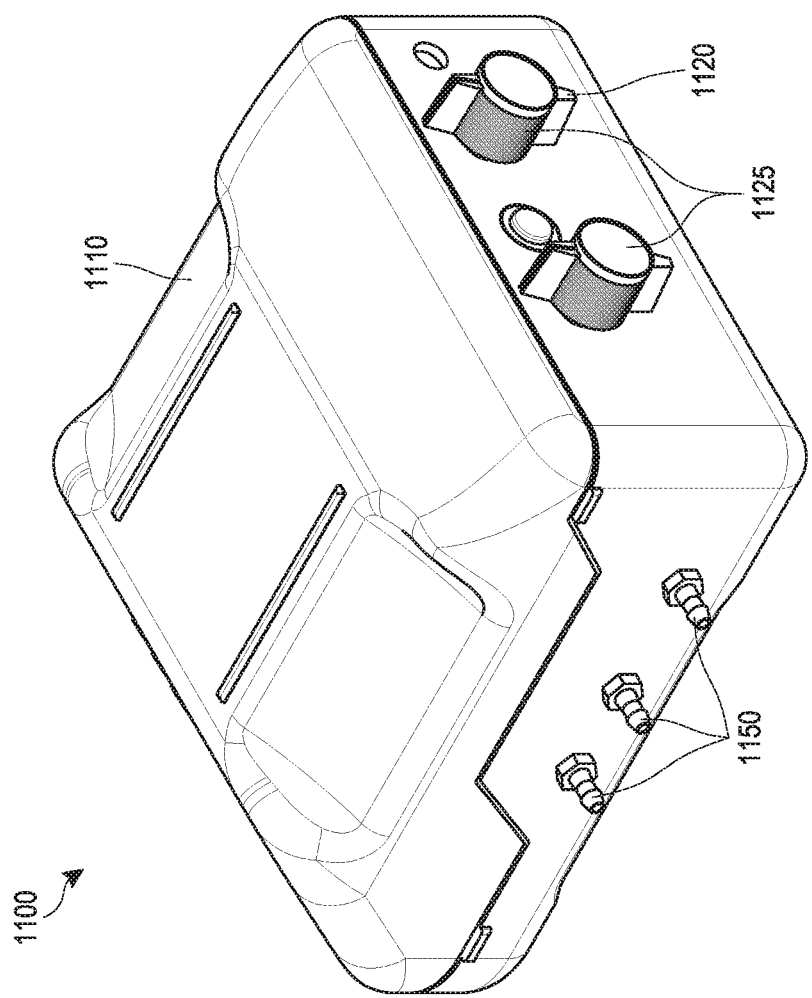
FIG. 58 is a perspective view of an embodiment of an automated pump system in accordance with the present invention.
Figure 59:
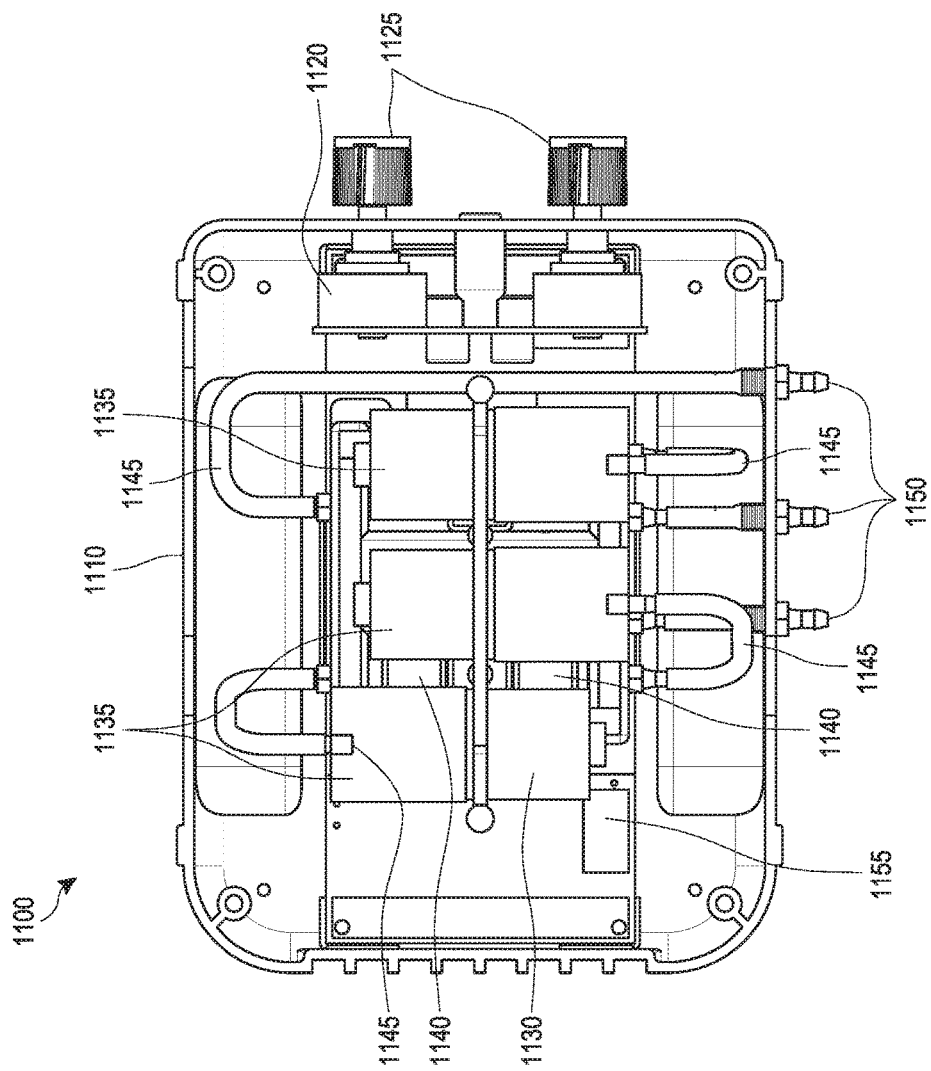
FIG. 59 is a top view of the pump system of FIG. 58 with a portion of a housing of the pump system removed to show internal features.

FIG. 58 depicts a perspective view of an embodiment of an automated or electronic pump system 1100. FIG. 59 shows a top view of the pump system 1100 with a portion of a housing 1110 of the pump system removed to show internal features of the pump system 1100. The pump system 1100 includes a user interface 1120 that allows a user to select and/or control one or more settings of the pump system 1100.

The pump system 1100 further includes a fluid delivery system 1130, which may be a pneumatic or hydraulic system. The fluid delivery system 1130 can include one or more motors 1135, for example, one or more air motors, one or more valves 1140, for example, one or more pnuetronics valves or solenoid valves, and one or more tubes or pipes 1145.

The fluid delivery system 1130 is configured to direct the flow of fluid through the tubes 1145 and to one or more connection fittings 1150. Each fitting 1150 can be configured to couple with a fluid line to deliver fluid therethrough to an inflatable.

The pump system 1100 may further include a processor 1155 in connection with the user interface 1120 and the fluid delivery system 1130. The processor 1155 can be configured to process data received from the user interface 1120. The processor 1155 can be further configured to execute one or more software applications that cause the pump 1100 to fill one or more inflatables coupled to the pump 1100. In some embodiments, the processor 1155 can be configured to cause the pump 1100 to activate and/or control the fluid delivery system 1130 to deliver fluid through the fittings 1150. For example, the processor 1155 may activate and/or control one or more of the motors 1135 to cause fluid to flow through one or more of the fittings 1130.

In certain embodiments, the pump 1100 can be configured to inflate one or more inflatables to one or more the predefined or user selected inflation amounts. In certain embodiments, the user interface 1120 can be manipulated to adjust an amount of fluid or rate of flow through one or more of the fluid fittings 1150 from the pump system 1100. The processor 1155 can be configured to cause the fluid delivery system 1130 to deliver a selected amount of fluid through the fittings 1130 or to deliver fluid at a selected rate through the fittings 1130 based on data received from the user interface 1120.

In certain embodiments, the user interface 1120 can include one or more knobs or dials 1125. Alternatively, the user interface can include a keypad, a touch screen, a keyboard, a switch, or any other user interface known in the art. In certain embodiments, instructions or settings may be communicated to the processor 1155 from an external device such as a mobile device, a computer, or a server.

In certain embodiments, the user interface 1120 may allow for selection of different amounts of inflation or different rates of inflation through different fluid fittings 1150 to allow for varied amounts of inflation in different inflatables coupled to the pump 1100.

The pump system 1100 can be used to control the inflation of one or more of the inflatable components described herein, such as, for example, inflatable bladders 32, 34, 132, 134, 516, 518, 519, and 918.

Although there has been hereinabove described a specific abdominal muscle and spine-exercising devices and traction devices in accordance with the present invention for the purpose of illustrating the manner in which the invention may be used to advantage, it should be appreciated that the invention is not limited thereto. That is, the present invention may suitably comprise, consist of or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

The various devices, systems and methods described above provide a number of ways to carry out some preferred embodiments of the invention. Of course, it is to be understood that not necessarily all objectives or advantages described may be achieved in accordance with any particular embodiment described herein. Thus, for example, those skilled in the art will recognize that the devices and systems may be made and the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various components, features and steps discussed above, as well as other known equivalents for each such component, feature or step, can be mixed and matched by one of ordinary skill in this art to make devices and systems and perform methods in accordance with principles described herein.

Although the invention has been disclosed in the context of some embodiments and examples, it will be understood by those skilled in the art that the invention extends beyond these specifically disclosed embodiments to other alternative embodiments and/or uses and obvious modifications and equivalents thereof. Accordingly, the invention is not intended to be limited by the specific disclosures of preferred embodiments herein.

What is claimed is:

1. A spinal treatment system comprising:
a traction device comprising:
   a frame having a base and a neck support coupled to the base to support the neck of a user during use; and
   an inflatable bladder system coupled to a neck support and configured to expand, wherein upon the inflatable bladder system expanding, the inflatable bladder system imparts a force to an occipital-cervical junction of the user, a cervical spine of the user, and a thoracic spine of the user at one time;
an exercise device adapted for imparting curvature to the lumbar or sacral spine of the user and for manipulating the spine and intervertebral discs with decompression force, said exercise device comprising:
   a frame for placement on a floor and having a top surface and a bottom surface, the bottom surface configured to rest upon the floor, wherein the top surface and bottom surface are in a spaced apart relationship and forming a hollow portion therebetween;
   a pad having a volume that is not configured to be inflatable carried by the top surface of the frame; and
   a body strap attachment configured to encompass a thoracic-sacral spinal vertebrae region of the user and configured to secure the frame to the user; and
a cushion coupled to the traction device and configured to bear against the thoracic spine of the user, the cushion comprising one or more pad sections or inflatable bladder sections.

2. The spinal treatment system of claim 1, wherein the pad or inflatable bladder of the exercise device is a first pad or first inflatable bladder, wherein the exercise device further comprises a second pad or second inflatable bladder carried by the top surface of the frame.

3. The spinal treatment system of claim 2, wherein the first pad or first inflatable bladder is disposed for directly bearing against the lower thoracic and upper lumbar vertebrae of the spine of the user.

4. The spinal treatment system of claim 2, wherein the second pad or second inflatable bladder is disposed for directly bearing against the mid-lumbar and lumbo-sacral vertebrae of the spine of the user.

5. The spinal treatment system of claim 1, further comprising a pump system, wherein the pump system comprises:
   a user interface configured to receive one or more selections from a user;
   a fluid delivery system configured to direct flow of fluid to the inflatable bladder system of the traction device; and
   a processor in communication with the user interface and the fluid delivery system, the processor configured to:
      receive the one or more selections from the user interface; and
      control the fluid delivery system to direct the flow of fluid to the inflatable bladder system based on the one or more selections.

6. The spinal treatment system of claim 5, wherein the processor is configured to control the fluid delivery system to inflate the inflatable bladder system to a user selected inflation amount or at a user selected inflation rate.

7. The spinal treatment system of claim 1, further comprising an elongate stirrup strap member having a proximal end and a distal end, the proximal end attachable to the frame, wherein the proximal end is adapted to be disposed behind the spinal region of the user.

8. The spinal treatment system of claim 1, wherein the pad of the exercise device is disposed for directly bearing against the lower thoracic and upper lumbar vertebrae of the spine of the user and the mid-lumbar and lumbo-sacral vertebrae of the spine of the user.

9. The spinal treatment system of claim 1, further comprising one or more straps configured to couple the traction device with the exercise device.

10. The spinal treatment system of claim 1, further comprising one or more straps configured to couple the cushion with the exercise device.

11. A spinal treatment system comprising:
a traction device comprising:
   a frame having a base and a neck support coupled to the base to support a neck of a user during use;
   a first inflatable bladder portion coupled to the neck support, the first inflatable bladder portion being expandable in an outward direction from the neck support toward the neck of the user and in a transverse direction normal to the outward direction upon inflation;
   a second inflatable bladder portion coupled to the neck support and configured to expand in a first angular direction from the neck support, the second inflatable bladder portion being positioned inferior to the first inflatable bladder portion; and
   a third inflatable bladder portion coupled to the neck support and configured to be positioned superior to the first inflatable bladder portion, the third inflatable bladder portion being expandable in a second angular direction from the neck support toward an occiput of the user upon inflation; and
   wherein upon the first inflatable bladder portion expanding in the outward direction, the first inflatable bladder portion bears outwardly against a back of the neck of the user as the first inflatable bladder portion is inflated and forces a cervical spine of the user to curve forwardly, and upon expanding in the transverse direction, the first inflatable bladder portion applies an angular traction to the cervical spine as the first inflatable bladder portion is inflated;
   wherein upon the second inflatable bladder portion expanding in the first angular direction, the second inflatable bladder portion bears angularly against an upper thoracic region of a thoracic spine of the user as the second inflatable bladder portion is inflated and forces the thoracic spine of the user to decompress and reduces hyper-kyphosis of the upper thoracic region; and
   wherein upon the third inflatable bladder portion expanding in the second angular direction, the third inflatable bladder portion bears angularly against the occiput of the user as the third inflatable bladder portion is inflated to decompress an occipital-cervical junction of the user; and an exercise device adapted for imparting curvature to the lumbar or sacral spine of the user and for manipulating the spine and intervertebral discs with decompression force, said exercise device comprising:
a frame for placement on a floor and having a top surface and a bottom surface, the bottom surface configured to rest upon the floor, wherein the top surface and bottom surface are in a spaced apart relationship and forming a hollow portion therebetween;
a pad carried by the top surface of the frame; and
a body strap attachment configured to encompass a thoracic-sacral spinal vertebrae region of the user and configured to secure the frame to the user.

12. The spinal treatment system of claim 11, wherein the pad of the exercise device is a first pad or first inflatable bladder, wherein the exercise device further comprises a second pad or second inflatable bladder carried by the top surface of the frame.

13. The spinal treatment system of claim 12, wherein the first pad or first inflatable bladder is disposed for directly bearing against the lower thoracic and upper lumbar vertebrae of the spine of the user.

14. The spinal treatment system of claim 12, wherein the second pad or second inflatable bladder is disposed for directly bearing against the mid-lumbar and lumbo-sacral vertebrae of the spine of the user.

15. The spinal treatment system of claim 11, further comprising an elongate stirrup strap member having a proximal end and a distal end, the proximal end attachable to the frame, wherein the proximal end is adapted to be disposed behind the spinal region of the user.

16. The spinal treatment system of claim 11, wherein the pad of the exercise device is disposed for directly bearing against the lower thoracic and upper lumbar vertebrae of the spine of the user and the mid-lumbar and lumbo-sacral vertebrae of the spine of the user.

17. The spinal treatment system of claim 11, further comprising one or more straps configured to couple the traction device with the exercise device.

18. The spinal treatment system of claim 11, further comprising a pump system, wherein the pump system comprises:
a user interface configured to receive one or more selections from a user;
a fluid delivery system configured to direct flow of fluid to one or more of the first inflatable bladder portion, the second inflatable bladder portion, and the third inflatable bladder portion of the traction device; and
a processor in communication with the user interface and the fluid delivery system, the processor configured to:
receive the one or more selections from the user interface; and
control the fluid delivery system to direct the flow of fluid to the one or more of the first inflatable bladder portion, the second inflatable bladder portion, and the third inflatable bladder portion of the traction device based on the one or more selections.

19. A spinal treatment system comprising:
a traction device comprising:
a frame having a base and a neck support coupled to the base to support a neck of a user during use;
a first inflatable bladder portion coupled to the neck support, the first inflatable bladder portion being expandable in an outward direction from the neck support toward the neck of the user and in a transverse direction normal to the outward direction upon inflation;
a second inflatable bladder portion coupled to the neck support and configured to expand in a first angular direction from the neck support; and
a third inflatable bladder portion coupled to the neck support, the third inflatable bladder portion being expandable in a second angular direction from the neck support;
an exercise device adapted for imparting curvature to a lumbar or sacral spine of a user and for manipulating a spine and intervertebral discs with decompression force, said exercise device comprising:
a frame for placement on a floor and having a top surface and a bottom surface, the bottom surface configured to rest upon the floor, wherein the top surface and bottom surface are in a spaced apart relationship forming a hollow portion therebetween;
a pad carried by the top surface of the frame; and
a body strap attachment configured to encompass the thoracic-sacral spinal vertebrae region of the user and configured to secure the frame to the user; and
a cushion coupled to the exercise device and configured to bear against the thoracic spine of the user, the cushion comprising a plurality of pad sections.

20. The spinal treatment system of claim 19, wherein the pad of the exercise device is a first pad or first inflatable bladder, wherein the exercise device further comprises a second pad or second inflatable bladder carried by the top surface of the frame.

21. The spinal treatment system of claim 20, wherein the first pad or first inflatable bladder is disposed for directly bearing against the lower thoracic and upper lumbar vertebrae of the spine of the user.

22. The spinal treatment system of claim 20, wherein the second pad or second inflatable bladder is disposed for directly bearing against the mid-lumbar and lumbo-sacral vertebrae of the spine of the user.

23. The spinal treatment system of claim 19, further comprising an elongate stirrup strap member having a proximal end and a distal end, the proximal end attachable to the frame, wherein the proximal end is adapted to be disposed behind the spinal region of the user.

24. The spinal treatment system of claim 19, wherein the pad of the exercise device is disposed for directly bearing against the lower thoracic and upper lumbar vertebrae of the spine of the user and the mid-lumbar and lumbo-sacral vertebrae of the spine of the user.

25. The spinal treatment system of claim 19, further comprising one or more straps configured to couple the cushion with the exercise device.

26. A method for exercising and decompressing lower body muscles, leg muscles, abdominal muscles and spine, comprising the steps of:
providing a frame with a pad having a volume that is not configured to be inflatable disposed on a top portion of the frame, said top portion of said frame disposed on a bottom of said frame, the frame comprising a hollow portion between the top portion and bottom of said frame;
positioning the pad against one or more of the lower thoracic and upper lumbar vertebrae and the middle lumbar and lumbo-sacral vertebrae of a user at one time in order to create traction and spinal arc in the lower spinal region and to stretch lower body muscle groups and leg muscles;

encompassing a thoracic-sacral spinal vertebrae region of the user and securing the frame with a body strap attachment, the body strap attachment passing through the frame in a non-fixed relationship and partially disposed within the hollow portion;

connecting an elongate stirrup strap to the frame and to a stirrup for encompassing the feet or legs of the user, wherein the elongate stirrup strap is disposed behind the user;

engaging slidably feet or legs of the user into the stirrup;

creating aligned decompression forces between the leg muscles and lower abdominal muscles by pulling the stirruped legs or feet in a direction away from the spine to decompress, urge, and align the spinal vertebrae;

securing a traction device to a head of the user, the traction device comprising:
 a frame having a base and a neck support coupled to the base to support the neck of a user during use;
 a first inflatable bladder portion coupled to the neck support, the first inflatable bladder portion being expandable in an outward direction from the neck support toward the neck of the user and in a transverse direction normal to the outward direction upon inflation;
 a second inflatable bladder portion coupled to the neck support and configured to expand in a first angular direction from the neck support; and
 a third inflatable bladder portion coupled to the neck support, the third inflatable bladder portion being expandable in a second angular direction from the neck support; and receiving a selection of one or more of the first inflatable bladder portion, the second inflatable bladder portion, and the third inflatable bladder portion by a user interface of a pump;

receiving a selection of an inflation amount or an inflation rate for each inflatable bladder of the selection of one or more of the first inflatable bladder portion, the second inflatable bladder portion, and the third inflatable bladder portion by the user interface of the pump, the pump comprising:

a fluid delivery system configured to direct flow of fluid to the first inflatable bladder portion, the second inflatable bladder portion, and the third inflatable bladder portion of the traction device; and a processor in communication with the user interface and the fluid delivery system, the processor configured to:
  receive the selection of one or more of the first inflatable bladder portion, the second inflatable bladder portion, and the third inflatable bladder portion;
  receive the selections of the inflation amount or the inflation rate from the user interface; and
  control the fluid delivery system to direct the flow of fluid to one or more of the first inflatable bladder portion, the second inflatable bladder portion, and the third inflatable bladder portion based on the selection of one or more of the first inflatable bladder portion, the second inflatable bladder portion, and the third inflatable bladder portion and the selections of the inflation amount or the inflation rate; and expanding one or more of the first inflatable bladder portion, the second inflatable bladder portion, and the third inflatable bladder portion using the pump.

27. The method of claim 26, wherein positioning the pad against one or more of the lower thoracic and upper lumbar vertebrae and the middle lumbar and lumbo-sacral vertebrae of the user comprises positioning the pad against the lower thoracic and upper lumbar vertebrae.

28. The method of claim 26, wherein positioning the pad against one or more of the lower thoracic and upper lumbar vertebrae and the middle lumbar and lumbo-sacral vertebrae of the user comprises positioning the pad against the middle lumbar and lumbo-sacral vertebrae.

29. The method of claim 26, wherein the pad is a first pad, wherein the method comprises positioning the first pad against the lower thoracic and upper lumbar vertebrae of the user, the method further comprising positioning a second pad against the middle lumbar and lumbo-sacral vertebrae.

\* \* \* \* \*